(12) United States Patent
Boyden et al.

(10) Patent No.: US 9,005,263 B2
(45) Date of Patent: Apr. 14, 2015

(54) SYSTEM, DEVICES, AND METHODS INCLUDING ACTIVELY-CONTROLLABLE STERILIZING EXCITATION DELIVERY IMPLANTS

(75) Inventors: Edward S. Boyden, Chestnut Hill, MA (US); Ralph G. Dacey, Jr., St. Louis, MO (US); Gregory J. Della Rocca, Columbia, MO (US); Joshua L. Dowling, Webster Groves, MO (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Nathan P. Myhrvold, Bellevue, WA (US); Dennis J. Rivet, Portsmouth, VA (US); Paul Santiago, St. Louis, MO (US); Michael A. Smith, Phoenix, AZ (US); Todd J. Stewart, St. Louis, MO (US); Elizabeth A. Sweeney, Seattle, WA (US); Clarence T. Tegreene, Bellevue, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1009 days.

(21) Appl. No.: 12/592,976

(22) Filed: Dec. 3, 2009

(65) Prior Publication Data

US 2010/0174346 A1 Jul. 8, 2010

Related U.S. Application Data

(63) Continuation-in-part of application No. 12/315,881, filed on Dec. 4, 2008, and a continuation-in-part of application No. 12/315,882, filed on Dec. 4, 2008, now abandoned, and a continuation-in-part of application (Continued)

(51) Int. Cl.
*A61F 7/12* (2006.01)
*A61L 2/03* (2006.01)
(Continued)

(52) U.S. Cl.
CPC ... *A61L 2/03* (2013.01); *A61F 2/30* (2013.01); *A61F 2002/009* (2013.01);
(Continued)

(58) Field of Classification Search
USPC .......................................................... 607/96
See application file for complete search history.

(56) References Cited

U.S. PATENT DOCUMENTS

| 2,602,724 A | 7/1952 | Batchelor |
| 3,274,406 A | 9/1966 | Sommers, Jr. |

(Continued)

FOREIGN PATENT DOCUMENTS

| BE | 1015999 A3 | 1/2006 |
| DE | 198 57 268.9 A1 | 6/2000 |

(Continued)

OTHER PUBLICATIONS

European Search Report; European App. No. EP 08 83 4851; Dec. 2, 2010 (received by our Agent on Dec. 14, 2010); pp. 1-6.

(Continued)

*Primary Examiner* — Joseph Stoklosa
*Assistant Examiner* — Kaitlyn Smith

(57) ABSTRACT

Systems, devices, methods, and compositions are described for providing an actively-controllable disinfecting implantable device configured to, for example, treat or prevent an infection in a biological subject.

33 Claims, 26 Drawing Sheets

Related U.S. Application Data

No. 12/315,885, filed on Dec. 4, 2008, now abandoned, and a continuation-in-part of application No. 12/315,883, filed on Dec. 4, 2008, and a continuation-in-part of application No. 12/315,880, filed on Dec. 4, 2008, now Pat. No. 8,162,924, and a continuation-in-part of application No. 12/315,884, filed on Dec. 4, 2008, and a continuation-in-part of application No. 12/380,553, filed on Feb. 27, 2009.

(51) Int. Cl.
| | | |
|---|---|---|
| *A61F 2/30* | (2006.01) | |
| *A61L 2/00* | (2006.01) | |
| *A61F 2/00* | (2006.01) | |
| *A61F 2/48* | (2006.01) | |
| *A61N 1/20* | (2006.01) | |
| *A61N 1/372* | (2006.01) | |
| *A61N 1/378* | (2006.01) | |

(52) U.S. Cl.
CPC ............ A61F 2002/30087 (2013.01); A61F 2002/3067 (2013.01); A61F 2002/30677 (2013.01); A61F 2002/3068 (2013.01); A61F 2002/3084 (2013.01); A61F 2002/30932 (2013.01); A61F 2002/481 (2013.01); A61F 2002/482 (2013.01); A61F 2250/0002 (2013.01); A61F 2250/0068 (2013.01); A61F 2310/00616 (2013.01); *A61L 2/0011* (2013.01); A61N 1/205 (2013.01); A61N 1/37252 (2013.01); A61N 1/3785 (2013.01); A61N 1/3787 (2013.01)

(56) References Cited

U.S. PATENT DOCUMENTS

| | | | |
|---|---|---|---|
| 3,825,016 A | 7/1974 | Lale et al. | |
| 4,081,764 A | 3/1978 | Christmann et al. | |
| 4,598,579 A | 7/1986 | Cummings et al. | |
| 4,698,058 A | 10/1987 | Greenfeld et al. | |
| 4,718,417 A | 1/1988 | Kittrell et al. | |
| 4,788,975 A | 12/1988 | Shturman et al. | |
| 4,863,849 A | 9/1989 | Melamede | |
| 4,900,553 A | 2/1990 | Silver et al. | |
| 5,000,731 A | 3/1991 | Wong et al. | |
| 5,127,735 A | 7/1992 | Pitt | |
| 5,155,707 A | 10/1992 | Fisher | |
| 5,156,839 A | 10/1992 | Pennell et al. | |
| 5,164,164 A | 11/1992 | Strickler et al. | |
| 5,240,675 A | 8/1993 | Wilk et al. | |
| 5,260,020 A | 11/1993 | Wilk et al. | |
| 5,281,199 A | 1/1994 | Ensminger et al. | |
| 5,302,345 A | 4/1994 | Oksman et al. | |
| 5,324,275 A | 6/1994 | Raad et al. | |
| 5,326,567 A | 7/1994 | Capelli | |
| 5,367,720 A | 11/1994 | Stephens et al. | |
| 5,431,694 A | 7/1995 | Snaper et al. | |
| 5,445,608 A | 8/1995 | Chen et al. | |
| 5,594,544 A | 1/1997 | Horiuchi et al. | |
| 5,607,683 A | 3/1997 | Capelli | |
| 5,622,848 A | 4/1997 | Morrow | |
| 5,630,379 A | 5/1997 | Gerk et al. | |
| 5,681,260 A | 10/1997 | Ueda et al. | |
| 5,704,352 A | 1/1998 | Tremblay et al. | |
| 5,733,270 A | 3/1998 | Ling et al. | |
| 5,735,276 A | 4/1998 | Lemelson | |
| 5,750,093 A | 5/1998 | Menon et al. | |
| 5,766,934 A | 6/1998 | Guiseppi-Elie | |
| 5,771,528 A | 6/1998 | Nappi, Sr. | |
| 5,797,898 A | 8/1998 | Santini, Jr. et al. | |
| 5,810,015 A | 9/1998 | Flaherty | |
| 5,820,821 A | 10/1998 | Kawagoe et al. | |
| 5,855,203 A | 1/1999 | Matter | |
| 5,865,744 A | 2/1999 | Lemelson | |
| 5,961,923 A | 10/1999 | Nova et al. | |
| 5,978,713 A | 11/1999 | Prutchi et al. | |
| 5,993,378 A * | 11/1999 | Lemelson .................... 600/109 |
| 5,993,382 A | 11/1999 | Pruitt, Sr. | |
| 6,008,896 A | 12/1999 | Sabsabi et al. | |
| 6,057,561 A | 5/2000 | Kawasaki et al. | |
| 6,086,851 A | 7/2000 | Boni et al. | |
| 6,135,990 A | 10/2000 | Heller et al. | |
| 6,143,035 A | 11/2000 | McDowell | |
| 6,162,242 A | 12/2000 | Peyman | |
| 6,222,953 B1 | 4/2001 | Hoekstra et al. | |
| 6,266,551 B1 | 7/2001 | Osadchy et al. | |
| 6,280,604 B1 | 8/2001 | Allen et al. | |
| 6,282,444 B1 | 8/2001 | Kroll et al. | |
| 6,304,786 B1 | 10/2001 | Heil, Jr. et al. | |
| 6,312,770 B1 | 11/2001 | Sage et al. | |
| 6,348,042 B1 | 2/2002 | Warren, Jr. | |
| 6,350,263 B1 | 2/2002 | Wetzig et al. | |
| 6,403,337 B1 | 6/2002 | Bailey et al. | |
| 6,418,342 B1 | 7/2002 | Owen et al. | |
| 6,426,066 B1 | 7/2002 | Najafi et al. | |
| 6,428,491 B1 | 8/2002 | Weiss | |
| 6,440,097 B1 | 8/2002 | Kupiecki | |
| 6,443,147 B1 | 9/2002 | Matter | |
| 6,451,003 B1 | 9/2002 | Prosl et al. | |
| 6,461,569 B1 | 10/2002 | Boudreaux | |
| 6,470,212 B1 | 10/2002 | Weijand et al. | |
| 6,470,888 B1 | 10/2002 | Matter | |
| 6,478,778 B1 | 11/2002 | Jacobsen et al. | |
| 6,488,704 B1 | 12/2002 | Connelly et al. | |
| 6,491,666 B1 | 12/2002 | Santini, Jr. et al. | |
| 6,506,416 B1 | 1/2003 | Okauchi et al. | |
| 6,533,733 B1 | 3/2003 | Ericson et al. | |
| 6,542,767 B1 * | 4/2003 | McNichols et al. .......... 600/407 |
| 6,551,346 B2 | 4/2003 | Crossley | |
| 6,562,295 B1 | 5/2003 | Neuberger | |
| 6,585,677 B2 | 7/2003 | Cowan, Jr. et al. | |
| 6,599,274 B1 | 7/2003 | Kucharczyk et al. | |
| 6,626,902 B1 | 9/2003 | Kucharczyk et al. | |
| 6,667,807 B2 | 12/2003 | Lieberman | |
| 6,730,113 B2 | 5/2004 | Eckhardt et al. | |
| 6,743,190 B2 | 6/2004 | Connelly et al. | |
| 6,750,055 B1 | 6/2004 | Connelly et al. | |
| 6,764,501 B2 | 7/2004 | Ganz | |
| 6,789,183 B1 | 9/2004 | Smith et al. | |
| 6,793,642 B2 | 9/2004 | Connelly et al. | |
| 6,793,880 B2 | 9/2004 | Kippenhan, Jr. | |
| 6,802,811 B1 | 10/2004 | Slepian | |
| 6,831,748 B2 | 12/2004 | Tittel et al. | |
| 6,838,292 B1 | 1/2005 | Rajan et al. | |
| 6,844,028 B2 | 1/2005 | Mao et al. | |
| 6,849,463 B2 | 2/2005 | Santini, Jr. et al. | |
| 6,853,765 B1 | 2/2005 | Cochran | |
| 6,887,202 B2 | 5/2005 | Currie et al. | |
| 6,908,460 B2 | 6/2005 | DiStefano | |
| 6,913,589 B2 | 7/2005 | Dextradeur et al. | |
| 6,914,279 B2 | 7/2005 | Lu et al. | |
| 6,918,869 B2 | 7/2005 | Shaw et al. | |
| 6,932,787 B2 | 8/2005 | Cowan et al. | |
| 6,939,290 B2 | 9/2005 | Iddan | |
| 6,960,201 B2 | 11/2005 | Cumbie | |
| 6,969,382 B2 | 11/2005 | Richter | |
| 6,980,716 B1 | 12/2005 | Diaz et al. | |
| 7,020,355 B2 | 3/2006 | Lahann et al. | |
| 7,030,989 B2 | 4/2006 | Yager et al. | |
| 7,041,130 B2 | 5/2006 | Santini, Jr. et al. | |
| 7,052,488 B2 | 5/2006 | Uhland | |
| 7,070,590 B1 | 7/2006 | Santini, Jr. et al. | |
| 7,070,592 B2 | 7/2006 | Santini, Jr. et al. | |
| 7,078,903 B2 | 7/2006 | Paliwal et al. | |
| 7,116,857 B2 | 10/2006 | Faris | |
| 7,117,807 B2 | 10/2006 | Bohn, Jr. et al. | |
| 7,118,548 B2 | 10/2006 | Børgesen | |
| 7,130,459 B2 | 10/2006 | Anderson et al. | |
| 7,134,999 B2 | 11/2006 | Brauker et al. | |
| 7,143,709 B2 | 12/2006 | Brennan et al. | |
| 7,151,139 B2 | 12/2006 | Tiller et al. | |
| 7,159,590 B2 | 1/2007 | Rife | |

(56) References Cited

U.S. PATENT DOCUMENTS

| | | |
|---|---|---|
| 7,160,931 B2 | 1/2007 | Cheng et al. |
| 7,167,734 B2 | 1/2007 | Khalil et al. |
| 7,167,755 B2 | 1/2007 | Seeberger et al. |
| 7,183,048 B2 | 2/2007 | Felkner et al. |
| 7,195,608 B2 | 3/2007 | Burnett |
| 7,217,425 B2 | 5/2007 | Serhan et al. |
| 7,221,456 B2 | 5/2007 | Kanai et al. |
| 7,226,441 B2 | 6/2007 | Kulessa |
| 7,232,429 B2 | 6/2007 | Moreci |
| 7,236,821 B2 | 6/2007 | Cates et al. |
| 7,238,363 B2 | 7/2007 | Mansouri et al. |
| 7,244,232 B2 | 7/2007 | Connelly et al. |
| 7,250,615 B1 | 7/2007 | Soong et al. |
| 7,253,152 B2 | 8/2007 | Panero et al. |
| 7,276,255 B2 | 10/2007 | Selkon |
| 7,288,232 B2 | 10/2007 | Morrow et al. |
| 7,306,620 B2 | 12/2007 | Cumbie |
| 7,309,330 B2 | 12/2007 | Bertrand et al. |
| 7,310,459 B1 | 12/2007 | Rahman |
| 7,322,965 B2 | 1/2008 | Gibson et al. |
| 7,334,594 B2 | 2/2008 | Ludin |
| 7,345,372 B2 | 3/2008 | Roberts et al. |
| 7,348,021 B2 | 3/2008 | Klein |
| 7,354,575 B2 | 4/2008 | Shachar et al. |
| 7,365,859 B2 | 4/2008 | Yun et al. |
| 7,367,342 B2 | 5/2008 | Butler |
| 7,390,310 B2 | 6/2008 | McCusker et al. |
| 7,396,676 B2 | 7/2008 | Robotti et al. |
| 7,442,372 B2 | 10/2008 | Kakkis |
| 7,455,667 B2 | 11/2008 | Uhland et al. |
| 7,524,298 B2 | 4/2009 | Gharib et al. |
| 7,535,692 B2 | 5/2009 | Krupenkin et al. |
| 7,570,018 B2 | 8/2009 | Waguespack |
| 7,621,905 B2 | 11/2009 | Penner et al. |
| 7,650,848 B2 | 1/2010 | Brennan et al. |
| 7,691,684 B2 | 4/2010 | Breitwisch et al. |
| 7,691,894 B2 | 4/2010 | Ono et al. |
| 7,706,178 B2 | 4/2010 | Parkinson |
| 7,714,326 B2 | 5/2010 | Kim et al. |
| 7,744,555 B2 | 6/2010 | DiMauro et al. |
| 7,837,719 B2 | 11/2010 | Brogan et al. |
| 8,197,452 B2 | 6/2012 | Harding et al. |
| 8,496,610 B2 | 7/2013 | Levenson et al. |
| 2002/0030196 A1 | 3/2002 | Iwata et al. |
| 2002/0090388 A1 | 7/2002 | Humes et al. |
| 2002/0123787 A1 | 9/2002 | Weiss |
| 2002/0182262 A1 | 12/2002 | Selkon |
| 2002/0188323 A1 | 12/2002 | Penner et al. |
| 2002/0192366 A1 | 12/2002 | Cramer et al. |
| 2002/0192680 A1 | 12/2002 | Chan et al. |
| 2003/0012688 A1 | 1/2003 | Kippenhan, Jr. |
| 2003/0014091 A1 | 1/2003 | Rastegar et al. |
| 2003/0017073 A1 | 1/2003 | Eckhardt et al. |
| 2003/0092996 A1 | 5/2003 | Lowe et al. |
| 2003/0109907 A1 | 6/2003 | Shadduck |
| 2003/0165702 A1 | 9/2003 | Disse et al. |
| 2003/0195415 A1 | 10/2003 | Iddan |
| 2003/0199806 A1 | 10/2003 | Kieval |
| 2003/0204163 A1 | 10/2003 | Marchitto et al. |
| 2003/0214579 A1 | 11/2003 | Iddan |
| 2003/0225331 A1 | 12/2003 | Diederich et al. |
| 2004/0022669 A1 | 2/2004 | Ruan et al. |
| 2004/0073278 A1 | 4/2004 | Pachys |
| 2004/0098055 A1 | 5/2004 | Kroll et al. |
| 2004/0149582 A1 | 8/2004 | Kovacs |
| 2004/0186546 A1* | 9/2004 | Mandrusov et al. .......... 607/122 |
| 2004/0208940 A1 | 10/2004 | Selkon |
| 2004/0237255 A1 | 12/2004 | Lin et al. |
| 2004/0253138 A1 | 12/2004 | Malak |
| 2004/0260249 A1 | 12/2004 | Kulessa |
| 2005/0008285 A1 | 1/2005 | Kim et al. |
| 2005/0043894 A1 | 2/2005 | Fernandez |
| 2005/0045183 A1 | 3/2005 | Callister et al. |
| 2005/0049181 A1 | 3/2005 | Madhyastha |
| 2005/0063647 A1 | 3/2005 | Thornton et al. |
| 2005/0089890 A1 | 4/2005 | Cubicciotti |
| 2005/0095351 A1 | 5/2005 | Zumeris et al. |
| 2005/0100937 A1 | 5/2005 | Holmes |
| 2005/0105077 A1 | 5/2005 | Padmanabhan et al. |
| 2005/0142157 A1 | 6/2005 | Alimi |
| 2005/0164169 A1 | 7/2005 | Malak |
| 2005/0171434 A1 | 8/2005 | Madden et al. |
| 2005/0171437 A1 | 8/2005 | Carberry |
| 2005/0175658 A1 | 8/2005 | DiMauro et al. |
| 2005/0180678 A1 | 8/2005 | Panepucci et al. |
| 2005/0192478 A1 | 9/2005 | Williams et al. |
| 2005/0196421 A1 | 9/2005 | Hunter et al. |
| 2005/0203495 A1 | 9/2005 | Malak |
| 2005/0203582 A1 | 9/2005 | Healy et al. |
| 2005/0209665 A1 | 9/2005 | Hunter et al. |
| 2005/0245557 A1 | 11/2005 | Schoenhard et al. |
| 2005/0255604 A1 | 11/2005 | Gjerde et al. |
| 2005/0256554 A1 | 11/2005 | Malak |
| 2005/0263386 A9 | 12/2005 | Pitts, Jr. et al. |
| 2005/0266582 A1 | 12/2005 | Modlin et al. |
| 2005/0268921 A1 | 12/2005 | Zumeris et al. |
| 2005/0272974 A1 | 12/2005 | Iddan |
| 2005/0288654 A1 | 12/2005 | Nieman et al. |
| 2006/0004317 A1 | 1/2006 | Mauge et al. |
| 2006/0004431 A1 | 1/2006 | Fuller et al. |
| 2006/0009805 A1 | 1/2006 | Jensen et al. |
| 2006/0020186 A1 | 1/2006 | Brister et al. |
| 2006/0020239 A1 | 1/2006 | Geiger et al. |
| 2006/0047283 A1 | 3/2006 | Evans, III et al. |
| 2006/0047329 A1* | 3/2006 | Krespi et al. .................... 607/86 |
| 2006/0074479 A1 | 4/2006 | Bailey et al. |
| 2006/0079740 A1 | 4/2006 | Silver et al. |
| 2006/0079762 A1 | 4/2006 | Norris et al. |
| 2006/0105275 A1 | 5/2006 | Maloney et al. |
| 2006/0122543 A1 | 6/2006 | Mayer et al. |
| 2006/0139667 A1 | 6/2006 | Morimoto et al. |
| 2006/0140911 A1 | 6/2006 | Sharp et al. |
| 2006/0147492 A1 | 7/2006 | Hunter et al. |
| 2006/0159916 A1 | 7/2006 | Dubrow et al. |
| 2006/0210602 A1 | 9/2006 | Sehl et al. |
| 2006/0247525 A1 | 11/2006 | Huo et al. |
| 2006/0253259 A1 | 11/2006 | Fernandez |
| 2006/0271112 A1 | 11/2006 | Martinson et al. |
| 2006/0276713 A1 | 12/2006 | Maier |
| 2006/0287660 A1 | 12/2006 | Syed et al. |
| 2006/0289761 A1 | 12/2006 | Nabet et al. |
| 2007/0016163 A1 | 1/2007 | Santini, Jr. et al. |
| 2007/0031777 A1 | 2/2007 | Wang et al. |
| 2007/0073135 A1 | 3/2007 | Lee et al. |
| 2007/0074672 A1 | 4/2007 | Torgerson et al. |
| 2007/0087445 A1 | 4/2007 | Tearney et al. |
| 2007/0106333 A1 | 5/2007 | Fernandez |
| 2007/0111201 A1 | 5/2007 | Doranz |
| 2007/0142874 A1* | 6/2007 | John ................................ 607/45 |
| 2007/0156039 A1 | 7/2007 | Casciani et al. |
| 2007/0173755 A1 | 7/2007 | Alimi et al. |
| 2007/0176117 A1 | 8/2007 | Redmond et al. |
| 2007/0187626 A1 | 8/2007 | Gaska et al. |
| 2007/0196357 A1 | 8/2007 | Alimi et al. |
| 2007/0197890 A1 | 8/2007 | Boock et al. |
| 2007/0205382 A1 | 9/2007 | Gaska et al. |
| 2007/0208245 A1 | 9/2007 | Brauker et al. |
| 2007/0209143 A1 | 9/2007 | Choi et al. |
| 2007/0225634 A1* | 9/2007 | Ferren et al. .................... 604/27 |
| 2007/0225800 A1 | 9/2007 | Sahatjian et al. |
| 2007/0249969 A1 | 10/2007 | Shields, Jr. |
| 2007/0259017 A1 | 11/2007 | Francis |
| 2007/0274909 A1 | 11/2007 | Justel et al. |
| 2007/0275068 A1* | 11/2007 | Martens et al. ............... 424/484 |
| 2007/0276208 A1 | 11/2007 | Connelly et al. |
| 2007/0280852 A1 | 12/2007 | Skubal et al. |
| 2007/0282190 A1 | 12/2007 | Dekel et al. |
| 2007/0299384 A1 | 12/2007 | Faul et al. |
| 2008/0007885 A1 | 1/2008 | Mehrl et al. |
| 2008/0014632 A1 | 1/2008 | Cunningham et al. |
| 2008/0033519 A1 | 2/2008 | Burwell et al. |
| 2008/0039678 A1 | 2/2008 | Montpetit et al. |
| 2008/0039768 A1 | 2/2008 | Francis |
| 2008/0051691 A1 | 2/2008 | Dragoon et al. |

(56) References Cited

U.S. PATENT DOCUMENTS

| | | |
|---|---|---|
| 2008/0051736 A1 | 2/2008 | Rioux et al. |
| 2008/0058798 A1 | 3/2008 | Wallace et al. |
| 2008/0064980 A1 | 3/2008 | Lee et al. |
| 2008/0095977 A1 | 4/2008 | Aizenberg et al. |
| 2008/0118546 A1 | 5/2008 | Thatcher et al. |
| 2008/0119421 A1 | 5/2008 | Tuszynski et al. |
| 2008/0125838 A1 | 5/2008 | Francis |
| 2008/0195170 A1 | 8/2008 | Asgari |
| 2008/0223717 A1 | 9/2008 | Isaksson et al. |
| 2008/0234786 A1 | 9/2008 | Cumbie |
| 2008/0243231 A1 | 10/2008 | Flanagan et al. |
| 2008/0248993 A1 | 10/2008 | Hannappel et al. |
| 2008/0253712 A1 | 10/2008 | Allen et al. |
| 2008/0257355 A1 | 10/2008 | Rao et al. |
| 2008/0265179 A1 | 10/2008 | Havens et al. |
| 2009/0012626 A1 | 1/2009 | Thompson et al. |
| 2009/0015841 A1 | 1/2009 | Downey |
| 2009/0018424 A1 | 1/2009 | Kamath et al. |
| 2009/0048542 A1 | 2/2009 | Varadan et al. |
| 2009/0048648 A1 | 2/2009 | Dacey, Jr. et al. |
| 2009/0054824 A1 | 2/2009 | Melsheimer et al. |
| 2009/0054827 A1 | 2/2009 | Eide |
| 2009/0066195 A1 | 3/2009 | Wang et al. |
| 2009/0110711 A1 | 4/2009 | Trollsas et al. |
| 2009/0118661 A1 | 5/2009 | Moehle et al. |
| 2009/0156460 A1 | 6/2009 | Jiang et al. |
| 2009/0177254 A1 | 7/2009 | Boyden et al. |
| 2009/0185988 A1 | 7/2009 | Maleski et al. |
| 2009/0195120 A1 | 8/2009 | Knospe |
| 2009/0209904 A1 | 8/2009 | Peeters |
| 2009/0281412 A1 | 11/2009 | Boyden et al. |
| 2009/0299153 A1 | 12/2009 | Gerber et al. |
| 2009/0316195 A1 | 12/2009 | Tseng et al. |
| 2010/0063404 A1 | 3/2010 | Kaplan et al. |
| 2010/0145286 A1 | 6/2010 | Zhang et al. |
| 2010/0198357 A1 | 8/2010 | Fuller et al. |
| 2010/0204802 A1 | 8/2010 | Wilson et al. |
| 2010/0234792 A1 | 9/2010 | Dacey, Jr. et al. |
| 2010/0249692 A1 | 9/2010 | Dacey, Jr. et al. |
| 2010/0256607 A1 | 10/2010 | Burnett |
| 2011/0116967 A1 | 5/2011 | Roy et al. |
| 2011/0117582 A1 | 5/2011 | Malima et al. |
| 2011/0160643 A1 | 6/2011 | Dacey, Jr. et al. |

FOREIGN PATENT DOCUMENTS

| | | |
|---|---|---|
| EP | 1 614 442 A2 | 1/2006 |
| JP | 4-502671 | 5/1992 |
| JP | H11117194 | 4/1999 |
| JP | 2001-506890 | 5/2001 |
| JP | 2002-525631 | 8/2002 |
| JP | 2006-061886 | 9/2006 |
| KR | 2006/0089415 A | 8/2006 |
| WO | WO 91/06855 A2 | 5/1991 |
| WO | WO/92/01222 | 1/1992 |
| WO | WO/97/00586 | 1/1997 |
| WO | WO/00/09733 | 2/2000 |
| WO | WO/00/29613 | 5/2000 |
| WO | WO/00/56185 | 9/2000 |
| WO | WO/01/13926 A2 | 3/2001 |
| WO | WO/01/54704 A1 | 8/2001 |
| WO | WO 02/068049 A1 | 9/2002 |
| WO | WO/02/102421 A1 | 12/2002 |
| WO | WO/2004/027116 A2 | 4/2004 |
| WO | WO/2004/031077 A2 | 4/2004 |
| WO | WO/2005/100100 A1 | 10/2005 |
| WO | WO/2005/117914 A2 | 12/2005 |
| WO | WO 2006/000764 A1 | 1/2006 |
| WO | WO/2006/044324 A2 | 4/2006 |
| WO | WO 2006/074454 A2 | 7/2006 |
| WO | WO/2007/070801 A3 | 6/2007 |
| WO | WO/2007/085021 A3 | 7/2007 |
| WO | WO 2007/140544 A1 | 12/2007 |
| WO | WO/2008/020770 A1 | 2/2008 |
| WO | WO/2008/073774 A1 | 6/2008 |
| WO | WO/2008/083390 A2 | 10/2008 |
| WO | WO 2009/067682 A2 | 5/2009 |

OTHER PUBLICATIONS

Apple et al.; "Review: Future Biomarkers for Detection of Ischemia and Risk Stratification in Acute Coronary Syndrome"; Clinical Chemistry; bearing a date of 2005; pp. 810-824; vol. 51, No. 5; American Association for Clinical Chemistry.

Barnes et al.; "Novel Biomarkers Associated with Deep Venous Thrombosis: A Comprehensive Review"; Biomarker Insights; bearing a date of 2008; pp. 93-100; vol. 3; Creative Commons Attribution.

Beebe et al.; "Nanosecond, High-Intensity Pulsed Electric Fields Induce Apoptosis in Human Cells"; The FASEB Journal; bearing a date of Jun. 17, 2003; pp. 1-23.

Cheng et al.; "Electrically Switchable and Optically Rewritable Reflective Fresnel Zone Plate in Dye-Doped Cholesteric Liquid Crystals"; Optics Express; bearing a date of Oct. 17, 2007; pp. 14078-14085; vol. 15, No. 21; OSA.

Coppola et al.; "Visualization of Optical Deflection and Switching Operations by a Domain-Engineered-Based $LinbO_3$ Electro-Optic Device"; Optics Express; bearing a date of May 19, 2003; vol. 11, No. 10; OSA.

Davis et al.; "A New Electro-Optic Waveguide Architecture and the Unprecedented Devices it Enables"; Proc. of SPIE; bearing a date of 2008; pp. 697503-1-697503-12; vol. 6975.

Frasca et al.; "Review: Prevention of Central Venous Catheter-Related Infection in the Intensive Care Unit"; Critical Care; bearing a date of 2010; pp. 1-8; vol. 14, No. 212; Springer-Verlag Berlin Heidelberg.

Feng et al.; "Plasmonic Effects in Dynamic Tunable Metal-Dielectric Composites"; Piers Online; bearing a date of 2008; pp. 625-630; vol. 4, No. 6.

European Search Report; European App. No. EP 08 25 1153; Jul. 10, 2009; pp. 1-2.

Giannitsis et al.; "Risk Stratification in Pulmonary Embolism Based on Biomarkers and Echocardiography"; Circulation: Journal of the American Heart Association; bearing a date of 2005; pp. 1520-1521; American Heart Association; located at: http://circ.ahajournals.org/cgi/content/full/112/11/1520.

Hall et al.; "Nanosecond Pulsed Electric Fields Induce Apoptosis in p53-wildtype and p53-null HCT116 Colon Carcinoma Cells"; Apoptosis; bearing a date of May 23, 2007; pp. 1721-1731; vol. 12; Springer Science+Business Media, LLC.

Horng et al.; "Tunable Optical Switch Using Magnetic Fluids"; Applied Physics Letters; bearing a date of Dec. 6, 2004; pp. 5592-5594; vol. 85, No. 23; American Institute of Physics.

Jaffer et al.; "In Vivo Imaging of Thrombin Activity in Experimental Thrombi with Thrombin-Sensitive Near-Infrared Molecular Probe"; Arteriosclerosis, Thrombosis, and Vascular Biology: Journal of the American Heart Association; bearing a date of Aug. 8, 2002; pp. 1929-1935; American Heart Association, Inc.; located at: http://atvb.ahajournals.org/cgi/content/full/22/11/1929.

Jaiswal et al.; "Long-Term Multiple Color Imaging of Live Cells Using Quantum Dot Bioconjugates"; Nature Biotechnology; bearing a date of Jan. 2003; pp. 47-51; vol. 21; Nature Publishing Group.

Kamphuisen et al.; "Can Anticoagulant Treatment be Tailored with Biomarkers in Patients with Venous Thromboembolism?"; Journal of Thrombosis and Haemostasis; bearing a date of 2006; pp. 1206-1207; vol. 4; International Society on Thrombosis and Haemostasis.

Krupenkin et al.; "Electrically Tunable Superhydrophobic Nanostructured Surfaces"; Bell Labs Technical Journal; bearing a date of 2005; pp. 161-170; vol. 10, No. 3; Lucent Technologies Inc.

Li et al.; "Feasibility of Interstitial Doppler Optical Coherence Tomography for In Vivo Detection of Microvascular Changes During Photodynamic Therapy"; Lasers in Surgery and Medicine; bearing a date of Jul. 2, 2006; pp. 754-761; vol. 38; Wiley-Liss Inc.

Liou et al.; "An ASIC Control Circuit for Thermal Actuated Large Optical Packet Switch Array"; Proceedings of the World Congress of Engineering; bearing a date of Jul. 2-4, 2008; pp. 1-6; vol. I; WCE.

(56) References Cited

OTHER PUBLICATIONS

Olcum et al.; "Tunable Surface Plasmon Resonance on an Elastomeric Substrate"; Optics Express; bearing a date of May 11, 2009; pp. 8542-8547; vol. 17, No. 10; OSA.
Piccolo et al.; "Antifuse Injectors for SOI LEDs"; printed in 2009; pp. 573-575.
Reynolds et al.; "Early Biomarkers of Stroke"; Clinical Chemistry: Oak Ridge Conference; bearing a date of Apr. 7, 2003; pp. 1733-1739; vol. 49, No. 10; American Association for Clinical Chemistry.
Rosalki et al.; "Cardiac Biomarkers for Detection of Myocardial Infarction: Perspectives from Past to Present"; Clinical Chemistry; bearing a date of Aug. 17, 2004; pp. 2205-2213; vol. 50, No. 11; American Association for Clinical Chemistry.
Shackleford et al.; "Integrated Plasmonic lens Photodetector"; Applied Physics Letters; bearing a date of Nov. 24, 2008; pp. 1-3; vol. 94, No. 083501; American Institute of Physics.
Smith et al.; "Evanescent Wave Imaging in Optical Lithography"; printed on Dec. 10, 2010; pp. 1-9.
Sport et al.; "Cassie-State Wetting Investigated by Means of a Hole-to-Pillar Density Gradient"; Langmuir Article; bearing a date Dec. 15, 2009; pp. 9465-9473; vol. 26, No. 12; American Chemical Society.
Thai et al.; "Development of a Fully-Integrated Ultrasensitive Wireless Sensor Utilizing Carbon Nanotubes and Surface Plasmon Theory"; Electronic Components and Technology Conference; bearing a date of 2008; pp. 436-439; IEEE.
Timko et al.; "Remotely Triggerable Drug Delivery Systems"; Advanced Materials; bearing a date of Jun. 4, 2010; pp. 4925-4943; vol. 22; Wiley-VCH Verlag GmbH&Co.
Tsutsui et al.; "Research: The use of Microbubbles to Target Drug Delivery"; BioMed Central-Open Access; bearing a date of Aug. 17, 2004; pp. 1-7; vol. 2, No. 23; BioMed Central Ltd.
Vàzquez et al.; "Optical Router for Optical Fiber Sensor Networks Based on a Liquid Crystal Cell"; IEEE Sensors Journal; bearing a date of Aug. 2003; pp. 513-518; vol. 3, No. 4; IEEE.
Wang et al.; "Effective in Plane Launching and Focusing Surface Plasmons by a Plasmonic Lens"; OSA; bearing a date of 2009; pp. 1-2; IEEE.
Yang et al.; "Polyimide-Waveguide-Based Thermal Optical Switch Using Total-Internal-Reflection Effect"; Applied Physics Letters; bearing a date of Oct. 14, 2002; pp. 2947-2949; vol. 81, No. 16; American Institute of Physics.
Extended European Search Report; App. No. EP 09 79 4832; Jan. 17, 2012 (received by our agent on Jan. 18, 2012); pp. 1-5.
Japanese Patent Office Official Notice of Rejection; Application No. 2008-209783; Mar. 6, 2012; 4 pages (no translation available).
PCT International Search Report; International App. No. PCT/US2010/003088; Apr. 1, 2011; pp. 1-4.
U.S. Appl. No. 12/218,214, Hyde et al.
U.S. Appl. No. 12/231,676, Hyde et al.
U.S. Appl. No. 11/973,010, Hyde et al.
Aarabi, Shahram et al.; "Research in Translation: Hypertrophic Scar Formation Following Burns and Trauma: New Approaches to Treatment"; PLoS Medicine; Sep. 2007; pp. 1464-1470; vol. 4, Issue 9, No. e234; located at: www.plosmedicine.org.
Abdollahi, Amir; "Apoptosis Signals in Lymphoblasts Induced by Focused Ultrasound"; The FASEB Journal-FJ Express; Sep. 2004; pp. 1413-1414; vol. 18; FASEB.
Albert, Richard K. and Condie, Frances; "Medical Intelligence: Hand-Washing Patterns in Medical Intensive-Care Units"; New England Journal of Medicine; Jun. 1981; pp. 1465-1466; vol. 304, No. 24.
"Arglaes® Controlled-Release Silver Technology"; Medline; 2003; 6 pages; Medline Industries, Inc.; located at: www.medline.com.
Ashush, Hagit et al.; "Apoptosis Induction of Human Myeloid Leukemic Cells by Ultrasound Exposure"; Cancer Research; bearing a date of Feb. 15, 2000; pp. 1014-1020; vol. 60.
Bozhevolnyi, Sergey I. et al.; "Photonic bandgap structures for long-range surface plasmon polaritons"; Optics Communications; bearing a date of 2005; pp. 328-333; vol. 250; Elsevier B.V.

Brogden, Kim A.; "Antimicrobial Peptides: Pore Formers or Metabolic Inhibitors in Bacteria?"; Nature Reviews, Microbiology; Mar. 2005; pp. 238-250; vol. 3.
Carcillo, Joseph A. et al.; "Early Markers of Infection and Sepsis in Newborns and Children"; Leading Article, Advances in Sepsis; 2006; pp. 118-125; vol. 5, No. 4.
Caricchio, Roberto et al.; "Ultraviolet B Radiation-Induced Cell Death: Critical Role of Ultraviolet Dose in Inflammation and Lupus Autoantigen Redistribution"; The Journal of Immunology; 2003; pp. 5778-5786; vol. 171; The American Association of Immunologists, Inc.
Chen, Ting-Hsuan et al.; "A Wettability Switchable Surface Driven by Electrostatic Induced Surface Morphology Change Without Energy Interference on Reagents in Droplets"; MEMS; Jan. 2006; pp. 178-181; IEEE.
Cheng, Gang et al.; "Switchable Polymer Surfaces: A Switchable Biocompatible Polymer Surface with Self-Sterilizing and Nonfouling Capabilities"; Angewandte Chemie; 2008; pp. 8831-8834; vol. 47; Wiley-VCH Verlag GmbH & Co.
De Fabo, Edward C.; "Advances in Brief: Ultraviolet B but not Ultraviolet A Radiation Initiates Melanoma"; Cancer Research; bearing a date of Sep. 15, 2004; pp. 6372-6376; vol. 64; American Association for Cancer Research.
Donlan, R. M. et al.; "Model Systems for Growing and Quantifying *Streptococcus Pneumoniae* Biofilms In Situ and in Real Time"; Applied and Environmental Microbiology; Aug. 2004; pp. 4980-4988; vol. 70, No. 8; American Society for Microbiology.
ESR European Search Report; European App. No. EP 08 25 1153; Dec. 15, 2008; p. 1.
"Fact Sheet: Cerebrospinal Fluid Shunt Systems for the Management of Hydrocephalus"; Hydrocephalus Association; 2000; 7 pages; Hydrocephalus Association; located at: www.hydroassoc.org.
Feng, Xinjian et al.; "Reversible Super-Hydrophobicity to Super-Hydrophilicity Transition of Aligned ZnO Nanorod Films"; JACS Communications; 2004; pp. 62-63; vol. 126; American Chemical Society.
Feng, Yi et al.; "Gastric Cancer: Low Intensity Ultrasound-Induced Apoptosis in Human Gastric Carcinoma Cells"; World Journal of Gastroenterology; bearing a date of Aug. 21, 2008; pp. 4873-4879; vol. 14, No. 31; The WJG Press; located at: www.wjgnet.com.
Fogh-Andersen, Niels et al.; "Composition of Interstitial Fluid"; General Clinical Chemistry; 1995; pp. 1522-1525; vol. 41, No. 10.
Forbes, Peter; "Scientific American: Self-Cleaning Materials: Lotus Leaf-Inspired Nanotechnology"; Scientific American Magazine; bearing a date of Jul. 30, 2008; pp. 1-5; printed on Nov. 21, 2008.
Goclawski, Jaroslaw et al.; "The Measurement of Wetting Angle by Applying and ADSA Model of Sessile Drop on Selected Textile Surfaces"; Fibres and Textiles in Eastern Europe; Apr./Jun. 2008; pp. 84-88; vol. 16, No. 2(67).
Grunfeld, Carl; "Lipids, Lipoproteins, Triglyceride Clearance, and Cytokines in Human Immunodeficiency Virus Infection and the Acquired Immunodeficiency Syndrome"; Journal of Clinical Endocrinology and Metabolism; 1992; pp. 1045-1052; vol. 74, No. 5; The Endocrine Society.
Imam, S.K. et al.; "Radiotracers for Imaging of Infection and Inflammation—A Review"; World Journal Nuclear Medicine.; Jan. 2006; pp. 40-55; vol. 5, No. 1.
"Introduction to ORP as the Standard of Postharvest Water Disinfection Monitoring"; UC Davis, Vegetable Research and Information Center; pp. 1-4.
Killer, H. E. et al.; "The Optic Nerve: A New Window into Cerebrospinal Fluid Composition?"; Brain; 2006; pp. 1027-1030; vol. 129.
Lahann, Joerg; "A Reversibly Switching Surface"; Reports, Science; bearing a date of Jan. 17, 2003; pp. 371-374 (plus Erratum); vol. 299; located at: www.sciencemag.org.
Lepock, James R.; "Cellular Effects of Hyperthermia: Relevance to the Minimum Dose for Thermal Damage"; International Journal of Hyperthermia, Taylor & Francis healthsciences; May-Jun. 2003; pp. 252-266; vol. 19, No. 3; Taylor & Francis Ltd.
Lin, Yi-Hsin; "Electrically Tunable Wettability of Liquid Crystal/Polymer Composite Films"; Optics Express; bearing a date of Oct. 27, 2008; pp. 17591-17598; vol. 16, No. 22; OSA.

(56) References Cited

OTHER PUBLICATIONS

Masteikova, Ruta et al.; "Stimuli-Sensitive Hydrogels in Controlled and Sustained Drug Delivery"; Medicina; 2003; pp. 19-24; vol. 39, No. 2.

McKenna, Susan M. et al.; "The Inhibition of Bacterial Growth by Hypochlorous Acid"; Biochemistry; 1988; pp. 685-692; vol. 254.

Nejat, Farideh et al.; "Original Article: A Randomized Trial of Ceftriaxone Versus Trimethoprimsulfamethoxazole to Prevent Ventriculoperitoneal Shunt Infection"; Journal of Microbiology, Immunology and Infection; 2008; pp. 112-117; vol. 41; Journal of Microbiology, Immunology and Infection.

Ng, P C; "Review: Diagnostic Markers of Infection in Neonates"; Arch Dis Child Fetal Neonatal Ed; 2004; pp. F229-F235; vol. 89; located at: www.archdischild.com.

Okada, Ayako et al.; "Inhibition of Biofilm Formation Using Newly Developed Coating Materials with Self-Cleaning Properties"; Dental Materials Journal; 2008; pp. 565-572; vol. 27, No. 4.

Piper, Kerryl E. et al.; "MIST Ultrasound Therapy Device Removal of In Vitro Bacterial Biofilms"; Mayo Clinic.

Rathmell, James P. et al.; "Infectious Risks of Chronic Pain Treatments: Injection Therapy, Surgical Implants, and Intradiscal Techniques"; Regional Anesthesia and Pain Medicine; 2006; pp. 346-352; vol. 31, No. 4.

Rediske, Andrea M. et al.; "Pulsed Ultrasound Enhances the Killing of *Escherichia coli* Biofilms by Aminoglycoside Antibiotics In Vivo"; Antimicrobial Agents and Chemotherapy; Mar. 2000; pp. 771-772; vol. 44, No. 3; American Society for Microbiology; downloaded on Aug. 24, 2009.

Reid, Marvin et al.; "The Acute-Phase Protein Response to Infection in Edematous and Nonedematous Protein-Energy Malnutrition"; The American Journal of Clinical Nutrition; 2002; pp. 1409-1415; vol. 76; American Society for Clinical Nutrition.

Roti Roti, Joseph L.; "Review: Cellular Responses to Hyperthermia (40-46°C.): Cell Killing and Molecular Events"; Informa healthcare; Feb. 2008; pp. 3-15; vol. 24, No. 1; Informa UK Ltd.

Seehusen, Dean A. et al.; "Cerebrospinal Fluid Analysis"; American Family Physician; bearing a date of Sep. 15, 2003; pp. 1103-1108; vol. 68, No. 6; located at: www.aafg.org/afp.

Setroikromo, R.; "Heat Shock Proteins and Bcl-2 Expression and Function in Relation to the Differential Hyperthermic Sensitivity between Leukemic and Normal Hematopoietic Cells"; Cell Stress & Chaperones; 2007; pp. 320-330; vol. 12, No. 4; Cell Stress Society International.

"SilvaSorb® Targeted Antimicrobial Protection"; Medline; 2005; 16 pages; Medline Industries Inc.; located at www.medline.com.

Sodja, Caroline; "Splenic T Lymphocytes Die Preferentially During Heat-Induced Apoptosis: NuMA Reorganization as a Marker"; Journal of Cell Science; 1998; pp. 2305-2313; vol. 111; The Company of Biologists Limited.

Stankiewicz, Adam R.; "Hsp70 Inhibits Heat-Induced Apoptosis Upstream of Mitochondria by Preventing Bax Translocation"; The Journal of Biological Chemistry; Bearing a date of Nov. 18, 2005; pp. 38729-38739; vol. 280, No. 46; The American Society for Biochemistry and Molecular Biology, Inc.

"Study E: Comparison of the Moisture Uptake and Retention Properties of Biopatch® and SilvaSorb Site®"; 2 pages.

Tuteja, Anish et al.; "Robust Omniphobic Surfaces"; PNAS; bearing a date of Nov. 25, 2008; pp. 18200-18205; vol. 105, No. 47; The National Academy of Sciences of the USA.

Wang, Shutao; "Review: Photoresponsive Surfaces with Controllable Wettability"; Journal of Photochemistry and Photobiology C: Photochemistry Review, Science Direct; 2007; pp. 18-29; vol. 8; Elsevier B.V.

Wang, Zhe et al.; "APD: The Antimicrobial Peptide Database"; Nucleic Acids Research; 2004; pp. D590-D592; vol. 32; Oxford University Press.

Watson, Mark A.; "Review: Clinical Utility of Biochemical Analysis of Cerebrospinal Fluid"; Clinical Chemistry; 1995; pp. 343-360; vol. 41, No. 3.

Wentworth, Jr., Paul et al.; "Reports: Evidence for Antibody-Catalyzed Ozone Formation in Bacterial Killing and Inflammation"; Science AAAS; 2002; pp. 2195-2199; vol. 298; downloaded on Jul. 14, 2009; located at: www.sciencemag.org.

Zhong, Yinghui et al.; "Review: Biomaterials for the Central Nervous System"; Journal of the Royal Society Interface; 2008; pp. 957-975; vol. 5; The Royal Society.

PCT International Search Report; International App. No. PCT/US11/01883; May 3, 2012; pp. 1-5.

PCT International Search Report; International App. No. PCT/US10/00579; May 3, 2010; pp. 1-2.

PCT International Search Report; International App. No. PCT/US09/06393; May 13, 2010; pp. 1-4.

McCarthy et al.; "Steroid Modulation of Astrocytes in the Neonatal Brain: Implications for Adult Reproductive Function"; Biology of Reproduction; bearing a date of Apr. 5, 2002; pp. 691-698; vol. 67; Society for the Study of Reproduction, Inc.

Dienel et al.; Astrocyte activation in vivo during graded photic stimulation; Journal of Neurochemistry; bearing a date of 2007; pp. 1506-1522; vol. 103; International Society for Neurochemistry.

Dubinsky et al.; "High-Intensity Focused Ultrasound: Current Potential and Oncologic Applications"; Ultrasound Imaging-Review, AJR; bearing a date of Jan. 2008; pp. 191-199; vol. 190; American Roentgen Ray Society.

Gavrieli et al.; "Identification of Programmed Cell Death in situ via Specific Labeling of Nuclear DNA Fragmentation"; The Journal of Cell Biology; bearing a date of Nov. 1992; pp. 493-501; vol. 119, No. 3; The Rockefeller University Press; located at: http://jcb.rupress.org/.

Harmon et ai.; "Cell Death Induced in a Murine Mastocytoma by 42-47°C. Heating in vitro: Evidence that the Form of Death Changes From Apoptosis to Necrosis Above a Critical Heat Load"; Int. J. Radiat. Biol., Rights Links; 1990; pp. 845-858; vol. 58, No. 5; Taylor & Francis Ltd.

Khan et al.; "The Effect of Hyperthermia on the Induction of Cell Death in Brain, Testis, and Thymus of the Adult and Developing Rat"; Cell Stress & Chaperones; 2002; pp. 73-90; vol. 7, No. 1; Cell Stress Society International.

McDannold et al.; "Microbubble Contrast Agent with Focused Ultrasound to Create Brain Lesions at Low Power Levels: MR Imaging and Histologic Study in Rabbits[1]": Original Research, Experimental Studies, Radiology; bearing a date of Oct. 2006; pp. 95-106; vol. 241, No. 1; RSNA.

Shellman et al.; "Hyperthermia Induces Endoplasmic Reticulum-Mediated Apoptosis in Melanoma and Non-Melanoma Skin Cancer Cells" Original Article, Journal of Investigative Dermatology; 2008; pp. 949-956; vol. 128; The Society of Investigative Dermatology; located at: www.jidonline.org.

Somwaru et al.; "Heat Induced Apoptosis of Mouse Meiotic Cells is Suppressed by Ectopic Expression of Testis-Specific Calpastatin"; Journal of Andrology; bearing a date of Jul./Aug. 2004; pp. 506-513; vol. 25, No. 4; American Society of Andrology.

Vykhodtseva et al.; "Induction of Apoptosis in vivo in the Rabbit Brain with Focused Ultrasound and Optison®"; Original Contribution, Ultrasound in Med. & Biol.; 2006; pp. 1923-1929; vol. 32, No. 12; World Federation for Ultrasound in Medicine & Biology.

European Patent Office; Extended European Search Report; App. No. EP 10 74 6554; Apr. 5, 2013 (received by our agent on Apr. 8, 2013); 8 pages (1 cover page, 1 supplementary European search report, 6 European search opinion pages).

European Patent Office; Extended Supplementary European Search Report; Application No. EP 09 83 0731; Dec. 18, 2012; (Received by our associate Dec. 19, 2012) ; pp. 1-3.

Elmore, Susan; "Apoptosis: A Review of Programmed Cell Death"; Toxicol Pathology; Dec. 6, 2007; pp. 495-516 (pp. 1-40 as provided); vol. 35, No. 4; National Institute of Health.

Hashimoto et al.; "$TiO_2$ Photocatalysis: A Historical Overview and Future Prospects"; Japanese Journal of Applied Physics; bearing a date of 2005, published Dec. 8, 2005; pp. 8269-8285; vol. 44, No. 12; The Japan Society of Applied Physics.

(56) References Cited

OTHER PUBLICATIONS

Gal'China et al.; "Electroluminescence Spectra of Ultraviolet Light-Emitting Diodes Based on *p-n*-Heterostructures Coated with Phosphors"; Semiconductors; bearing a date of 2007; pp. 1126-11311; vol. 41, No. 9; Pleiades Publishing Ltd.; ISSN 1063-7826.

Kim et al.; "Realization of p-type ZnO thin films via phosphorus doping and thermal activation of the dopant"; Applied Physics Letters; bearing a date of Jul. 7, 2003; pp. 63-65; vol. 83, No. 1; American Institute of Physics.

Könenkamp et al.; "Ultraviolet Electroluminescence from ZnO/Polymer Heterojunction Light-Emitting Diodes"; Nano Letters; bearing a date of 2005; pp. 2005-2008; vol. 5, No. 10; American Chemical Society.

Li et al.; "Ultraviolet nanophosphors"; Journal of Luminescence; bearing a date of 2007; pp. 345-347; vol. 122-123; Elsevier B.V.

Lim et al.; "UV Electroluminescence Emission from ZnO Light-Emitting Diodes Grown by High-Temperatures Radiofrequencey Sputtering"; Advanced Materials; bearing a date of 2006; pp. 2720-2724; vol. 18; Wiley-VCH Verlag GmbH & Co.

Sun et al.; "Realization of ultraviolet electroluminescence from ZnO homojunction with n-ZnO/p-ZnO:As/GaAs structure"; Applied Physics Letters; bearing a date of 2007; pp. 121128-1-121128-3; vol. 90; American Institute of Physics.

Tang et al.; "Cerium Phosphate Nanotubes: Synthesis, Valence State, and Optical Properties"; Angew. Chem. Int. Ed.; bearing a date of 2005; pp. 576-579; vol. 44; Wiley-VCH Verlag GmbH.

Zhang et al.; "Milliwatt power deep ultraviolet light-emitting diodes over sapphire with emission at 278 nm"; Applied Physics Letters; bearing a date of Dec. 23, 2002; pp. 4910-4912; vol. 81, No. 26; American Institute of Physics.

Dostálek et al.; "Multichannel surface plasmon resonance biosensor with wavelength division multiplexing"; Sensors and Actuators B 108 Chemical; Feb. 5, 2005; pp. 758-764; Elsevier B.V.

Nugaeva et al.; :Micromechanical cantilever array sensors for selective fungal immobilization and fast growth detection; Biosensors & Bioelectronics 21; Mar. 2, 2005; pp. 849-856; Elsevier B.V.

\* cited by examiner

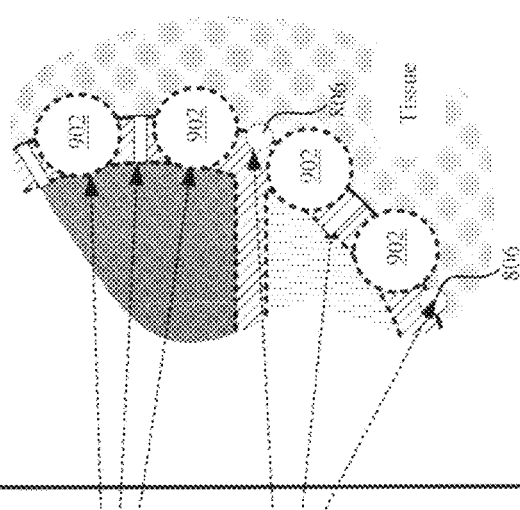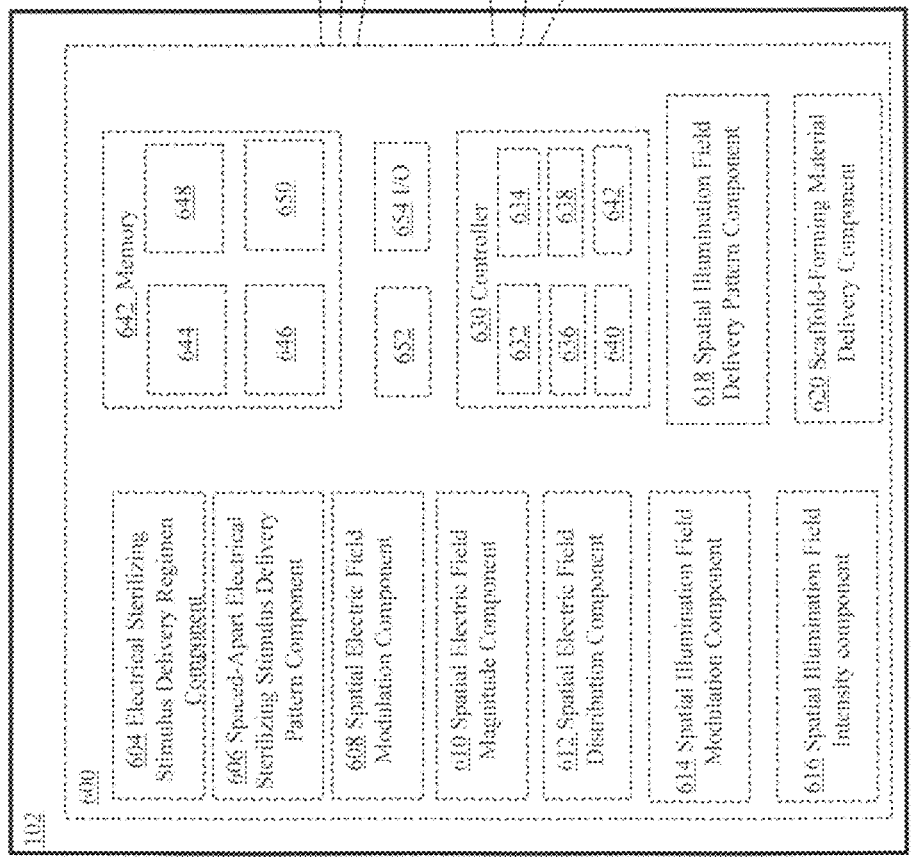
Fig. 6

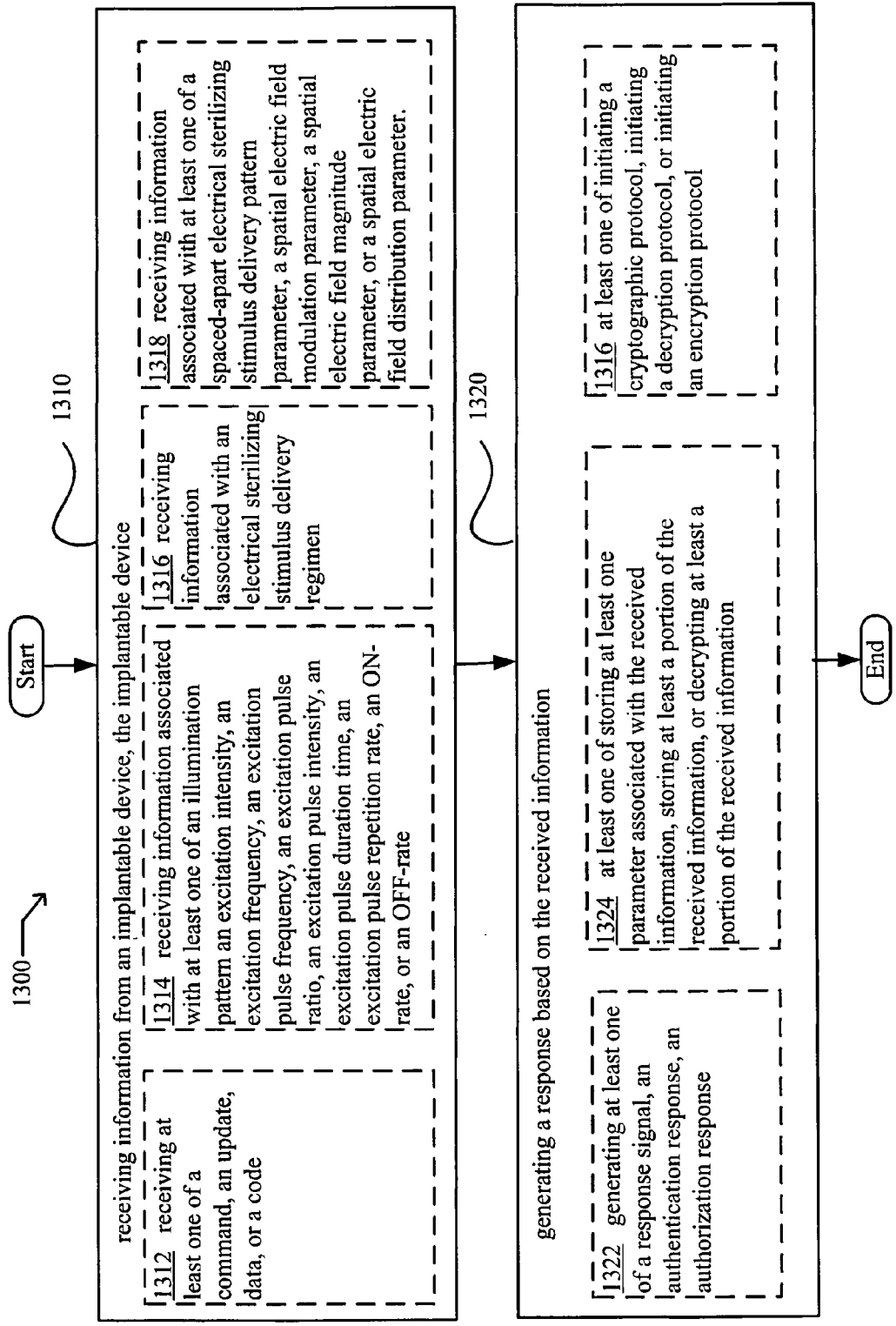

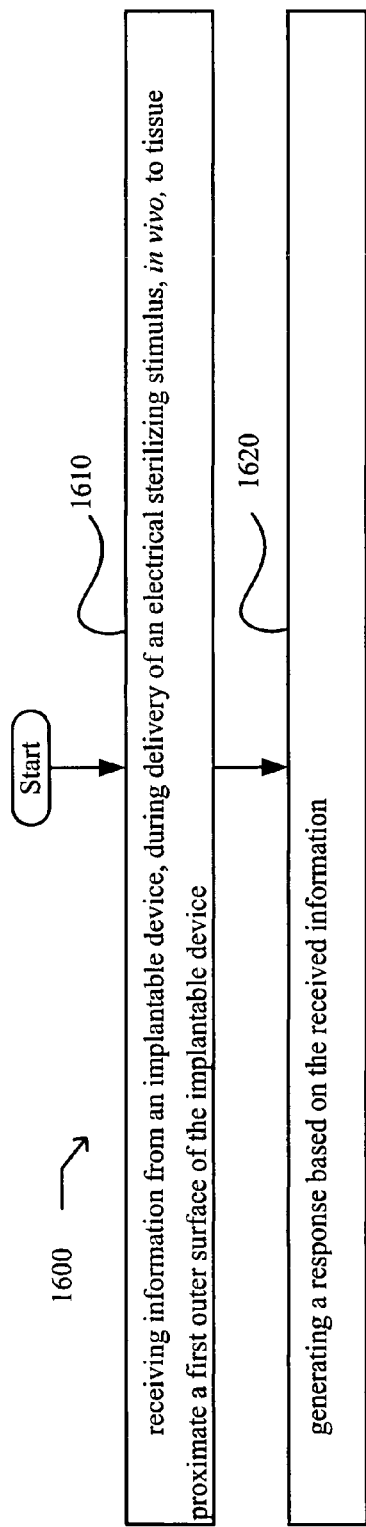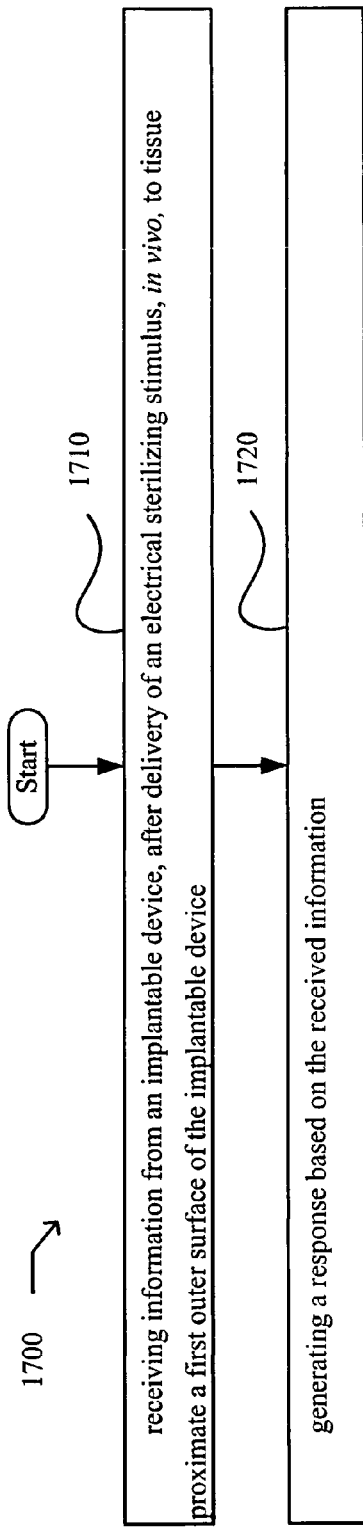

SYSTEM, DEVICES, AND METHODS INCLUDING ACTIVELY-CONTROLLABLE STERILIZING EXCITATION DELIVERY IMPLANTS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 U.S.C. §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

For purposes of the United States Patent and Trademark Office (USPTO) extra-statutory requirements, the present application constitutes a continuation-in-part of U.S. patent application Ser. No. 12/315,881, entitled SYSTEM, DEVICES, AND METHODS INCLUDING STERILIZING EXCITATION DELIVERY IMPLANTS WITH CRYPTOGRAPHIC LOGIC COMPONENTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

The present application is related to U.S. patent application Ser. No. 12/315,885, entitled SYSTEM, DEVICES, AND METHODS INCLUDING ACTIVELY-CONTROLLABLE ELECTROSTATIC AND ELECTROMAGNETIC STERILIZING EXCITATION DELIVERY SYSTEM, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

The present application is related to U.S. patent application Ser. No. 12/315,885, entitled CONTROLLABLE ELECTROSTATIC AND ELECTROMAGNETIC STERILIZING EXCITATION DELIVERY SYSTEMS, DEVICE, AND METHODS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,883, entitled SYSTEM, DEVICES, AND METHODS INCLUDING ACTIVELY-CONTROLLABLE ELECTROMAGNETIC ENERGY-EMITTING DELIVERY SYSTEMS AND ENERGY-ACTIVATEABLE DISINFECTING AGENTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,880, entitled SYSTEM, DEVICES, AND METHODS INCLUDING ACTIVELY-CONTROLLABLE SUPEROXIDE WATER GENERATING SYSTEMS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,884, entitled SYSTEM, DEVICES, AND METHODS INCLUDING ACTIVELY-CONTROLLABLE STERILIZING EXCITATION DELIVERY IMPLANTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/380,553, entitled SYSTEM, DEVICES, AND METHODS INCLUDING ACTIVELY-CONTROLLABLE STERILIZING EXCITATION DELIVERY IMPLANTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood; and Jr.; and Victoria Y. H. Wood as inventors, filed 27 Feb. 2009, which is currently co-pending, or is an application of which a currently co-pending application is entitled to the benefit of the filing date.

The present application is related to U.S. patent application Ser. No. 12/231,676, entitled EVENT-TRIGGERED ULTRAVIOLET LIGHT STERILIZATION OF SURFACES, naming as inventors Roderick A. Hyde; Muriel Y. Ishikawa; Jordin T. Kare; Elizabeth A. Sweeney; Lowell L. Wood; and Jr.; and Victoria Y. H. Wood, filed 3 Sep. 2008.

The USPTO has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, the present disclosure is directed to, among other things, an implantable device. The implantable device includes, but is not limited to, a first outer surface and an actively-controllable excitation component. In an embodiment, the actively-controllable excitation component is configurable to deliver a sterilizing stimulus, in vivo, to tissue proximate the first outer surface of the implantable device. In an embodiment, the actively-controllable excitation component is configured to deliver at least one of an electrical sterilizing stimulus, an electromagnetic sterilizing stimulus, an ultrasonic sterilizing stimulus, or a thermal sterilizing stimulus, in vivo, to tissue proximate tissue proximate the implantable device. The implantable device can include, but is not limited to, a control means. In an embodiment, the control means is operably coupled to the actively-controllable excitation component. In an embodiment, the control means is configurable to control (electrical, electromechanical, software-implemented, firmware-implemented, or other control, or combinations thereof) at least one parameter associated with the delivery of the sterilizing stimulus. The implantable device can include, but is not limited to, a power source. In an embodiment, the power source includes, for example, at least one of a thermoelectric generator, a piezoelectric generator, an electromechanical generator (e.g., a microelectromechanical systems (MEMS) generator), or a biomechanical-energy harvesting generator.

In an aspect, the present disclosure is directed to, among other things, an implantable device. The implantable device includes, but is not limited to, an actively-controllable excitation component configured to deliver a sterilizing stimulus, in vivo, to a target tissue proximate at least a portion of the actively-controllable excitation component. The implantable device can include, but is not limited to, means for controlling at least one sterilizing stimulus delivery parameter associated with the delivery of the sterilizing stimulus, in response to at least one characteristic associated with the tissue proximate the actively-controllable excitation component.

In an aspect, a method includes, but is not limited to, sending information to an implantable device. In an embodiment, the method includes sending information, prior, during, or after delivery of a sterilizing stimulus, in vivo, to tissue proximate a first outer surface of the implantable device. The method can include, but is not limited to, generating a response based on the sent information.

In an aspect, a method includes, but is not limited to, sending information to an implantable device having a first outer surface, an actively-controllable excitation component configured to deliver a sterilizing stimulus, in vivo, to tissue proximate the first outer surface of the implantable device, and a controller operably coupled (e.g., electrically, inductively, capacitively, wirelessly, electromagnetically, magnetically, ultrasonically, optically, and the like) to the actively-controllable excitation component. The method can include, but is not limited to, receiving information from the implantable device.

In an aspect, a method includes, but is not limited to, sending a first information stream to an implantable device. The method can include, but is not limited to, sending a second information stream to the implantable device. In an embodiment, the method can include, but is not limited to, sending a second information stream to the implantable device based on a response to the sent first information stream.

In an aspect, a method includes, but is not limited to, receiving information from an implantable device that includes a first outer surface, an actively-controllable excitation component, and a controller. In an embodiment, the method includes receiving information from an implantable device that includes an actively-controllable excitation component that is configured to deliver a sterilizing stimulus, in vivo, to tissue proximate a first outer surface of the implantable device. In an embodiment, the method includes receiving information from an implantable device that includes a controller that is communicatively coupled to the actively-controllable excitation component.

In an aspect, a method includes, but is not limited to, providing one or more parameters associated with the actively-controlled delivery of a sterilizing stimulus to an implantable device. The method can include, but is not limited to, actively controlling one or more parameters associated with the actively-controlled delivery of a sterilizing stimulus to an implantable device.

In an aspect, a method includes, but is not limited to, providing a first information to an implantable device. The method can include, but is not limited to, obtaining a second information from the implantable device. In an embodiment, the method can include, but is not limited to, obtaining a second information from the implantable device based on a response to the first information. The method can include, but is not limited to, providing information to the implant based on the second information.

In an aspect, a method includes, but is not limited to, receiving information from an implantable device, before delivery of a sterilizing stimulus, in vivo, to tissue proximate a first outer surface of the implantable device. The method can include, but is not limited to, generating a response based on the received information.

In an aspect, a method includes, but is not limited to, receiving information from an implantable device, during delivery of a sterilizing stimulus, in vivo, to tissue proximate a first outer surface of the implantable device. The method can include, but is not limited to, generating a response based on the received information.

In an aspect, a method includes, but is not limited to, receiving information from an implantable device, after delivery of a sterilizing stimulus, in vivo, to tissue proximate a first outer surface of the implantable device. The method can include, but is not limited to, generating a response based on the received information. In an aspect, the present disclosure is directed to, among other things, an implantable device including an sterilizing stimulus providing portion, an actively-controllable excitation component, a controller, and a power source. In an embodiment, the actively-controllable excitation component is configured to deliver a sterilizing stimulus, in vivo, to tissue proximate the sterilizing stimulus providing portion of the implantable device. In an embodiment, the actively-controllable excitation component is configured to deliver at least one of an electrical sterilizing stimulus, an electromagnetic sterilizing stimulus, an ultrasonic sterilizing stimulus, or a thermal sterilizing stimulus, in vivo, to tissue proximate tissue proximate the implantable device. In an embodiment, the controller is communicatively coupled to the actively-controllable excitation component. In an embodiment, the power source is electromagnetically, magnetically, ultrasonically, optically, inductively, electrically, or capacitively-coupled to the actively-controllable excitation component.

In an aspect, the present disclosure is directed to, among other things, an implantable device. The implantable device includes, but is not limited to, a first outer surface and an actively-controllable excitation component configured to concurrently or sequentially deliver a first sterilizing stimulus and a sterilizing stimulus, in vivo, to at least a portion of tissue proximate the first outer surface. In an embodiment, at least one of the first sterilizing stimulus or the second sterilizing stimulus includes a peak emission wavelength in the x-ray, ultraviolet, visible, infrared, near infrared, microwave, or radio frequency spectrum. In an embodiment, the implantable device can include, but is not limited to, a controller communicatively coupled to the actively-controllable excitation component. In an embodiment, the controller is configured to regulate at least one parameter associated with the delivery of the sterilizing stimulus.

In an aspect, a system includes, but is not limited to, an implantable medical device. In an embodiment, the implantable medical device includes a body having at least one outer surface. In an embodiment, the implantable medical device includes one or more energy-emitting elements. In an embodiment, the implantable medical device includes a disinfecting agent assembly including at least one disinfecting active agent reservoir. In an embodiment, the disinfecting agent assembly is configured to deliver at least one energy-activateable disinfecting agent from the at least one disinfecting active agent reservoir to tissue proximate the at least one outer surface of the implantable medical device. The implantable medical device can include, but is not limited to, a controller. In an embodiment, the controller is communicatively coupled to the one or more energy-emitting elements.

In an aspect, a method includes, but is not limited to, treating scar formation post surgery. In an embodiment, the method includes implanting or inserting a surgical implant comprising a photoactivateable steroid composition into a biological subject. In an embodiment, the method includes photoactivating the photoactivateable steroid composition.

In an aspect, a method includes, but is not limited to, treating scar formation post surgery. The method includes photoactivating a photoactivateable steroid composition carried by an implanted surgical implant.

In an aspect, the present disclosure is directed to, among other things, a powered surgical implant. In an embodiment, the powered surgical implant includes, but is not limited to, a plurality of electrodes and a power source. In an embodiment, the plurality of electrodes are configured to energize an aqueous salt composition in the presence of an applied potential. In an embodiment, the power source is electromagnetically, magnetically, ultrasonically, optically, inductively, electrically, or capacitively-coupled to one or more of the plurality of electrodes. In an embodiment, the powered surgical implant can include, but is not limited to, a power source including at least one of a thermoelectric generator, a piezoelectric generator, an electromechanical generator, or a biomechanical-energy harvesting generator. In an embodiment, the powered surgical implant can include, but is not limited to, a control means. In an embodiment, the powered surgical implant can include, but is not limited to, a power source including a generator for harvesting energy generated by a biological subject. In an embodiment, the control means is operably coupled to the plurality of electrodes. In an embodiment, the control means can be adapted to apply a potential across the plurality of electrodes from the power source. In an embodiment, the applied potential is sufficient to produce superoxidized water from an aqueous salt composition proximate the plurality of electrodes, when the powered surgical implant is implanted within a biological subject.

In another aspect, a method includes, but is not limited to, forming an antimicrobial agent, in vivo. The method includes providing an interstitial fluid with a sufficient amount of electrical energy, via an indwelling implant including a plurality of electrodes, to elicit the formation of superoxidized water.

In an aspect, a method includes, but is not limited to, forming an antimicrobial agent, in vivo. The method includes delivering an energy-activateable antimicrobial agent composition to tissue proximate an implanted or inserted surgical implant. In an embodiment, the implanted or inserted surgical implant can include, but is not limited to, at least one antimicrobial agent reservoir. In an embodiment, the antimicrobial agent reservoir is configured to deliver an energy-activateable antimicrobial agent composition to tissue proximate an outer surface of the surgical implant. The implanted or inserted surgical implant can include, but is not limited to, a plurality of electrodes. In an embodiment, the plurality of electrodes are operable to energize an energy-activateable antimicrobial agent composition in the presence of an applied potential. In an embodiment, the method includes applying a sufficient potential to the delivered energy-activateable antimicrobial agent composition and to elicit the formation of superoxide species.

In an aspect, the present disclosure is directed to, among other things, an implantable device. The implantable device can include, but is not limited to, an actively-controllable excitation component, a control means, a sterilizing stimulus, and a cryptographic logic component. In an embodiment, the cryptographic logic component is configured to implement one or more cryptographic processes, one or more cryptographic logics, or combinations thereof. In an embodiment, the actively-controllable excitation component is configured to deliver a sterilizing stimulus, in vivo, to tissue proximate the first outer surface of the implantable device. In an embodiment, the control means is operably coupled to the actively-controllable excitation component, and is configured to control (electrical, electromechanical, software-implemented, firmware-implemented, or other control or combinations thereof) at least one parameter associated with the delivery of the sterilizing stimulus. In an embodiment, the at least one parameter is associated with at least one of a sterilizing stimulus delivery regimen, a spaced-apart sterilizing stimulus delivery pattern, a spatial electric field modulation, a spatial electric field magnitude, or a spatial electric field distribution.

In an aspect, the present disclosure is directed to, among other things, an implantable device. The implantable device can include, but is not limited to, an actively-controllable excitation component configured to deliver an electrical sterilizing stimulus, in vivo, to tissue proximate at least a first outer surface of the implantable device. The implantable device can include, but is not limited to, circuitry for controlling the actively-controllable excitation component. The implantable device can include, but is not limited to, circuitry for implementing one or more cryptographic protocols.

In an aspect, the present disclosure is directed to, among other things, an implantable system. The implantable system can include, but is not limited to, circuitry for actively-controlling an excitation component configurable to deliver a sterilizing stimulus, in vivo, to tissue proximate an implantable device. The implantable system can include, but is not limited to, circuitry for implementing one or more cryptographic protocols.

In an aspect, the present disclosure is directed to, among other things, an implantable device. The implantable device includes, but is not limited to, an actively-controllable excitation component configured to deliver a pulsed thermal sterilizing stimulus, in vivo, to a region proximate a surface of the implantable device. The implantable device can include, but is not limited to, a control means operably coupled to the actively-controllable excitation component. In an embodiment, the control means is configured to regulate at least one of a delivery regimen parameter, a pulsed thermal sterilizing stimulus temporal delivery pattern parameter, a spaced-apart delivery pattern parameter, and a temporal delivery pattern parameter associated with the delivery of the pulsed thermal sterilizing stimulus. In an embodiment, the actively-controllable excitation component is configured to deliver a pulsed thermal sterilizing stimulus including at least a first pulsed waveform segment and a second pulsed waveform segment, the second pulsed waveform segment having at least one of a pulse duration, a pulse frequency, a pulse intensity, a pulse ratio, or a pulse repetition rate different from the first pulsed waveform segment. In an embodiment, the actively-controllable excitation component is configured to deliver a pulsed sterilizing stimulus including at least a first pulsed waveform segment and a second pulsed waveform segment, the second pulsed waveform segment having a spatial profile different from the first pulsed waveform segment.

In an aspect, the present disclosure is directed to, among other things, an indwelling medical implant. The indwelling medical implant includes, but is not limited to, a sensor component configured to perform a real-time comparison of a measurand associated with a biological sample proximate one or more regions of at least one surface of the indwelling implant to stored reference data. The indwelling medical implant can include, but is not limited to, one or more energy emitters configured to emit a pulsed thermal sterilizing stimulus of a character and for a time sufficient to induce apoptosis without substantially inducing necrosis of at least a portion of cells proximate the indwelling medical implant in response to the comparison. In an embodiment, at least one of the one or more energy emitters is configured to emit a pulsed thermal sterilizing stimulus of a character and for a time sufficient to induce apoptosis without substantially inducing necrosis of an infectious agent within a tissue proximate the indwelling medical implant in response to a detected level of an infectious agent.

In an aspect, the present disclosure is directed to, among other things, an implantable system. The implantable system includes, but is not limited to, circuitry for delivering a pulsed thermal sterilizing stimulus, in vivo, to a region proximate a surface of the implantable device, the pulsed thermal sterilizing stimulus of a character and for a time sufficient to induce apoptosis without substantially inducing necrosis of at least a portion of cells within the region proximate the indwelling medical implant. The implantable system can include, but is not limited to, circuitry for regulating at least one parameter associated with the delivery of the pulsed thermal sterilizing stimulus in response to a determination that an infectious agent is present within the region proximate the indwelling medical implant. In an embodiment, the circuitry for delivering the pulsed thermal sterilizing stimulus includes one or more energy emitters configured to deliver a pulsed thermal sterilizing stimulus of a character and for a time sufficient to induce apoptosis without substantially inducing necrosis of the at least a portion of cells proximate the indwelling medical implant.

In an aspect, the present disclosure is directed to, among other things, an in vivo method of treating an infectious agent. The in vivo method of treating an infectious agent can include, but is not limited to, providing a pulsed thermal sterilizing stimulus via one or more energy-emitting components to one or more regions proximate at least one surface of an indwelling implant, the pulsed thermal sterilizing stimulus of a character and for a duration sufficient to induce apoptosis of an infectious agent within the one or more regions proximate the at least one surface of the indwelling implant.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6 is a schematic diagram of a system including an implantable device according to one illustrated embodiment.

FIG. 13 is a flow diagram of a method according to one illustrated embodiment.

FIG. 16 is a flow diagram of a method according to one illustrated embodiment.

FIG. 17 is a flow diagram of a method according to one illustrated embodiment.

DETAILED DESCRIPTION

Figure 1:
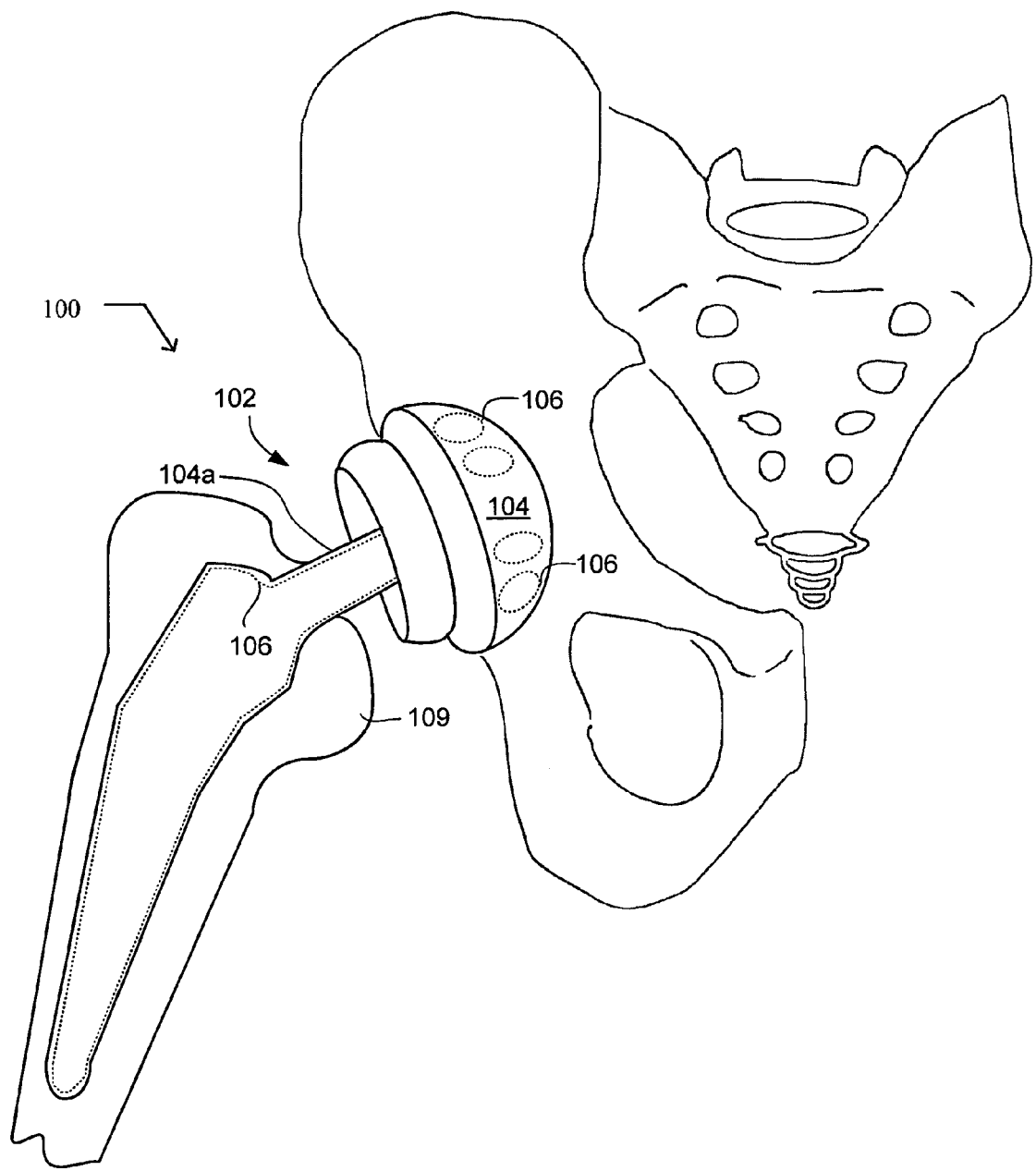
FIG. 1 is a perspective view of a system including an implantable device in the form of a replacement joint, according to one illustrated embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Infections account for one of the many complications associated with surgery and pose tremendous consequences for patients. During an infection, an infecting agent (e.g., fungi, micro-organisms, parasites, pathogens (e.g., viral pathogens, bacterial pathogens, and the like), prions, viroids, viruses, and the like) generally interferes with the normal functioning of a biological subject, and causes, in some cases, chronic wounds, gangrene, loss of an infected tissue, loss of an infected limb, and occasionally death of the biological subject.

Implant-associated infections account for a significant amount of nosocomial infections and despite sterilization and aseptic procedures, remain as a major impediment to medical implants including artificial hearts, artificial joints, artificial prosthetics, breast implants, catheters, contact lens, mechanical heart valves, subcutaneous sensors, vertebral spacers, and the like. Implant-associated infections are often difficult to detect, problematic to cure, and at times expensive to manage. For example, in cases where the infection does not quickly subside, it sometimes becomes necessary to remove the implant.

Implant-associated infections can result from bacterial adhesion and subsequent biofilm formation proximate an implantation site. For example, biofilm-forming microorganisms sometimes colonize implants. Once a biofilm-induced infection takes hold, it can prove difficult to treat.

As a non-limiting example, certain systems, devices, methods, and compositions described herein provide an actively-controllable disinfecting implantable device configured to, for example, treat or prevent an infection (e.g., an implant-associated infection, hematogenous implant-associated infection, and the like), a hematological abnormality, and the like. One non-limiting approach for treating or preventing an infection, a hematological abnormality, and the like includes systems, devices, and methods for administrating a perioperative antibiotic prophylaxis to a patient. Another non-limiting approach includes systems, devices, methods, and compositions for actively-forming an antimicrobial agent, in vivo. Another non-limiting approach includes systems, devices, methods, and compositions for impeding bacterial adherence to the implant surface. Another non-limiting approach includes systems, devices, methods, and compositions for actively-impeding biofilm formation on an implant. Another non-limiting approach includes systems, devices, and methods including coating an implant with active agent compositions having, for example, anti-biofilm activity. Another non-limiting approach includes systems, devices, methods, and compositions for providing an implant with a scaffold-forming material. Another non-limiting approach includes systems, devices, and methods including coating an implant with one or more coatings having self-cleaning properties. Another non-limiting approach includes systems, devices, and methods including an implant with a self-cleaning coating having self-cleaning, and anti-bacterial activity. Another non-limiting approach includes systems, devices, and methods including an implant having one or more self-cleaning surfaces.

Another non-limiting approach includes systems, devices, and methods including an implant configured to provide a sterilizing stimulus (e.g., one or more of an electrical sterilizing stimulus, an electromagnetic sterilizing stimulus, an ultrasonic sterilizing stimulus, or a thermal sterilizing stimulus, or the like) to a biological subject. Another non-limiting approach includes systems, devices, and methods including implants configured to sense an infection. Another non-limiting approach includes systems, devices, and methods for powering an implantable device by harvesting energy from a biological subject having the implantable device implanted within. Yet another non-limiting approach includes systems, devices, and methods configured to treat or reduce the concentration of an infecting agent in the immediate vicinity of an implant.

FIG. 1 shows a system 100 in which one or more methodologies or technologies may be implemented such as, for example, actively, sensing, treating, or preventing an infection (e.g., an implant-associated infection, hematogenous implant-associated infection, and the like), a hematological abnormality, and the like. In an embodiment, the system 100 is configured to, among other things, treat a condition associated with an infection. In an embodiment, the system 100 is configured to, among other things, reduce the concentration of, for example, an infecting agent in the immediate vicinity of an implant. In an embodiment, the system 100 is configured to, among other things, reduce the risk of infection.

The system 100 can include, but is not limited to, one or more implantable devices 102. An implantable device 102 may be configured to, among other things, have numerous configurations. In an embodiment, the implantable device 102 is configured to, among other things, treat or prevent an infection (e.g., an implant-associated infection, hematogenous implant-associated infection, and the like), a hematological abnormality, and the like. In an embodiment, the implantable device 102 is configured to, among other things, form an agent, in vivo. The agent formed in vivo can include an antimicrobial, antibiotic, antibacterial, fungicide, a sanitizer, a disinfectant, an antiseptic, a bactericide, a fungicide, a substances that acts against, for example, a microorganisms, or the like. In an embodiment, the implantable device 102 is configured to, among other things, impede bacterial adherence to the implant surface. In an embodiment, the implantable device 102 is configured to, among other things, impede biofilm formation on an implantable device 102. In an embodiment, the implantable device 102 is configured to, among other things, provide a sterilizing stimulus to a biological subject. In an embodiment, the implantable device 102 is configured to, among other things, detect (e.g., sense, monitor, and the like) an infectious agent (e.g., fungi, microorganisms, parasites, pathogens (e.g., viral pathogens, bacterial pathogens, and the like), prions, viroids, viruses, and the like) present in, for example, tissue proximate the implantable device 102. Pathogenic viruses may include viruses from the Adenoviridae, Picornaviridae, Herpesviridae, Hepadnaviridae, Filoviridae, Flaviviridae, Retroviridae, Orthomyxoviridae, Paramyxoviridae, Papovaviridae, Rhabdoviridae, and Togaviridae family, and the like); Pathogenic bacteria may include *Mycobacterium tuberculosi, Staphylococcus epidermidis, S. aureus, S. warneri*, and the like. In an embodiment, the implantable device 102 is configured to, among other things, detect (e.g., sense, monitor, and the like) an infectious agent marker (e.g., a pathogen marker, a pathogen/microbial counts, an infectious disease marker, and the like). Examples of markers include, but are not limited to, polypeptides, polynucleotides, surface proteins, soluble proteins, polysaccharide coatings, pathogen-associated molecular patterns (PAMPs), single-stranded DNA (ssDNA), double-stranded RNAs (dsRNA), and the like. Further examples of markers include nuclei acid markers indicative of infections (e.g., bacterial or viral infections), inflammatory responses, bacterial replication, cell turnover (e.g., white blood cell turnover), or the like.

In an embodiment, the implantable device 102 is configured to, among other things, treat or reduce the concentration of an infecting agent in the immediate vicinity of the implant. In an embodiment, the implantable device 102 can, among other things, replace a biological structure. For example, in an embodiment, the implantable device 102 is configured to, among other things, replace or function as a missing biological structure. In an embodiment, the implantable device 102 is configured to, among other things, augment a biological function. In an embodiment, the implantable device 102 is configured to, among other things, perform a biological function. In an embodiment, the implantable device 102 is configured to, among other things, permit the movement of fluid from one part or region of the body to another.

In an embodiment, the implantable device 102 is configured to, among other things, detect an altered expression levels of one or more markers indicative of infections (e.g., bacterial or viral infections), inflammatory responses, bacterial replication, cell turnover (e.g., white blood cell turnover). In an embodiment, a method includes, but is not limited to, detecting altered expression levels of one or more markers indicative of infections (e.g., bacterial or viral infections), inflammatory responses, bacterial replication, cell turnover (e.g., white blood cell turnover), or the like.

In an embodiment, the implantable device 102 includes at least an outer surface 104, such as at least a first outer surface 104a, and at least one actively-controllable excitation component 106. In an embodiment, one or more surfaces 104 of the implantable device 102 that contacts a biological subject can comprise a biomedical material such, for example, titanium or biocompatible alloys thereof, silicone, and the like.

In an embodiment, the actively-controllable excitation component 106 is configurable to deliver a sterilizing stimulus, in vivo, to tissue 109 proximate the implantable device 102. In an embodiment, the actively-controllable excitation component 106 is configured to deliver one or more electrical energy sterilizing stimuli, electromagnetic energy sterilizing stimuli, thermal energy sterilizing stimuli, ultrasonic energy sterilizing stimuli, or the like, or combinations thereof. In an embodiment, the actively-controllable excitation component 106 is configured to concurrently or sequentially deliver one or more electrical energy sterilizing stimuli, electromagnetic energy sterilizing stimuli, thermal energy sterilizing stimuli, ultrasonic energy sterilizing stimuli, or the like, or combinations thereof. In an embodiment, the actively-controllable excitation component 106 is configured to deliver a sterilizing stimulus, in vivo, to at least a portion of tissue 109 proximate the implantable device 102. In an embodiment, the actively-controllable excitation component 106 is configured to deliver a sterilizing stimulus of a character and for a time sufficient to induce poration (e.g., electroporation) of a plasma membrane in at least a portion of cells of the tissue 109 proximate the implantable device 102. In an embodiment, the actively-controllable excitation component 106 is configured to deliver a sterilizing stimulus of a character and for a time sufficient to induce pore formation in a plasma membrane of at least a portion of infecting agents proximal to implantable device 102. In an embodiment, the actively-controllable excitation component 106 is configured to deliver a sterilizing stimulus of a character and for a time sufficient to induce pore formation in a plasma membrane in at least a portion of cells of the tissue 109 proximate the implantable device 102.

In an embodiment, the actively-controllable excitation component 106 is configured to deliver a sterilizing stimulus of a character and for a time sufficient to induce poration of a plasma membrane in at least a portion of cells of the tissue proximate a first outer surface 104 of the implantable device 102. In an embodiment, the actively-controllable excitation component 106 is configured to deliver a sterilizing stimulus of a character and for a time sufficient to generate a potential of greater than about 650 millivolts (mV) in a region of the tissue proximate the implantable device 102. In an embodiment, the actively-controllable excitation component 106 is configured to deliver a sterilizing stimulus of a character and for a time sufficient to generate a potential of greater than about 800 millivolts (mV) in a region of the tissue 109 proximate the implantable device 102. In an embodiment, the actively-controllable excitation component 106 is configured to deliver a sterilizing stimulus of a character and for a time sufficient to generate a potential of greater than about 950 mV in a region of the tissue 109 proximate the implantable device 102.

In an embodiment, the actively-controllable excitation component 106 is configured to deliver an electromagnetic stimulus, in vivo, to at least a portion of tissue proximate the first outer surface 104 of the implantable device 102. In an embodiment, the actively-controllable excitation component 106 is configured to deliver a sterilizing stimulus of a character and for a time sufficient to reduce the concentration of at least one infecting agent in at least a portion of tissue proximate the implantable device 102.

In an embodiment, an implantable device 102 includes, but is not limited to, an actively-controllable excitation component 106 configured to deliver a pulsed thermal sterilizing stimulus, in vivo, to a region proximate a surface of the implantable device. In an embodiment, the actively-controllable excitation component 106 is further configured to deliver at least one of an electromagnetic sterilizing stimulus, an electrical sterilizing stimulus, or an ultrasonic sterilizing stimulus. In an embodiment, the actively-controllable excitation component 106 is configured to concurrently or sequentially provide a pulsed thermal sterilizing stimulus and at least one of an electromagnetic sterilizing stimulus, an electrical sterilizing stimulus, or an ultrasonic sterilizing stimulus. In an embodiment, the actively-controllable excitation component 106 is further configured to deliver at least one of a pulsed electromagnetic sterilizing stimulus, a pulsed electrical sterilizing stimulus, or a pulsed ultrasonic sterilizing stimulus.

In an embodiment, the actively-controllable excitation component 106 is configured to concurrently or sequentially provide a pulsed thermal sterilizing stimulus and at least one of an electromagnetic stimulus, an electrical stimulus, an ultrasonic stimulus, a pulsed electromagnetic stimulus, a pulsed electrical stimulus, or a pulsed ultrasonic stimulus. In an embodiment, the actively-controllable excitation component 106 is configured to deliver a spatially-focused pulsed thermal sterilizing stimulus. In an embodiment, the actively-controllable excitation component is configured to deliver a spatially-collimated pulsed thermal sterilizing stimulus. In an embodiment, the actively-controllable excitation component 106 is configured to deliver at least one of a spatially-patterned pulsed thermal sterilizing stimulus or a temporally-patterned pulsed thermal sterilizing stimulus. In an embodiment, the actively-controllable excitation component 106 is configured to concurrently or sequentially provide at least a first pulsed thermal sterilizing stimulus and a second pulsed thermal sterilizing stimulus, the second pulsed thermal sterilizing stimulus having at least one of a duration, a frequency, or an intensity different from the first pulsed thermal sterilizing stimulus. In an embodiment, the actively-controllable excitation component 106 is configured to concurrently or sequentially provide at least a first pulsed thermal sterilizing stimulus and a second pulsed thermal sterilizing stimulus, the second pulsed thermal sterilizing stimulus having a least one of a spatial distribution, a spaced-apart pattern, and a spatial pattern different from the first pulsed thermal sterilizing stimulus. In an embodiment, the actively-controllable excitation component 106 is configured to deliver the pulsed thermal sterilizing stimulus, in vivo, to a tissue proximate the surface of the implantable device.

In an embodiment, the actively-controllable excitation component 106 is configured to deliver the pulsed thermal sterilizing stimulus, in vivo, to an infectious agent proximate the surface of the implantable device. In an embodiment, the actively-controllable excitation component 106 is configured to deliver the pulsed thermal sterilizing stimulus, in vivo, to a one or more spaced-apart regions proximate the surface of the implantable device. In an embodiment, the actively-controllable excitation component 106 is configured to deliver a pulsed thermal sterilizing stimulus of a character and for a duration sufficient to induce a temperature gradient in one or more regions proximate the first outer surface 104.

In an embodiment, the actively-controllable excitation component 106 is configured to deliver a pulsed thermal sterilizing stimulus of a character and for a duration sufficient to temporarily cause local heating of one or more regions proximate the first outer surface 104. In an embodiment, the actively-controllable excitation component 106 is configured to deliver a pulsed thermal sterilizing stimulus in response to a determination that an infectious agent is present proximate the first outer surface 104. In an embodiment, the actively-controllable excitation component 106 is configured to deliver a pulsed thermal sterilizing stimulus in response to a determination that an infectious agent is present within a tissue proximate the first outer surface 104. In an embodiment, the actively-controllable excitation component 106 is configured to deliver a pulsed thermal sterilizing stimulus in response to a comparison between one or more real-time measurands associated with a biological sample proximate the first outer surface 104 and user specific information. In an embodiment, the actively-controllable excitation component 106 is configured to initiate delivery of a pulsed thermal sterilizing stimulus in response to a real-time determination that a detected characteristic associated with a biological sample proximate the first outer surface 104 satisfies one or more threshold criteria. In an embodiment, the actively-controllable excitation component 106 is configured to deliver a pulsed thermal sterilizing stimulus in response to a comparison between a detected characteristic associated with a biological sample proximate the first outer surface 104 and real-time modeling information.

Among implantable devices 102 examples include, but are not limited to, bio-implants, bioactive implants, breast implants, cochlear implants, dental implants, neural implants, orthopedic implants, ocular implants, prostheses, implantable electronic device, implantable medical devices, and the like. Further non-limiting examples of implantable devices 102 include replacements implants (e.g., joint replacements implants such, for example, elbows, hip (an example of which is shown on FIG. 1), knee, shoulder, wrists replacements implants, and the like), subcutaneous drug delivery devices (e.g., implantable pills, drug-eluting stents, and the like), shunts (e.g., cardiac shunts, lumbo-peritoneal shunts, cerebrospinal fluid (CSF) shunts, cerebral shunts, pulmonary shunts, portosystemic shunts, portacaval shunts, and the like), stents (e.g., coronary stents, peripheral vascular stents, prostatic stents, ureteral stents, vascular stents, and the like), biological fluid flow controlling implants, and the like. Further non-limiting examples of implantable devices 102 include artificial hearts, artificial joints, artificial prosthetics, catheters, contact lens, mechanical heart valves, subcutaneous sensors, urinary catheters, vascular catheters, and the like.

In an embodiment, at least a portion of an outer surface of the implantable devices 102 may include one or more coatings, functionalized surfaces, surface treatments, immuno-stimulating coatings, and the like. Among the one or more coatings, functionalized surfaces, surface treatments, immuno-stimulating coatings, and the like, examples include, but are not limited to, polymeric compositions that resist bacterial adhesion, antimicrobial coating, coatings that controllably-release antimicrobial agents, quaternary ammonium silane coatings, chitosan coatings, and the like. Further non-limiting examples of coatings, functionalized surfaces, surface treatments, immuno-stimulating coatings, and the like may be found in, for example, the following documents (the contents of which are incorporated herein by reference):

U.S. Pat. No. 7,348,021 (issued Mar. 25, 2008), U.S. Pat. No. 7,151,139 (issued Dec. 19, 2006), and U.S. Pat. No. 7,143,709 (issued Dec. 5, 2006). In an embodiment, at least a portion of an outer surface of the implantable devices 102 may include one or more self-cleaning coating materials. Examples of self-cleaning coating (e.g., Lotus Effect) materials include, but are not limited to titanium dioxide, super-hydrophobic materials, carbon nanotubes with nanoscopic paraffin coating, or the like. Further examples of self-cleaning (e.g., non fouling) coating materials include, but are not limited to, antimicrobial, and nonfouling zwitterionic polymers, zwitterionic surface forming materials, zwitterionic polymers, poly(carboxybetaine methacrylate) (pCBMA), poly (carboxybetaine acrylic amide) (pCBAA), poly(oligo(ethylene glycol) methyl ether methacrylate) (pOEGMA), poly(N, N-dimethyl-N-(ethoxycarbonylmethyl)-N-[2'-(methacryloyloxy)ethyl]-ammonium bromide), cationic pC8NMA, switchable pCBMA-1 C2, pCBMA-2, and the like. See e.g., WO 2008/083390 (published Jul. 10, 2008) (the contents of which are incorporated herein by reference)

Figure 2:
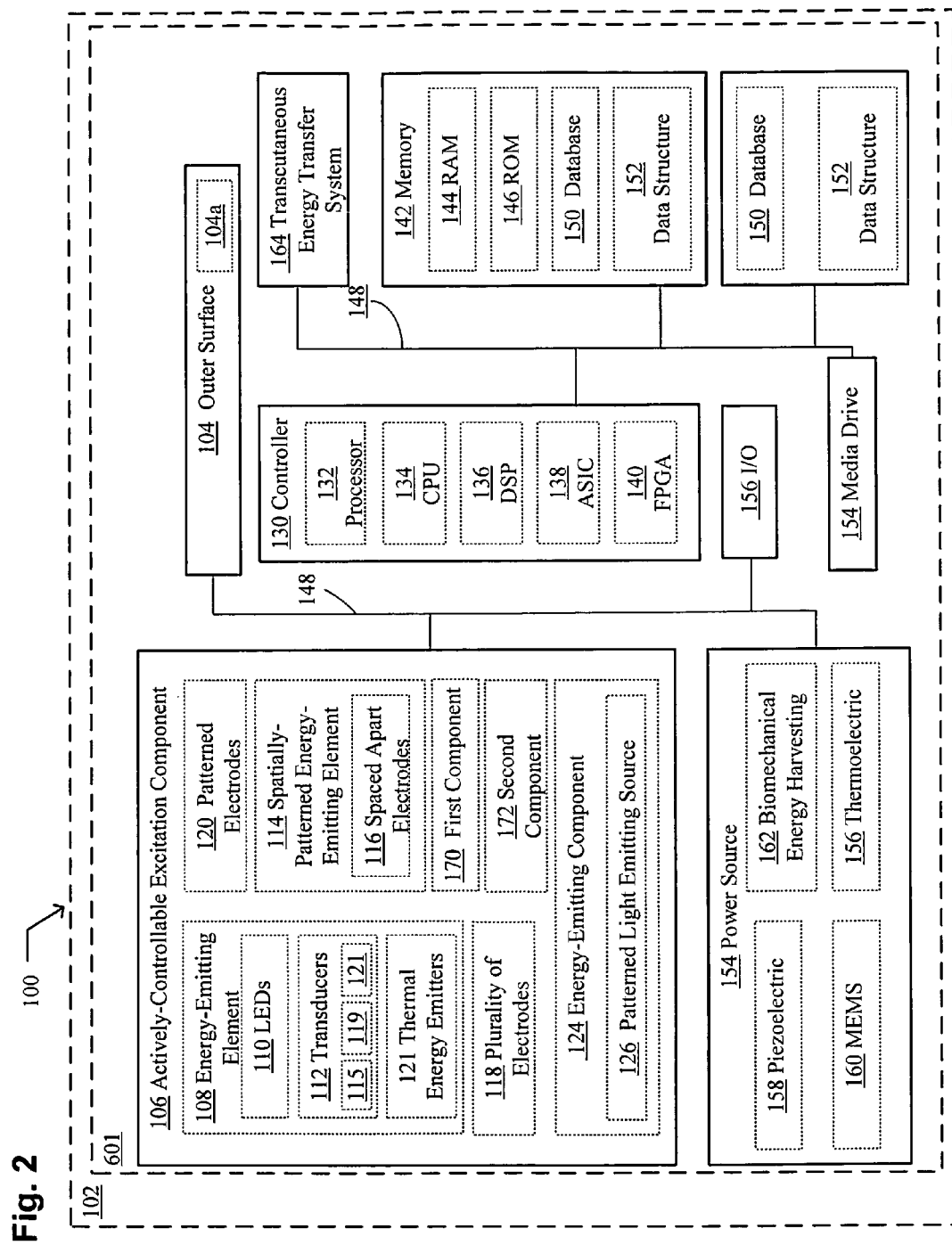
FIG. 2 is a schematic diagram of a system including an implantable device according to one illustrated embodiment.

Referring to FIG. 2, in an embodiment, the implantable device 102 includes, but is not limited to, at least one actively-controllable excitation component 106. The actively-controllable excitation component 106 can include, but is not limited to, one or more energy-emitting elements 108. Among the one or more energy-emitting elements 108 examples include, but are not limited to, electric circuits, electrical conductors, electrodes (e.g., nano- and micro-electrodes, patterned-electrodes, electrode arrays (e.g., multi-electrode arrays, microfabricated multi-electrode arrays, patterned-electrode arrays, and the like), electrocautery electrodes, and the like), cavity resonators, conducting traces, ceramic patterned electrodes, electro-mechanical components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency UV light-emitting diodes, and the like), arc flashlamps, continuous wave bulbs, ultrasound emitting elements, ultrasonic transducers, thermal energy emitting elements, and the like.

In an embodiment, the one or more energy-emitting elements 108 include one or more light-emitting diodes 110. Light-emitting diodes 110 come in a variety of forms and types including, for example, standard, high intensity, super bright, low current types, and the like. Typically, the light-emitting diode's color is determined by the peak wavelength of the light emitted. For example, red light-emitting diodes have a peak emission ranging from about 610 nm to about 660 nm. Examples of light-emitting diode colors include amber, blue, red, green, white, yellow, orange-red, ultraviolet, and the like. Further non-limiting examples of light-emitting diodes include bi-color, tri-color, and the like. Light-emitting diode's emission wavelength may depend on a variety of factors including, for example, the current delivered to the light-emitting diode. The color or peak emission wavelength spectrum of the emitted light may also generally depends on the composition or condition of the semi-conducting material used, and may include, but is not limited to, peak emission wavelengths in the infrared, visible, near-ultraviolet, or ultra-violet spectrum, or combinations thereof.

Light-emitting diodes 110 can be mounted on, for example, but not limited to a surface, a substrate, a portion, or a component of the implantable device 102 using a variety of methods and technologies including, for example, wire bonding, flip chip, controlled collapse chip connection, integrated circuit chip mounting arrangement, and the like. In an embodiment, the light-emitting diodes 110 can be mounted on a surface, substrate, portion, or component of the implantable device 102 using, for example, but not limited to a flip-chip arrangement. A flip-chip is one type of integrated circuit chip mounting arrangement that generally does not require wire bonding between chips. In some embodiments, instead of wire bonding, solder beads or other elements can be positioned or deposited on chip pads such that when the chip is mounted, electrical connections are established between conductive traces carried by circuitry within the system 100.

In an embodiment, the one or more energy-emitting elements 108 include one or more light-emitting diode arrays. In an embodiment, the one or more energy-emitting elements 108 include at least one of a one-dimensional light-emitting diode array, a two-dimensional light-emitting diode array, or a three-dimensional light-emitting diode array.

In an embodiment, the one or more energy-emitting elements 108 include one or more transducers 112 (e.g., ultrasonic transducers, ultrasonic sensors, and the like). In an embodiment, the one or more transducers 112 are configurable to deliver an ultrasonic stimulus (e.g., an ultrasonic sterilizing stimulus, an ultrasonic thermal sterilizing stimulus, or the like) to tissue proximate the implantable device 102. In an embodiment, the one or more transducers 112 are configurable to generate an ultrasonic stimulus to tissue proximate the implantable device 102. In an embodiment, the one or more transducers 112 are configurable to detect an ultrasonic signal. In an embodiment, the one or more transducers 112 are configured to, among other things, transmit and receive ultrasonic waves. In an embodiment, the one or more transducers 112 are configured to, among other things, deliver an ultrasonic stimulus to tissue proximate the implantable device 102. In an embodiment, the one or more transducers 112 are configured to, among other things, deliver an in vivo ultrasonic treatment to a biological subject. In an embodiment, the one or more transducers 112 are configured to, among other things, generate one or more continuous or a pulsed ultrasonic waves, or combinations thereof.

Among transducers 112, examples include acoustic transducers, composite piezoelectric transducers, conformal transducers, flexible transducers, flexible ultrasonic multi-element transducer arrays, flexible ultrasound transducers, immersible ultrasonic transducers, integrated ultrasonic transducers, microfabricated ultrasound transducers, piezoelectric materials (e.g., lead-zirconate-titanate, bismuth titanate, lithium niobate, piezoelectric ceramic films or laminates, sol-gel sprayed piezoelectric ceramic composite films or laminates, piezoelectric crystals, and the like), piezoelectric ring transducers, piezoelectric transducers, ultrasonic sensors, ultrasonic transducers, and the like. In an embodiment, the one or more energy-emitting elements 108 include one or more one-dimensional transducer arrays, two-dimensional transducer arrays, or three-dimensional transducer arrays. The one or more transducers 112 can include a single design where a single piezoelectric component outputs one single waveform at a time, or may be compound where two or more piezoelectric components are utilized in a single transducer 112 or in multiple transducers 112 thereby allowing multiple waveforms to be output sequentially or concurrently.

In an embodiment, the system 100 includes, but is not limited to, electro-mechanical components for transmitting and receiving ultrasonic waves. For example, in an embodiment, the system 100 can include, but is not limited to, one or more waveform generators 115, as well as any associated hardware, software, and the like. In an embodiment, the system 100 includes one or more controllers configured to concurrently or sequentially operate multiple transducers 112. In an embodiment, the system 100 can include, but is not limited to, multiple drive circuits (e.g., one drive circuit for each transducer 112) and may be configured to generate varying waveforms from each coupled transducer 112 (e.g., multiple waveform generators, and the like). The system 100 can include, but is not limited to, an electronic timing controller coupled to an ultrasonic waveform generator 115. In an embodiment, one or more controller are configured to automatically control one or more of a frequency, a duration, a pulse rate, a duty cycle, or the like associate with the ultrasonic energy generated by the one or more transducers 112. In an embodiment, one or more controller are configured to automatically control one or more of a frequency, a duration, a pulse rate, a duty cycle, or the like associate with the ultrasonic energy generated by the one or more transducers 112 based on at least one physiological characteristic of the biological subject, or on at least one characteristic associated with the tissue proximate the implantable device 102.

In an embodiment, the one or more transducers 112 can be communicatively coupled to one or more of the waveform generator 115. In an embodiment, a waveform generators 115 can include, but is not limited to, an oscillator 119 and a pulse generator 121 configured to generate one or more drive signals for causing one or more transducer 112 to ultrasonically vibrate and generate ultrasonic energy. In an embodiment, one or more controller are configured to automatically control least one waveform characteristic (e.g., intensity, frequency, pulse intensity, pulse duration, pulse ratio, pulse repetition rate, and the like) associated with the delivery of one or more ultrasonic energy stimuli. For example, pulsed waves may be characterized by the fraction of time the ultrasound is present over one pulse period. This fraction is called the duty cycle and is calculated by dividing the pulse time ON by the total time of a pulse period (e.g., time ON plus time OFF). In an embodiment, a pulse generator 121 may be configured to electronically generate pulsed periods and non-pulsed (or inactive) periods.

The effects of therapeutic ultrasound on living tissues vary. For example, ultrasound typically has a greater affect on highly organized, structurally rigid tissues such as bone, tendons, ligaments, cartilage, and muscle. Due to their different depths within the body, however, the different tissue types require different ultrasonic frequencies for effective treatment. See e.g., U.S. Publication No. 2007/0249969 (published Oct. 25, 2007) (the contents of which are incorporated herein by reference). Ultrasound may cause increases in tissue relaxation, local blood flow, and scar tissue breakdown. In an embodiment, the effect of the increase in local blood flow can be used to, for example, aid in reducing local swelling and chronic inflammation, as well as promote bone fracture healing. In an embodiment, applying a sufficient ultrasonic energy to tissue infected with, for example, pathogenic bacteria, may lead to a reduction of the pathogenic bacteria in at least a portion of the infected tissue. In an embodiment, applying a sufficient ultrasonic energy to tissue infected with, for example, pathogenic bacteria, in the presence of one or more disinfecting agents may lead to a reduction of the pathogenic bacteria in at least a portion of the infected tissue. In an embodiment, applying a sufficient ultrasonic energy to tissue infected with, for example, pathogenic bacteria, in the presence of one or more disinfecting agents may reduce biofilm viability, as well as actively-impeding biofilm formation on an implant.

In an embodiment, the one or more energy-emitting elements 108 can be implanted within a biological subject. In an embodiment, the one or more energy-emitting elements 108 are configured to apply energy (e.g., electrical energy, electromagnetic energy, thermal energy, ultrasonic energy, or the like, or combinations thereof) to tissue proximate an implantable device 102 to, for example, treat or prevent an infection (e.g., an implant-associated infection, hematogenous implant-associated infection, and the like), a hematological abnormality, and the like. In an embodiment, the one or more energy-emitting elements 108 are configured to apply energy to tissue proximate an implantable device 102 to promote at least one of a tissue healing process, a tissue growing process, a tissue scarring process, or the like. In an embodiment, the one or more energy-emitting elements 108 are configured to apply energy of sufficient strength or duration to tissue proximate an implant to inhibit a tissue scarring process. In an embodiment, the one or more energy-emitting elements 108 are configured to apply energy to tissue proximate an implant to treat, prevent, inhibit, or reduce post-operative adhesion, fibrin sheath formation, or scar tissue formation. In an embodiment, the one or more energy-emitting elements 108 are configured to apply energy to tissue proximate an implantable device 102 to treat, prevent, inhibit, or reduce the presence or concentration of an infecting agent within at least a portion of the tissue proximate the implantable device 102.

The system 100 can include, but is not limited to, at least one spatially-patterned energy-emitting element 114 configured to provide a spatially-patterned sterilizing stimulus to tissue proximate an implantable device 102. The spatially-patterned sterilizing stimulus can take a variety forms, configurations, and geometrical patterns including for example, but not limited to, lines, circles, ellipses, triangles, rectangles, polygons, any regular or irregular geometrical patterns, one-dimensional patterns, two-dimensional patterns, three-dimensional patterns, and the like, and any combination thereof. In an embodiment, the actively-controllable excitation component 106 includes a spatially-patterned energy-emitting element configured to provide a spatially-patterned sterilizing stimulus. In an embodiment, the actively-controllable excitation component 106 includes a spatially-patterned energy-emitting element configured to provide a spatially-patterned sterilizing stimulus, the spatially-patterned energy-emitting element having a plurality of spaced apart electrodes 116.

The actively-controllable excitation component 106 can include, but is not limited to, at least one patterned electrode 120. In an embodiment, the at least one patterned electrode 120 is configured to provide a spatially-patterned sterilizing stimulus. Electrodes forming part of a patterned electrode, such as the at least one patterned electrode 120, can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, and the like, and any combination thereof. Techniques suitable for making patterned electrodes include, but are not limited to, electro-deposition, electro-deposition onto laser-drilled polymer molds, laser cutting and electro-polishing, laser micromachining, surface micro-machining, soft lithography, x-ray lithography, LIGA techniques (e.g., X-ray lithography, electroplating, and molding), conductive paint silk screen techniques, conventional pattering techniques, injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, and the like), complementary-symmetry/metal-oxide semiconductor (CMOS) technology, deep x-ray exposure techniques, and the like.

One or more actively-controllable excitation components 106 can be configured to deliver a pulsed thermal sterilizing stimulus of a character and for a duration sufficient to elevate a temperature of at least a portion of cells proximate the indwelling medical implant. Elevated temperatures or hyperthermia therapy caused by an actively-controllable excitation component 106 in a region including cells and or tissue can induce death of the cells and or tissue through, for example, a process of programmed cell death (apoptosis) or necrosis, depending upon the temperature experienced by the cells and or tissue. For example, hyperthermia therapy between 40° C. and 60° C. can result in disordered cellular metabolism and membrane function and in many instances, cell death. In general, at temperatures below 60° C., hyperthermia is more likely to induce apoptosis in cells without substantially inducing necrosis. At temperatures greater than about 60° C., the likelihood of inducing coagulation necrosis of cells and tissue increases. Relatively small increases in temperature, e.g., 3° C., above the normal functioning temperature of a cell can cause apoptotic cell death. For example, temperatures ranging from 40° C. to 47° C. can induce cell death in a reproducible time and temperature dependent manner in cells normally functioning at 37° C.

Elevating the temperature of a mammalian cell, for example, to 43° C. can cause changes in cellular protein expression and increased apoptosis. In some instances, hyperthermia may be induced by exposure to high intensity focused ultrasound (HIFU). High acoustic intensities associated with HIFU can cause rapid heat generation in cells and tissue due to absorption of the acoustic energy. Using HIFU, the temperature in a region including cells and or tissue can rise very rapidly, inducing thermal stressing of the targeted cells and or tissue which in turn can lead to apoptotic cell death. The degree of thermal stressing of cells may be a function of the character or duration of the energy stimulus delivered to induce a temperature change. For example, rapid heating of cells using HIFU may be advantageous for rapidly attenuating an infectious activity by inducing cell death as opposed to slow increases in temperature to which the cells may become adapted. See, e.g., Somwaru, et al., *J. Androl.* 25:506-513, 2004; Stankiewicz, et al., *J. Biol. Chem.* 280:38729-38739, 2005; Sodja, et al., *J. Cell Sci.* 111:2305-2313, 1998; Setroikromo, et al., *Cell Stress Chaperones* 12:320-330, 2007; Dubinsky, et al., *AJR* 190:191-199, 2008; Lepock. *Int. J. Hyperthermia,* 19:252-266, 2003; Roti Roti *Int. J. Hyperthermia* 24:3-15, 2008; Fuchs, et al., "The Laser's Position in Medicine" pp 187-198 in *Applied Laser Medicine*. Ed. Hans-Peter Berlien, Gerhard J. Muller, Springer-Verlag New York, LLC, 2003; which are all incorporated herein by reference.

In an embodiment, an indwelling medical implant includes 102 a sensor component 902 configured to perform a real-time comparison of a measurand associated with a biological sample proximate one or more regions of at least one surface of the indwelling implant to stored reference data. The indwelling medical implant 102 can include, among other things, one or more energy emitters 108 configured to emit a pulsed thermal sterilizing stimulus of a character and for a time sufficient to induce apoptosis without substantially inducing necrosis of at least a portion of cells proximate the indwelling medical implant 102 in response to the comparison. In an embodiment, at least one of the one or more energy emitters 108 is configured to emit a pulsed thermal sterilizing stimulus of a character and for a time sufficient to induce apoptosis without substantially inducing necrosis of an infectious agent within a tissue proximate the indwelling medical implant 102 in response to a detected level of an infectious agent.

In an embodiment, at least one of the one or more energy emitters 108 is configured to emit a pulsed thermal sterilizing stimulus of a character and for a time sufficient to induce apoptosis without substantially inducing necrosis of a pathogen within a region proximate the indwelling medical implant 102. In an embodiment, at least one of the one or more energy emitters 108 is configured to deliver a pulsed thermal sterilizing stimulus of a character and for a time sufficient to induce thermal poration of a plasma membrane in at least a portion of cells within a tissue proximate the indwelling medical implant 102. In an embodiment, at least of the one or more energy emitters 108 is configured to deliver a pulsed thermal sterilizing stimulus of a character and for a time sufficient to induce poration of a plasma membrane in at least a portion of cells on a surface of the indwelling medical implant 102.

In an embodiment, the one or more energy emitters 108 are operable to emit a sufficient amount of a pulsed thermal sterilizing stimulus to increase the temperature of at least a portion of cells proximate the indwelling medical implant 102 by about 3° C. to about 22° C. In an embodiment, the one or more energy emitters 108 are operable to emit a sufficient amount of a pulsed thermal sterilizing stimulus to increase the temperature of at least a portion of cells proximate the indwelling medical implant 102 by about 3° C. to about 10° C. In an embodiment, the one or more energy emitters 108 are operable to emit a sufficient amount of a pulsed thermal sterilizing stimulus to increase the temperature of at least a portion of cells proximate the indwelling medical implant 102 by about 3° C. to about 4° C. In an embodiment, at least one of the one or more energy emitters 108 is configured to deliver a pulsed thermal sterilizing stimulus of a character and for a duration sufficient to elevate a temperature of at least a portion of cells proximate the indwelling medical implant 102 from about 37° C. to less than about 60° C. In an embodiment, at least one of the one or more energy emitters 108 is configured to deliver a pulsed thermal sterilizing stimulus of a character and for a duration sufficient to elevate a temperature of at least a portion of cells proximate the indwelling medical implant from about 37° C. to less than about 47° C. In an embodiment, at least one of the one or more energy emitters 108 is configured to deliver a pulsed thermal sterilizing stimulus 37° C. of a character and for a duration sufficient to elevate a temperature of at least a portion of cells proximate the indwelling medical implant 102 from about 37° C. to less than about 45° C. In an embodiment, at least one of the one or more energy emitters 108 is configured to deliver a pulsed thermal sterilizing stimulus of a character and for a duration sufficient to elevate a temperature of at least a portion of cells proximate the indwelling medical implant 102 from about 37° C. to less than about 42° C. In an embodiment, least one of the one or more energy emitters 108 is configured to deliver a pulsed thermal sterilizing stimulus of a character and for a duration sufficient to elevate a temperature of at least a portion of cells proximate the indwelling medical implant 102 from about 37° C. to a temperature ranging from greater than about 41° C. to less than about 63° C.

Figure 22:
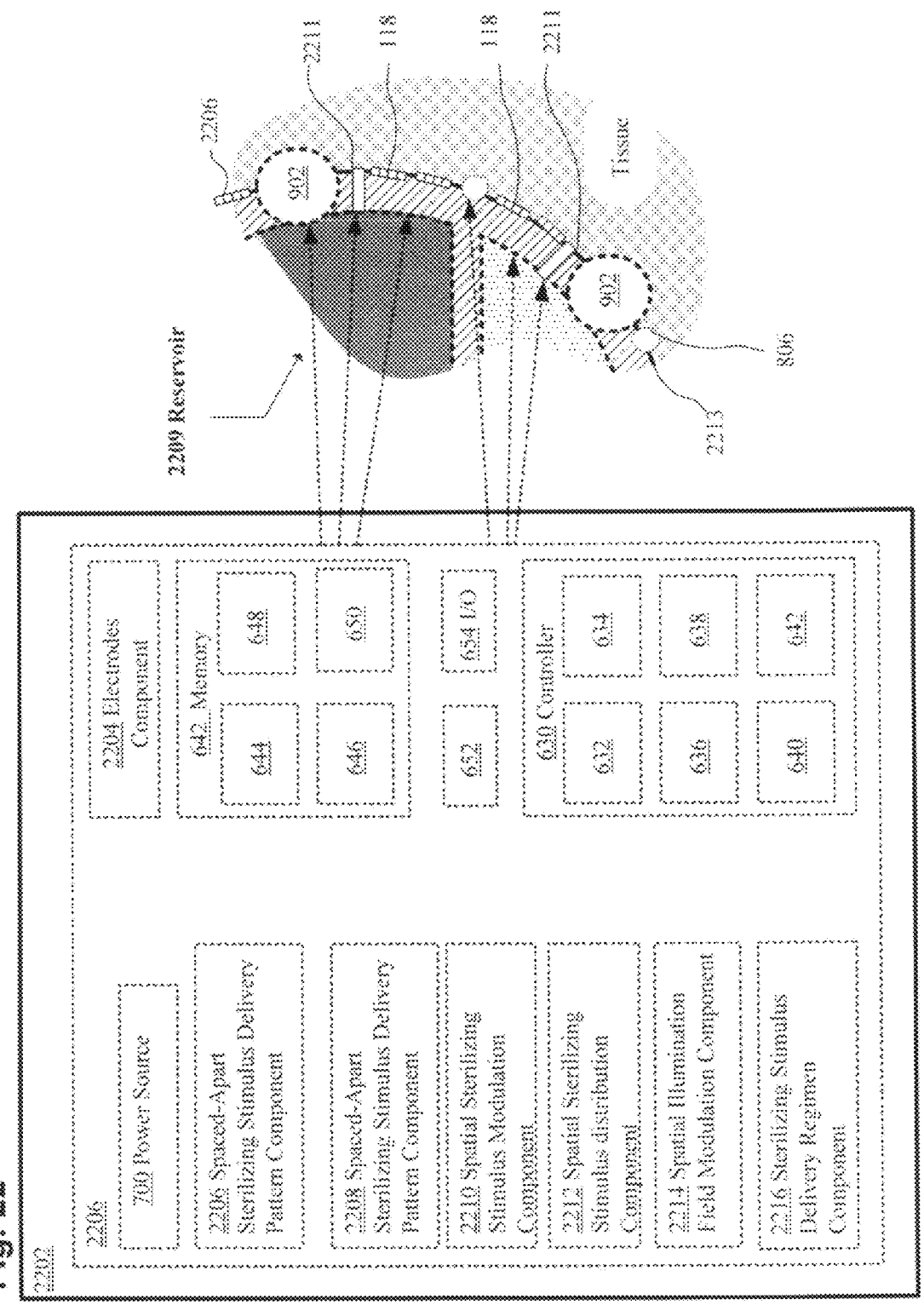
FIG. 22 is a schematic diagram of a system including a powered surgical implant according to one illustrated embodiment.

Referring to FIGS. 2 and 22, in an embodiment, an implantable system 100 includes, but is not limited to, circuitry 2206 for delivering a pulsed thermal sterilizing stimulus, in vivo, to a region proximate a surface of an implantable device 102, the pulsed thermal sterilizing stimulus of a character and for a time sufficient to induce apoptosis without substantially inducing necrosis of at least a portion of cells within the region proximate the indwelling medical implant. The implantable system 100 can include, but is not limited to, circuitry 601 for regulating at least one parameter associated with the delivery of the pulsed thermal sterilizing stimulus in response to a determination that an infectious agent is present within the region proximate the indwelling medical implant. In an embodiment, the circuitry 2206 for delivering the pulsed thermal sterilizing stimulus includes one or more energy emitters 108 configured to deliver a pulsed thermal sterilizing stimulus of a character and for a time sufficient to induce apoptosis without substantially inducing necrosis of the at least a portion of cells proximate the implantable device 102.

In an embodiment, the circuitry 2206 for delivering the pulsed thermal sterilizing stimulus includes an actively-controllable excitation component configured to deliver a spatially-focused pulsed thermal sterilizing stimulus. In an embodiment, the circuitry 2206 for delivering the pulsed thermal sterilizing stimulus includes an actively-controllable excitation component configured to deliver a spatially-collimated pulsed thermal sterilizing stimulus. In an embodiment, the circuitry 2206 for delivering the pulsed thermal sterilizing stimulus includes an actively-controllable excitation component configured to deliver at least one of a spatially-patterned pulsed thermal sterilizing stimulus or a temporally-patterned pulsed thermal sterilizing stimulus. In an embodiment, the circuitry 601 for regulating the at least one parameter associated with the delivery of the pulsed thermal sterilizing stimulus is operably coupled to the circuitry 2206 for delivering the pulsed thermal sterilizing stimulus and configured to control at least one of a pulsed thermal sterilizing stimulus delivery regimen parameter, a pulsed thermal sterilizing stimulus temporal delivery pattern parameter, a spaced-apart pulsed thermal sterilizing stimulus delivery pattern parameter, or a pulsed thermal sterilizing stimulus temporal delivery pattern parameter.

In an embodiment, the circuitry 601 for regulating the at least one parameter associated with the delivery of the pulsed thermal sterilizing stimulus is configured to control at least one of an excitation intensity, an excitation frequency, an excitation pulse frequency, an excitation pulse ratio, an excitation pulse intensity, an excitation pulse duration time, or an excitation pulse repetition rate associated with the delivery of the pulsed thermal sterilizing stimulus. In an embodiment, the circuitry 601 for regulating the at least one parameter associated with the delivery of the pulsed thermal sterilizing stimulus is configured to control at least one of a pulsed thermal sterilizing stimulus delivery regimen parameter or a spaced-apart pulsed thermal sterilizing stimulus delivery pattern parameter associated with the delivery of the pulsed thermal sterilizing stimulus. In an embodiment, the circuitry 601 for regulating the at least one parameter associated with the delivery of the pulsed thermal sterilizing stimulus is configured to control at least one of a spatial electric field modulation parameter, a spatial electric field magnitude parameter, a spatial electric field distribution parameter, an ON-rate, or an OFF-rate associated with the delivery of the pulsed thermal sterilizing stimulus.

Figure 3A:
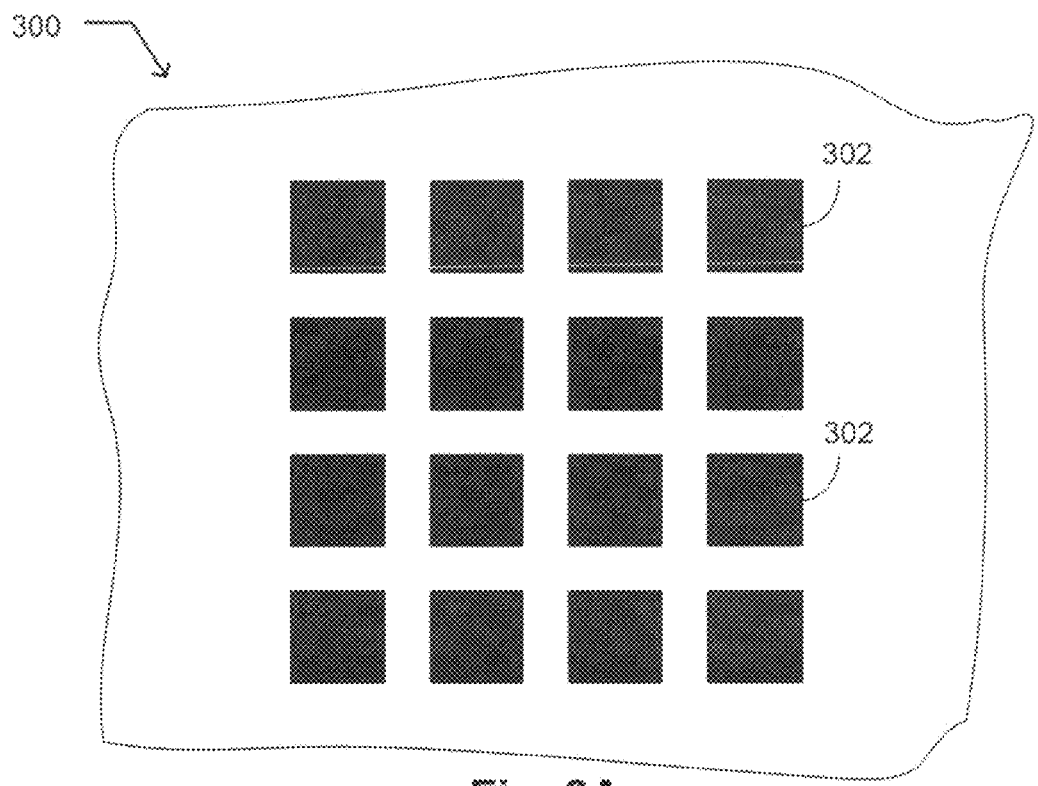
FIG. 3A is a top plan view of one or more energy-emitting elements in the form of a patterned electrode, according to one illustrated embodiment.
Figure 3B:
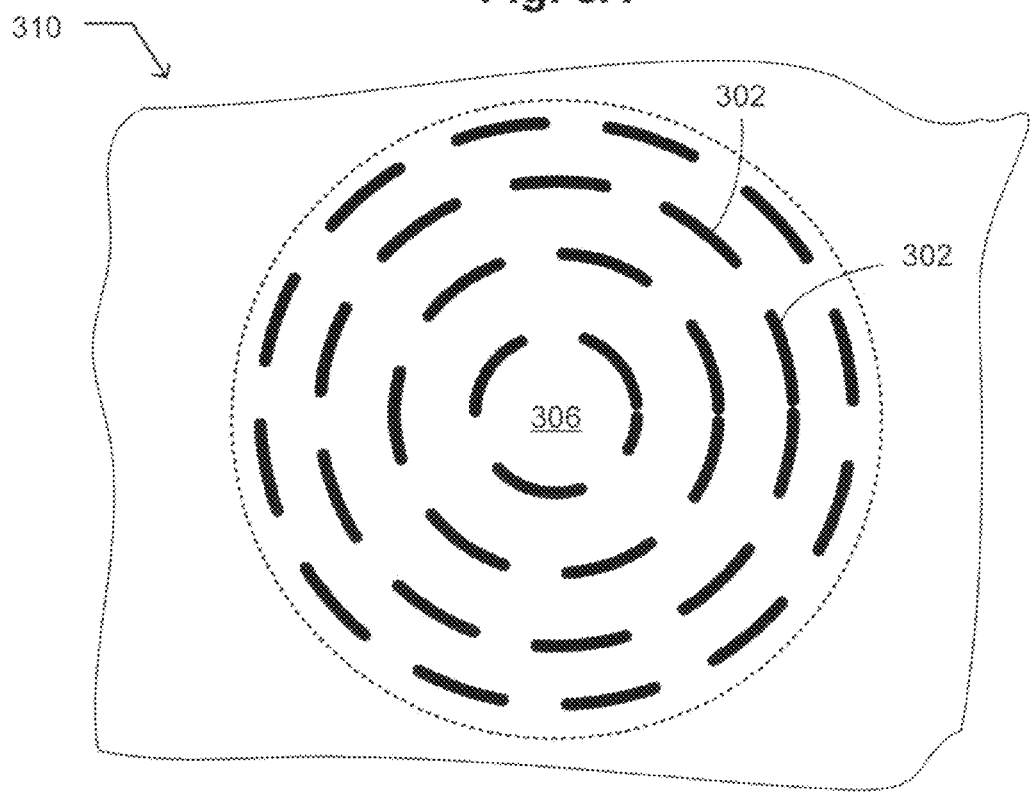
FIG. 3B is a top plan view of one or more energy-emitting elements in the form of a patterned electrode, according to one illustrated embodiment.

Referring to FIGS. 3A and 3B, in an embodiment, a patterned electrode 300 can include, but is not limited to, one or more conductive traces 302 that are deposited, etched, or otherwise applied to a substrate to form one or more patterned electrodes. For example, lithographic techniques can be use to form a conductive trace layout 310, onto a surface of a substrate 306. The lithographic process for forming the conductive trace layouts 310 can include for example, but not limited to, applying a resist film (e.g., spin-coating a photoresist film) onto the substrate, exposing the resist with an image of a circuit layout (e.g., the geometric pattern of one or more conductive traces), heat treating the resist, developing the resist, transferring the layout onto the substrate, and removing the remaining resist. Transferring the layout onto the substrate 306 can include, but is not limited to, using techniques like subtractive transfer, etching, additive transfer, selective deposition, impurity doping, ion implantation, and the like.

Figure 4A:
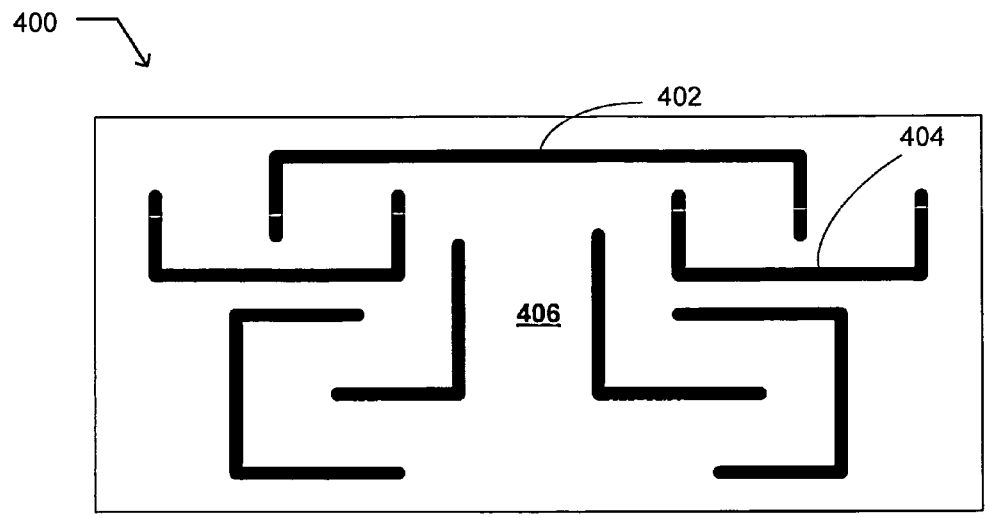
FIG. 4A is a top plan view of one or more energy-emitting elements in the form of a patterned electrode, according to one illustrated embodiment.
Figure 4B:
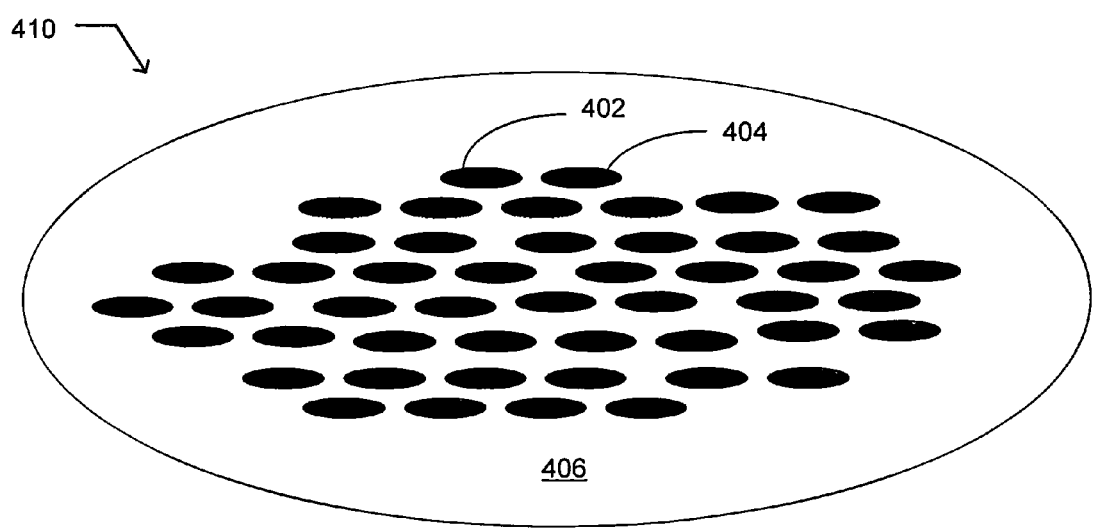
FIG. 4B is a top plan view of one or more energy-emitting elements in the form of a patterned electrode, according to one illustrated embodiment.

Patterned electrodes 300 can be sized and shaped to provide a spatially-patterned sterilizing stimulus to, for example, a region proximate an implantable device 102. In an embodiment, the spatially-patterned sterilizing stimulus is adapted to provide a voltage across at least a portion of cells of tissue proximate an outer surface of the implantable device 102. In an embodiment, the spatially-patterned sterilizing stimulus is adapted to provide a voltage across at least a portion of tissue proximate the implantable device 102, and to induce pore formation in a plasma membrane of at least a portion of infecting agents within the region proximate the implantable device 102. In an embodiment, the voltage is of sufficient strength or duration to exceed a nominal dielectric strength of at least one cell plasma membrane. Referring to FIGS. 4A and 4B, in an embodiment, the patterned electrodes 400, 410 can include, but are not limited to, two or more electrodes 402, 404 forming a pattern. In an embodiment, the patterned electrodes 400 can include two or more electrodes 402, 404 separated by an insulating material 406.

With continued reference to FIG. 2, the system 100 can include, but is not limited to, one or more controllers 130 such as a processor (e.g., a microprocessor) 132, a central processing unit (CPU) 134, a digital signal processor (DSP) 136, an application-specific integrated circuit (ASIC) 138, a field programmable gate array (FPGA) 140, and the like, and any combinations thereof, and may include discrete digital or analog circuit elements or electronics, or combinations thereof. In an embodiment, the implantable device 102 can, for example, wirelessly coupled to a controller 130 that communicates with the implantable device 102 via wireless communication. Examples of wireless communication include for example, but not limited to, optical connections, ultraviolet connections, infrared, BLUETOOTH®, Internet connections, network connections, and the like.

In an embodiment, the system 100 includes at least one controller 130 operably coupled to the actively-controllable excitation component 106. In an embodiment, the at least one controller 130 is configured to control at least one parameter associated with the delivery of the sterilizing stimulus. In an embodiment, the at least one controller 130 is configured to control at least one of a duration time, a delivery location, or a spatial-pattern stimulation configuration associated with the delivery of the sterilizing stimulus. In an embodiment, the at least one controller 130 is configured to control at least one of an excitation intensity, an excitation frequency, an excitation pulse frequency, an excitation pulse ratio, an excitation pulse intensity, an excitation pulse duration time, an excitation pulse repetition rate, an ON-rate, or an OFF-rate.

The system 100 can include, but is not limited to, one or more memories 142 that, for example, store instructions or data, for example, volatile memory (e.g., Random Access Memory (RAM) 144, Dynamic Random Access Memory (DRAM), and the like) non-volatile memory (e.g., Read-Only Memory (ROM) 146, Electrically Erasable Programmable Read-Only Memory (EEPROM), Compact Disc Read-Only Memory (CD-ROM), and the like), persistent memory, and the like. Further non-limiting examples of one or more memories 142 include Erasable Programmable Read-Only Memory (EPROM), flash memory, and the like. The one or more memories can be coupled to, for example, one or more controllers 130 by one or more instruction, data, or power buses 148.

The system 100 can include, but is not limited to, one or more databases 150. In an embodiment, a database 150 can include, but is not limited to, at least one of inflammation indication parameter data, infection indication parameter data, diseased tissue indication parameter data, or the like. In an embodiment, a database 150 can include, but is not limited to, at least one of absorption coefficient data, extinction coefficient data, scattering coefficient data, or the like. In an embodiment, a database 150 can include, but is not limited to, at least one of stored reference data such as infection marker data, inflammation marker data, infective stress marker data, sepsis marker data, systemic inflammatory response syndrome (SIRS) marker data, or the like. In an embodiment, a database 150 can include, but is not limited to, information associated with a disease state of a biological subject. In an embodiment, a database 150 can include, but is not limited to, measurement data.

Inflammation is a complex biological response to insults that arise from, for example, chemical, traumatic, or infectious stimuli. It is a protective attempt by an organism to isolate and eradicate the injurious stimuli as well as to initiate the process of tissue repair. The events in the inflammatory response are initiated by a complex series of interactions involving inflammatory mediators, including those released by immune cells and other cells of the body. Histamines and eicosanoids such as prostaglandins and leukotrienes act on blood vessels at the site of infection to localize blood flow, concentrate plasma proteins, and increase capillary permeability. Chemotactic factors, including certain eicosanoids, complement, and especially cytokines known as chemokines, attract particular leukocytes to the site of infection. Other inflammatory mediators, including some released by the summoned leukocytes, function locally and systemically to promote the inflammatory response. Platelet activating factors and related mediators function in clotting, which aids in localization and can trap pathogens, Certain cytokines, interleukins and TNF, induce further trafficking and extravasation of immune cells, hematopoiesis, fever, and production of acute phase proteins. Once signaled, some cells and/or their products directly affect the offending pathogens, for example by inducing phagocytosis of bacteria or, as with interferon, providing antiviral effects by shutting down protein synthesis in the host cells. Oxygen radicals, cytotoxic factors, and growth factors may also be released to fight pathogen infection and/or to facilitate tissue healing. This cascade of biochemical events propagates and matures the inflammatory response, involving the local vascular system, the immune system, and various cells within the injured tissue. Under normal circumstances, through a complex process of mediator-regulated pro-inflammatory and anti-inflammatory signals, the inflammatory response eventually resolves itself and subsides. For example, the transient and localized swelling associated with a cut is an example of an acute inflammatory response. However, in certain cases resolution does not occur as expected. Prolonged inflammation, known as chronic inflammation, leads to a progressive shift in the type of cells present at the site of inflammation and is characterized by simultaneous destruction and healing of the tissue from the inflammatory process, as directed by certain mediators. Rheumatoid arthritis is an example of a disease associated with persistent and chronic inflammation.

In an embodiment, the system 100 is configured to compare an input associated with at least one characteristic associated with a tissue proximate an implantable device 102 to a database 150 of stored reference values, and to generate a response based in part on the comparison. In an embodiment, the system 100 is configured to compare an input associated with at least one physiological characteristic associated with a biological subject to a database 150 of stored reference values, and to generate a response based in part on the comparison.

The system 100 can include, but is not limited to, one or more data structures 152. In an embodiment, a data structure 152 can include, but is not limited to, at least one of information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, a pH level, or the like. The system 100 can include, but is not limited to, at least one of inflammation indication parameter data, infection indication parameter data, diseased tissue indication parameter data, or the like configured as a data structure 152. In an embodiment, a data structure 152 can include, but is not limited to, information associated with least one parameter associated with a cytokine plasma concentration or an acute phase protein plasma concentration. In an embodiment, a data structure 152 can include, but is not limited to, information associated with a disease state of a biological subject. In an embodiment, a data structure 152 can include, but is not limited to, measurement data.

In an embodiment, the system 100 is configured to compare an input associated with at least one characteristic associated with a tissue proximate an implantable device 102 to a data structure 152 including reference values, and to generate a response based in part on the comparison. In an embodiment, the system 100 is configured to compare an input associated with at least one physiological characteristic associated with a biological subject to a data structure 152 including reference values, and to generate a response based in part on the comparison.

The system 100 can include, but is not limited to, one or more computer-readable media drives 154, interface sockets, Universal Serial Bus (USB) ports, memory card slots, and the like, and one or more input/output components such as, for example, a graphical user interface, a display, a keyboard, a keypad, a trackball, a joystick, a touch-screen, a mouse, a switch, a dial, and the like, and any other peripheral device. In an embodiment, the system 100 can include, but is not limited to, one or more user input/output components 156 that operably-couple to at least one controller 130 to control (electrical, electromechanical, software-implemented, firmware-implemented, or other control. or combinations thereof) at least one parameter associated with the delivery of the sterilizing stimulus.

The computer-readable media drive 154 or memory slot may be configured to accept signal-bearing medium (e.g., computer-readable memory media, computer-readable recording media, and the like). In an embodiment, a program for causing the system 100 to execute any of the disclosed methods can be stored on, for example, a computer-readable recording medium, a signal-bearing medium, and the like. Examples of signal-bearing media include, but are not limited to, a recordable type medium such as a magnetic tape, floppy disk, a hard disk drive, a Compact Disc (CD), a Digital Video Disk (DVD), Blu-Ray Disc, a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.). Further non-limiting examples of signal-bearing media include, but are not limited to, DVD-ROM, DVD-RAM, DVD+RW, DVD- RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, and the like. In an embodiment, the system 100 can include, but is not limited to, signal-bearing media in the form of one or more logic devices (e.g., programmable logic devices, complex programmable logic device, field-programmable gate arrays, application specific integrated circuits, and the like) comprising, for example, one or more look-up tables.

In an embodiment, the implantable device 102 includes for example, but not limited to, at least a first electrical sterilizing stimulus component 170 and a second electrical sterilizing stimulus component 172 operably coupled to one or more controllers 130. In an embodiment, one or more controllers 130 are configured to control at least one parameter associated with the delivery of at least one of the first sterilizing stimulus or the second sterilizing stimulus. For example, in an embodiment, at least one controller 130 is configured to control at least one of an excitation intensity, an excitation frequency, an excitation pulse frequency, an excitation pulse ratio, an excitation pulse intensity, an excitation pulse duration time, or an excitation pulse repetition rate associated with the delivery of at least one of the first sterilizing stimulus or the second sterilizing stimulus. In an embodiment, at least one controller 130 is configured to control at least one of a first or a second sterilizing stimulus delivery regimen parameter, a pulsed thermal sterilizing stimulus temporal delivery pattern parameter, a spaced-apart sterilizing stimulus delivery pattern parameter, a spatial electric field modulation parameter, a spatial electric field magnitude parameter, a spatial electric field distribution parameter, an ON-rate, or an OFF-rate associated with the delivery of at least one of the first sterilizing stimulus or the second sterilizing stimulus. In an embodiment, at least one controller 130 is configured to control at least one parameter associated with the delivery of the first sterilizing stimulus, and at least one other controller 130 is configured to control at least one parameter associated with the delivery of the second sterilizing stimulus.

In an embodiment, actively-controllable excitation component 106 is configured to reduce the concentration of an infecting agent in the immediate vicinity of an implant. In an embodiment, actively-controllable excitation component 106 is configured to concurrently or sequentially deliver a first sterilizing stimulus and a second sterilizing stimulus, in vivo, to tissue proximate the first outer surface. In an embodiment, at least one of the first sterilizing stimulus or the second sterilizing stimulus comprises a peak emission wavelength in the x-ray, ultraviolet, visible, infrared, near infrared, microwave, or radio frequency spectrum; and a controller 130 communicatively coupled to the actively-controllable excitation component, the controller 130 configured to regulate at least one parameter associated with the delivery of the sterilizing stimulus.

The actively-controllable excitation component 106 can include, but is not limited to, at least one energy-emitting component 124. In an embodiment, the at least one energy-emitting component 124 is configured to provide spatially-patterned sterilizing stimulus. Among the at least one energy-emitting component 124 examples include, but are not limited to, electrical energy emitters, electromagnetic energy emitters, optical energy emitters, energy photon emitters, light energy emitters, and the like. In an embodiment, the actively-controllable excitation component 106 can include, but is not limited to, at least one spatially-patterned energy-emitting element 114 configured to provide a spatially-patterned sterilizing stimulus to tissue proximate an implantable device 102. The spatially-patterned energy-emitting element 114 can include, but is not limited to, a plurality of spaced apart electrodes 116. In an embodiment, the spatially-patterned energy-emitting element 114 is configured to deliver a sterilizing stimulus of a character and for a time sufficient to provide a spatially-patterned sterilizing stimulus. The actively-controllable excitation component 106 can include, but is not limited to, a plurality of electrodes 118. In an embodiment, the plurality of electrodes 118 are configured to provide a spatially-patterned sterilizing stimulus.

Figure 5:
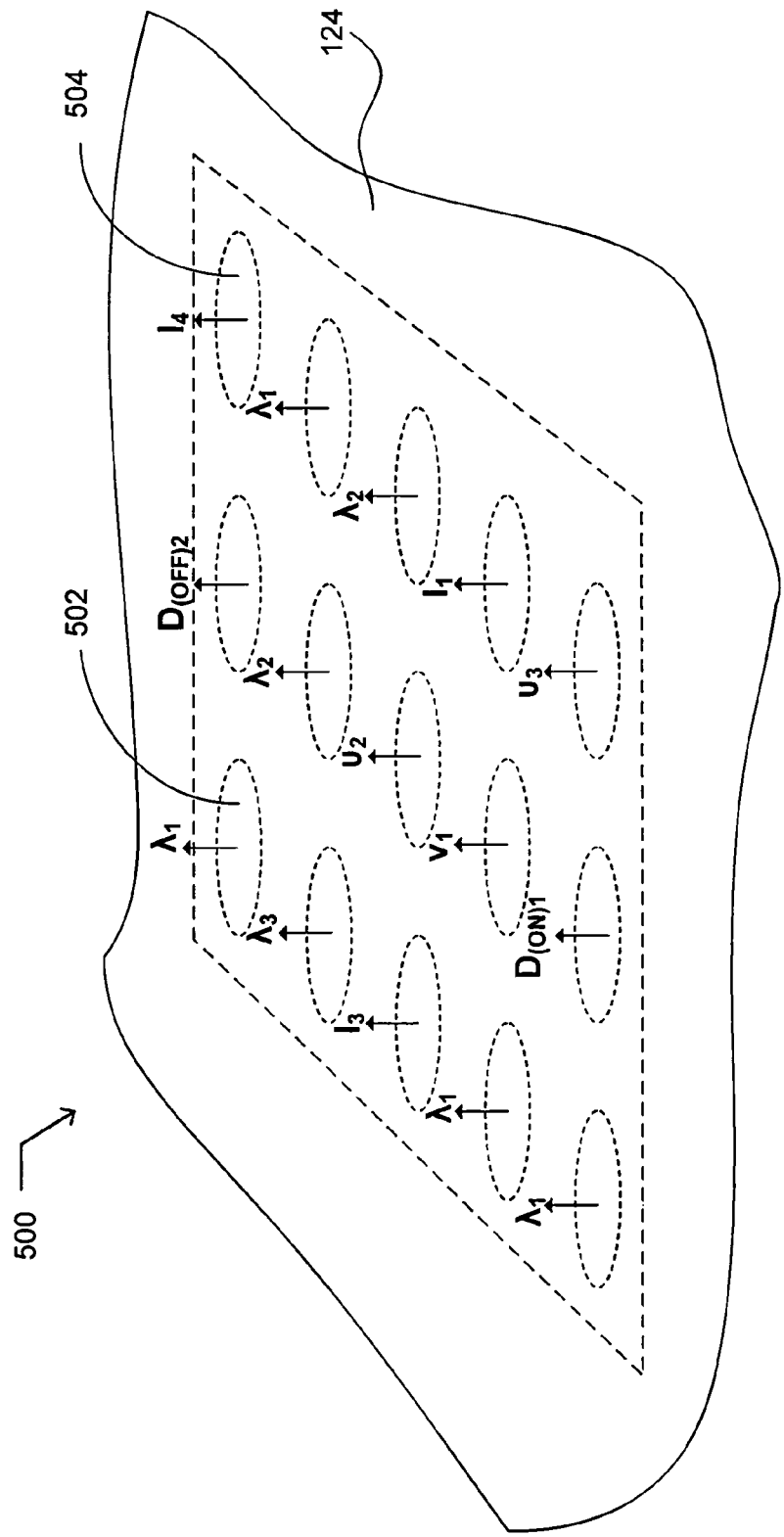
FIG. 5 is a perspective view of an energy-emitting component according to one illustrated embodiment.

Referring to FIG. 5, in an embodiment, the at least one energy-emitting component 124 is configured to provide an illumination pattern 500 comprising at least a first region 502 and a second region 504. In an embodiment, the second region 504 of the illumination pattern comprises at least one of an illumination intensity ($I_n$), an energy-emitting pattern, a peak emission wavelength ($a_n$), an ON-pulse duration ($D_{(ON)n}$), an OFF-pulse duration ($D_{(OFF)n}$), or a pulse frequency ($a_n$) different than the first region 502. The at least one energy-emitting component 124 can be configured to provide a spatially-patterned sterilizing stimulus having a peak emission wavelength in at least one of an x-ray, an ultraviolet, a visible, an infrared, a near infrared, a microwave, or a radio frequency spectrum, or combinations thereof, to at least a portion of tissue proximate an implantable device 102. In an embodiment, the at least one energy-emitting component 124 is configured to provide a spatially-patterned optical energy stimulus. The at least one energy-emitting component 124 can include, but is not limited to, a patterned-light emitting source 126. In an embodiment, the patterned-light emitting source 126 is configured to provide a spatially-patterned optical energy stimulus to tissue proximate the implantable device 102.

With continued reference to FIG. 2, the implantable device 102 can include, but is not limited to, at least one energy-emitting component 124. In an embodiment, the at least one energy-emitting component 124 is configured to provide a spatially-patterned light energy stimulus. In an embodiment, the at least one energy-emitting component 124 is configured to provide a spatially-patterned optical energy stimulus. In an embodiment, the at least one energy-emitting component includes a patterned light source.

In an embodiment, the actively-controllable excitation component 106 is operable to deliver a first electromagnetic sterilizing stimulus and a second sterilizing stimulus, in vivo, to tissue proximate the first outer surface, the second electromagnetic sterilizing stimulus having at least one of an illumination intensity, an energy-emitting pattern, a peak emission wavelength, an ON-pulse duration, an OFF-pulse duration, or a pulse frequency different than the first electromagnetic sterilizing stimulus.

Referring to FIG. 6, in an embodiment, the system 100 can include, but is not limited to, a control means 600. The control means 600 may include for example, but not limited to, electrical, electromechanical, software, firmware, or other control components, or combinations thereof. In an embodiment, the control means 600 may include electrical circuitry configured to for example, but not limited to, control at least one of a sterilizing stimulus delivery regimen parameter, a pulsed thermal sterilizing stimulus temporal delivery pattern parameter, a spaced-apart sterilizing stimulus delivery pattern parameter, a spatial electric field modulation parameter, a spatial electric field magnitude parameter, or a spatial electric field distribution parameter associated with the delivery of the sterilizing stimulus. In an embodiment, the control means 600 may include electrical circuitry configured to for example, but not limited to, control the one or more controllable-release ports configured to deliver the at least one scaffold-forming material to the first outer surface. Further examples of circuitry can be found, among other things, in U.S. Pat. No. 7,236,821 (issued Jun. 26, 2001), the contents of which is incorporated herein by reference. In a general sense, those skilled in the art will recognize that the various aspects described herein (which can be implemented, individually and/or collectively, by a wide range of hardware, software, firmware, and/or any combination thereof) can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

In an embodiment, the control means 600 may include one or more electro-mechanical systems configured to for example, control at least one of a sterilizing stimulus delivery regimen parameter, a pulsed thermal sterilizing stimulus temporal delivery pattern parameter, a spaced-apart sterilizing stimulus delivery pattern parameter, a spatial electric field modulation parameter, a spatial electric field magnitude parameter, or a spatial electric field distribution parameter associated with the delivery of the sterilizing stimulus. In an embodiment, the control means 600 may include one or more electro-mechanical systems configured to for example, but not limited to, control the one or more controllable-release ports configured to deliver the at least one scaffold-forming material to the first outer surface. In a general sense, the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof.

Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include, but are not limited to, a variety of consumer electronics systems, medical devices, as well as other systems such as motorized transport systems, factory automation systems, security systems, and/or communication/computing systems. The term, electro-mechanical, as used herein is not necessarily limited to a system that has both electrical and mechanical actuation except as context may dictate otherwise.

The implantable device 102 can include, among other things, a control means 600 operably coupled to the actively-controllable excitation component 106. In an embodiment, the control means 600 is configured to regulate at least one of a delivery regimen parameter, a pulsed thermal sterilizing stimulus temporal delivery pattern parameter, a spaced-apart delivery pattern parameter, and a temporal delivery pattern parameter associated with the delivery of the pulsed thermal sterilizing stimulus. In an embodiment, the actively-controllable excitation component 106 is configured to deliver a pulsed thermal sterilizing stimulus including at least a first pulsed waveform segment and a second pulsed waveform segment, the second pulsed waveform segment having at least one of a pulse duration, a pulse frequency, a pulse intensity, a pulse ratio, or a pulse repetition rate different from the first pulsed waveform segment.

In an embodiment, the control means 600 is configured to control one or more parameters associated with at least one of a pulse duration, a pulse frequency, a pulse intensity, a pulse ratio, or a pulse repetition rate associated with al least one of the first pulsed waveform segment or the second pulsed waveform segment. In an embodiment, the control means 600 is configured to control one or more parameters associated with at least one of a pulsed thermal sterilizing stimulus duration, a pulsed thermal sterilizing stimulus frequency, a pulsed thermal sterilizing stimulus intensity, or a pulsed thermal sterilizing stimulus repetition rate. In an embodiment, the control means 600 is configured to control at least one of a duration time, a delivery schedule, a delivery location, or a spatial-pattern stimulation configuration associated with the delivery of the pulsed thermal sterilizing stimulus. In an embodiment, the implantable device 102 includes one or more sensors 902 configured to determine at least one characteristic associated with a biological sample proximate the first outer surface 104. In an embodiment, the control means 600 is configured to change at least one of the delivery regimen parameter, the pulsed thermal sterilizing stimulus temporal delivery pattern parameter, the spaced-apart delivery pattern parameter, or the temporal delivery pattern parameter in response to a comparison between one or more real-time measurands associated with a tissue proximate the first outer surface and user specific information. In an embodiment, the control means 600 is configured to change at least one of a pulse duration time, a pulse frequency, a pulse intensity, a pulse ratio, or a pulse repetition rate associated with the delivery of the pulsed thermal sterilizing stimulus in response to a determination that an infectious agent is present within a biological sample proximate one or more regions of the first outer surface 104.

In an embodiment, the control means 600 is operably coupled to the one or more sensors 902 and is configured to generate a response based on a detected characteristic associated with a tissue proximate the first outer surface 103. In an embodiment, the control means 600 is configured to perform a comparison of the at least one characteristic associated with biological sample proximate the first outer surface 103 to stored reference data and to generate a response based at least in part on the comparison. In an embodiment, the implantable device 102 includes one or more processors operably coupled to the actively-controllable excitation component 106 and configured to perform a comparison of the determined at least one characteristic associated with the biological sample proximate the first outer surface 103 to stored reference data and to energize the actively-controllable excitation component 106 in response to the comparison.

In an embodiment, the system 100 can include for example, but not limited to; a control means 600 for operably coupling to the actively-controllable excitation component 106. In an embodiment, the control means 600 is operable to control at least one of component associated with the delivery of the sterilizing stimulus. Such components may include for example, but not limited to, a delivery regimen component 604, a spaced-apart sterilizing stimulus delivery pattern component 606, a spatial electric field modulation component 608, a spatial electric field magnitude component 610, a spatial electric field distribution component 612, or the like associated with the delivery of the sterilizing stimulus. In an embodiment, the control means 600 is operable to control at least of a spatial illumination field modulation component 614, a spatial illumination field intensity component 616, or a spatial illumination delivery pattern component 618. In an embodiment, the control means 600 is operable to control at least one sterilizing stimulus delivery regimen parameter selected from an excitation intensity, an excitation frequency, an excitation pulse frequency, an excitation pulse ratio, an excitation pulse intensity, an excitation pulse duration time, an excitation pulse repetition rate, an ON-rate, or an OFF-rate. A "duty cycle" includes, but is not limited to, a ratio of a pulse duration ($\tau$) relative to a pulse period (T). For example, a pulse train having a pulse duration of 10 as and a pulse signal period of 40 as, corresponds to a duty cycle (D=$\tau$/T) of 0.25. In an embodiment, the control means 600 is operable to manage a duty cycle associated with emitting an effective amount of the electrical sterilizing stimulus from the actively-controllable excitation component 106.

In an embodiment, the control means 600 is operable to control at least one component 620 associated with the delivery of the scaffold-forming material 402. Such components may include for example, but not limited to, a delivery rate component, a delivery amount component, a delivery composition component, a port release rate component, a port release amount component a port release pattern component or the like.

The control means 600 can include, but is not limited to, one or more controllers 630 such as a processor (e.g., a microprocessor) 632, a central processing unit (CPU) 634, a digital signal processor (DSP) 636, an application-specific integrated circuit (ASIC) 638, a field programmable gate array 640, and the like, and combinations thereof, and may include discrete digital and/or analog circuit elements or electronics. In an embodiment, the control means 600 is configured to wirelessly couple to an implantable device 102 that communicates via wireless communication with the control means 600. Examples of wireless communication include for example, optical connections, audio, ultraviolet connections, infrared, BLUETOOTH®, Internet connections, network connections, and the like.

In an embodiment, the control means 600 includes at least one controller 630, which is communicably-coupled to the actively-controllable excitation component 106. In an embodiment, the control means 600 is configured to control at least one of a duration time, a delivery location, or a spatial-pattern stimulation configuration associated with the delivery of the sterilizing stimulus.

The control means 600 can include, but is not limited to, one or more memories 642 that store instructions or data, for example, volatile memory (e.g., random access memory (RAM) 644, dynamic random access memory (DRAM), and the like) non-volatile memory (e.g., read-only memory (ROM) 646, electrically erasable programmable read-only memory (EEPROM), compact disc read-only memory (CD-ROM), and the like), persistent memory, and the like. Further non-limiting examples of one or more memories 642 include erasable programmable read-only memory (EPROM), flash memory, and the like. The one or more memories can be coupled to, for example, one or more controllers by one or more instruction, data, or power buses.

The control means 600 may include a computer-readable media drive or memory slot 652, and one or more input/output components 654 such as, for example, a graphical user interface, a display, a keyboard, a keypad, a trackball, a joystick, a touch-screen, a mouse, a switch, a dial, and the like, and any other peripheral device. The control means 600 may further include one or more databases 648, and one or more data structures 650. The computer-readable media drive or memory slot may be configured to accept computer-readable memory media. In some embodiments, a program for causing the system 100 to execute any of the disclosed methods can be stored on a computer-readable recording medium. Examples of computer-readable memory media include CD-R, CD-ROM, DVD, flash memory, floppy disk, hard drive, magnetic tape, magnetooptic disk, MINIDISC, non-volatile memory card, EEPROM, optical disk, optical storage, RAM, ROM, system memory, web server, and the like.

Figure 7:
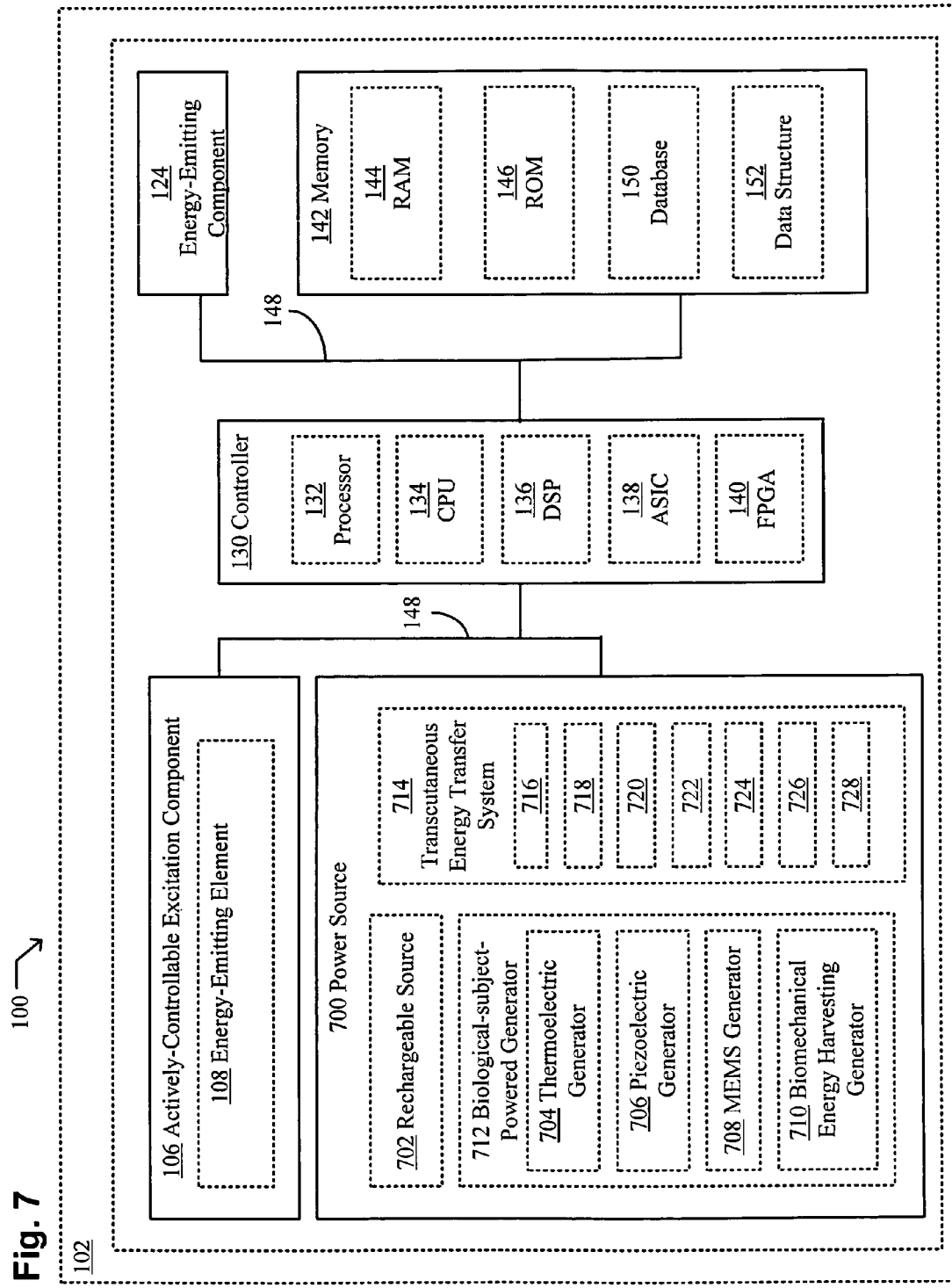
FIG. 7 is a schematic diagram of a system including an implantable device according to one illustrated embodiment.

Referring to FIG. 7, the implantable device 102 can include, but is not limited to, one or more power sources 700. In an embodiment, the power source 700 is electromagnetically, magnetically, ultrasonically, optically, inductively, electrically, or capacitively-coupleable to the actively-controllable excitation component. In an embodiment, the power source 700 is carried by the implantable device 102. In an embodiment, the power source 700 comprises at least one rechargeable power source 702.

Among power sources 700 examples include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, and the like. Further non-limiting examples of power sources 700 include one or more generators (e.g., electrical generators, thermo energy-to-electrical energy generators, mechanical-energy-to-electrical energy generators, micro-generators, nano-generators, and the like) such as, for example, thermoelectric generators 704, piezoelectric generators 706, electromechanical generators 708, biomechanical-energy harvesting generators 710, and the like. In an embodiment, the implantable device 102 can include, but is not limited to, one or more generators configured to harvest mechanical energy from for example, ultrasonic waves, mechanical vibration, blood flow, and the like. In an embodiment, the implantable device 102 can include one or more power receivers configurable to receive power from an in vivo power source. In an embodiment, the implantable device 102 can include, but is not limited to, at least one of a battery, a capacitor, and a mechanical energy store (e.g., a spring, a flywheel, or the like).

In an embodiment, the implantable device 102 can include, but is not limited to, one or more biological-subject (e.g., human)-powered generators 712. In an embodiment, the biological-subject-powered generator is configured to harvest energy from for example, but not limited to, motion of one or more joints. In an embodiment, the biological-subject-powered generator is configured to harvest energy generated by the biological subject using at least one of a thermoelectric generator 704, piezoelectric generator 706, electromechanical generator 708, biomechanical-energy harvesting generator 710, and the like.

In an embodiment, the biological-subject-powered generator 712 is configured to harvest thermal energy generated by the biological subject. In an embodiment, a thermoelectric generator 704 is configured to harvest heat dissipated by the biological subject. In an embodiment, the biological-subject-powered generator 712 is configured to harvest energy generated by any physical motion or movement (e.g., walking,) by biological subject. For example, in an embodiment, the biological-subject-powered generator 712 is configured to harvest energy generated by the movement of a joint within the biological subject. In an embodiment, the biological-subject-powered generator 712 is configured to harvest energy generated by the movement of a fluid within the biological subject.

In an embodiment, the power source 700 includes at least one of a thermoelectric generator, a piezoelectric generator, an electromechanical generator, or a biomechanical-energy harvesting generator, and at least one of a button cell, a chemical battery cell, a fuel cell, a secondary cell, a lithium ion cell, a micro-electric patch, a nickel metal hydride cell, silver-zinc cell, a capacitor, a super-capacitor, a thin film secondary cell, an ultra-capacitor, or a zinc-air cell. In an embodiment, the power source 700 includes at least one rechargeable power source.

In an embodiment, the implantable device 102 can include, but is not limited to, a power source 700 including at least one of a thermoelectric generator 704, a piezoelectric generator 706, an electromechanical generator 708, or a biomechanical-energy harvesting generator 710. In an embodiment, the power source 700 is configured to wirelessly receive power from a remote power supply 712. In an embodiment, the power source 700 is configured to manage a duty cycle associated with emitting an effective amount of the sterilizing stimulus from the actively-controllable excitation component 106.

In an embodiment, the actively-controllable excitation component 106 is configured to provide a voltage across at least a portion of the tissue proximate the implantable device 102 from a power source 700 coupled to the implantable device 102. In an embodiment, the voltage is sufficient to exceed a nominal dielectric strength of a cell plasma membrane without substantially interfering with a normal operation of the implantable device 102. In an embodiment, the voltage is sufficient to reduce the concentration of an infecting agent in the immediate vicinity of an implant.

The implantable device 102 may include a transcutaneous energy transfer system 714. In an embodiment, the transcutaneous energy transfer system 714 is electromagnetically, magnetically, ultrasonically, optically, inductively, electrically, or capacitively-coupleable to a power supply. In an embodiment, the transcutaneous energy transfer system 714 is electromagnetically, magnetically, ultrasonically, optically, inductively, electrically, or capacitively-coupleable to the actively-controllable excitation component 106. In an embodiment, the transcutaneous energy transfer system 714 includes at least one electromagnetically-coupleable power supply 716, magnetically-coupleable power supply 718, ultrasonically-coupleable power supply 720, optically-coupleable power supply 722, inductively-coupleable power supply 724, electrically-coupleable power supply 726, or capacitively-coupleable power supply 728.

The transcutaneous energy transfer system 714 can include, but is not limited to, an inductive power supply. In an embodiment, the inductive power supply includes a primary winding operable to produce a varying magnetic field. The implantable device 102 can include, but is not limited to, a secondary winding electrically coupled to the actively-controllable excitation component 106 for providing a voltage to tissue proximate the implantable device 102 in response to the varying magnetic field of the inductive power supply. In an embodiment, the transcutaneous energy transfer system 714 can include, but is not limited to, a secondary coil configured to provide an output voltage ranging from about 10 volts to about 25 volts. In an embodiment, the transcutaneous energy transfer system 714 is configured to manage a duty cycle associated with emitting an effective amount of the sterilizing stimulus from the actively-controllable excitation component 106. In an embodiment, the transcutaneous energy transfer system 714 is configured to transfer power to the implantable device 102 and to recharge a power source 700 within the implantable device 102. In an embodiment, the implantable device 102 may include a power receiver configurable to receive power from an in vivo power source.

In an embodiment, the implantable device includes for example, but not limited to, an electrical sterilizing stimulus providing portion; an actively-controllable excitation component 106 configured to deliver an electrical sterilizing stimulus, in vivo, to tissue proximate the sterilizing stimulus providing portion of the implantable device; a controller 130 communicatively coupled to the actively-controllable excitation component; and a power source 700, the power source 700 electromagnetically, magnetically, ultrasonically, optically, inductively, electrically, or capacitively-coupled to the actively-controllable excitation component.

Figure 8:
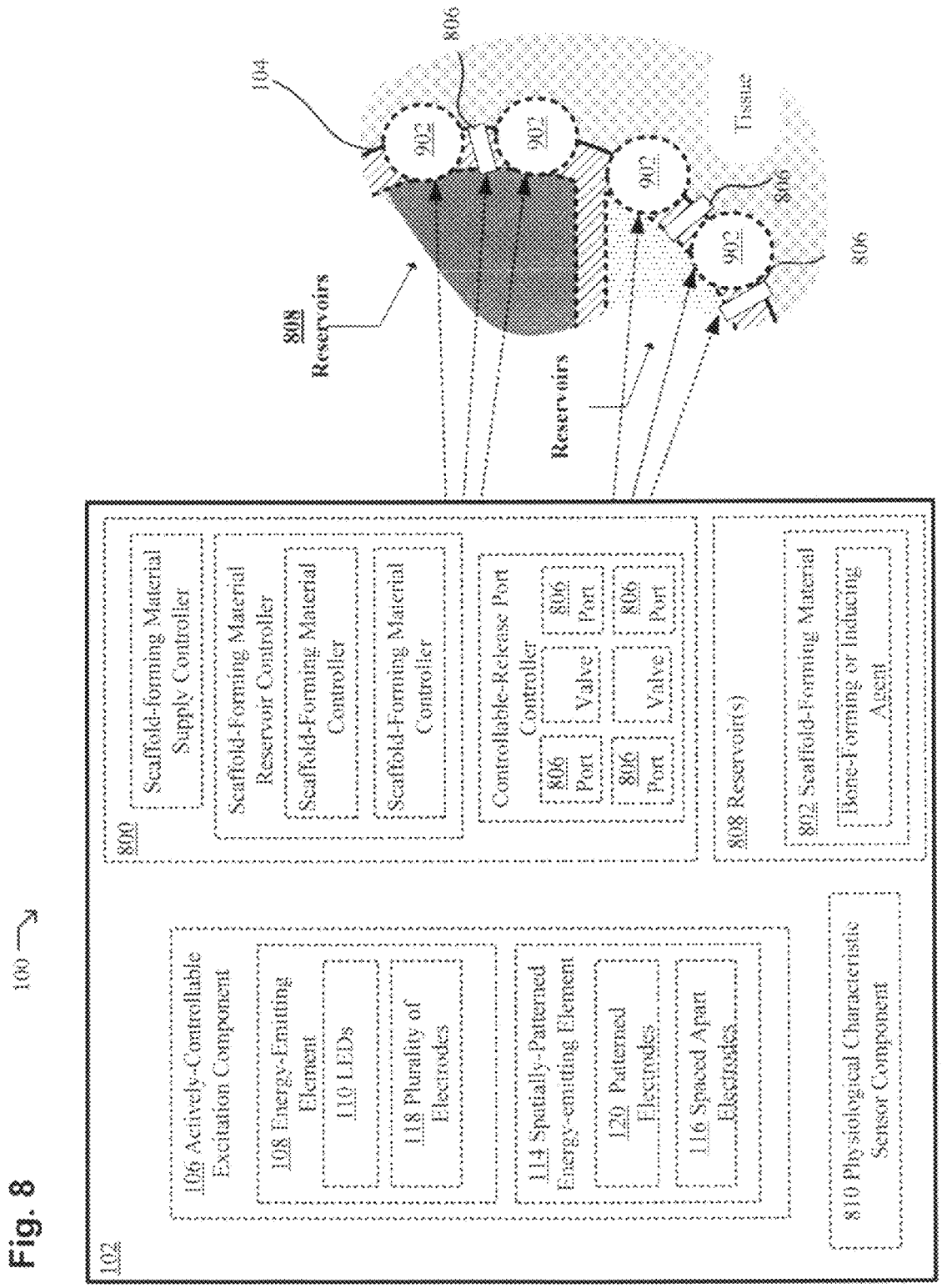
FIG. 8 is a schematic diagram of a system including an implantable device according to one illustrated embodiment.

Referring to FIG. 8, the implantable device 102 can include, but is not limited to, a scaffold-forming material supply component 800 configured to deliver at least one scaffold-forming material 802 to an outer surface of the implantable device 102. In an embodiment, the scaffold-forming material supply component 800 is configured to deliver at least one scaffold-forming material 802 to at least a first outer surface 104 of the implantable device 102. In an embodiment, the scaffold-forming material supply component 800 is configured to deliver at least one scaffold-forming material 802 in the immediate vicinity of implantable device 102.

In an embodiment, the scaffold-forming material supply component 800 includes one or more release ports 804 to deliver the at least one scaffold-forming material 802 to the first outer surface. In an embodiment, the scaffold-forming material supply component 800 includes one or more controllable-release ports 806 to deliver the at least one scaffold-forming material 802 to the first outer surface 104 of the implantable device 102. In an embodiment, the implantable device 102 can include, but is not limited to, at least one scaffold-forming material reservoir 808. In an embodiment, the scaffold-forming material supply component 800 includes one or more controllable-release ports 806 to deliver the at least one scaffold-forming material 802 form the at least one scaffold-forming material reservoir 808 to the first outer surface 104 of the implantable device 102.

Among scaffold-forming materials 802 examples include, but are not limited to, scaffold-forming collagens, scaffold-forming proteins, scaffold-forming substances, and the like. Further non-limiting examples of scaffold-forming materials 802 include Type I collagen, Type II collagen, Type III collagen, Type VII collagen, or Type X collagen, and the like. Further non-limiting examples of scaffold-forming materials include elastin fibers, soluble elastin, hydrophobic non-glycosylated proteins, and the like. Further non-limiting examples of scaffold-forming materials 802 include aggrecan, albumin, bone, cartilage, chondroitan sulfate proteoglycan, collagen, fibrin, gelatin, glycosaminoglycans, globulin, glutaraldehyde-cross-linked pericardium, heparan sulfate proteoglycans, hide powder, hyaluronic acid, hydroxylapatite, keratin, ligament, nitinol, nucleic acid polymers, polyethelene, polyethylene glycol, polyethylene glycol diacrylate, polyethylene terephthalate fiber, polyglycol, polylactate, polytetrafluoroethylene, proteoglycans, tendon, and the like.

In an embodiment, the scaffold-forming material 802 comprises at least one of scaffold-forming collagens, scaffold-forming proteins, or scaffold-forming substances. In an embodiment, the scaffold-forming material 802 comprises at least one of Type I collagen, Type II collagen, Type III collagen, Type VII collagen, or Type X collagen. In an embodiment, the scaffold-forming material 802 comprises at least one of elastin fibers, soluble elastin, or hydrophobic non-glycosylated proteins. In an embodiment, the scaffold-forming material 802 comprises at least one of albumin, bone, cartilage, fibrin, gelatin, globulin, glutaraldehyde-cross-linked pericardium, hide powder, hyaluronic acid, hydroxylapatite, keratin, ligament, nitinol, nucleic acid polymers, polyethelene, polyethylene glycol, polyethylene glycol diacrylate, polyethylene terephthalate fiber, polyglycol, polylactate, polytetrafluoroethylene, or tendon.

In an embodiment, the scaffold-forming material 802 comprises at least one growth promoting materials. Growth promoting materials can includes any agent that functions to, for example, but not limited to, promote or induce cell proliferation and cell survival. Examples of growth promoting material (e.g., growth factor and the like) include, but are not limited to, transforming growth factor-alpha (TGF-α), transforming growth factor beta (TGF-β), granulocyte-colony stimulating factor (G-CSF), granulocyte-macrophage colony stimulating factor (GM-CSF), nerve growth factor (NGF), other neurotrophins such as brain-derived neurotrophic factor (BDNF), novel neutrophin-1 (NNT-1), neurotrophin-3 (NT-3), neurotrophin-4 (NT-4); platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF, or FGF-2), epidermal growth factor (EGF), hepatocyte growth factor (HGF), insulin-like growth factors (IGF1, IGF2, IGF3), vascular endothelial growth factor (VEGF), human growth hormone (hGH), placental transforming growth factor beta (PTGF-β), keratinocyte growth factor (KGF), stem cell factor (SCF), macrophage colony stimulating factor (M-CSF), pleiotrophin, amphiregulin, betacellulin, heparin-binding epidermal growth factor, heregulin (HRG), angiogenin, angiopoietin-1, angiopoietin-2, angiostatin, endostatin, platelet-derived endothelial cell growth factor, sonic hedgehog, and the like.

Further examples of growth promoting materials include bone morphogenic proteins (e.g., BMP-1, BMP-2, BMP-4, BMP-6, and BMP-7) as well as members of the transforming growth factor beta (TGF-β) superfamily including, but not limited to, TGF-β1, TGF-β2, and TGF-β3; growth differentiation factors (GDF1, GDF2, GDF3, GDF5, GDF6, GDF7, myostatin/GDF8, GDF9, GDF10, GDF11, and GDF15); and bone morphogenic proteins (BMP-1, BMP-2, BMP-4, BMP-6, and BMP-7).

In an embodiment, the scaffold-forming material 802 comprises at least one of bone-forming agents (e.g., parathyroid hormones, and the like), bone-growth inducing agents (e.g., bone growth proteins, bone morphogenic proteins, osteogenic proteins, statins, statin-like compounds (e.g., atorvastatin, cerivastatin, lovastatin, mevastatin, simvastatin, fluvastatin, pravastatin, rosuvastatin, saos-2 osteosarcoma cells, and the like), and the like.

In an embodiment, the implantable device 102 can include, but is not limited to, at least one processor communicably-coupled to the scaffold-forming material supply component 800 and configured to control at least one parameter associated with the delivery of the scaffold-forming material 802 to the first outer surface 104. In an embodiment, the implantable device 102 can include, but is not limited to, at least one processor communicably-coupled to the scaffold-forming material supply component 800 and configured to control at least one of a delivery rate, a delivery amount, a delivery composition, a port release rate, a port release amount, or a port release pattern associated with the delivery of the scaffold-forming material 802 to the first outer surface 104.

The implantable device 102 can include, but is not limited to, a means for communicably-coupling to the scaffold-forming material supply component 800 and means for controlling at least one parameter associated with the delivery of the scaffold-forming material 802 to the first outer surface. The means for controlling the at least one parameter associated with the delivery of the scaffold-forming material 802 may include electrical circuitry configured to control at least one of a delivery rate, a delivery amount, a delivery composition, a port release rate, a port release amount, or a port release pattern associated with the delivery of the scaffold-forming material to the first outer surface.

The means for controlling at least one parameter associated with the delivery of the scaffold-forming material may include one or more electro-mechanical systems for controlling one or more controllable-release ports 806 configured to deliver the at least one scaffold-forming material to the first outer surface. In a general sense, the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include, but are not limited to, a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

Figure 9:
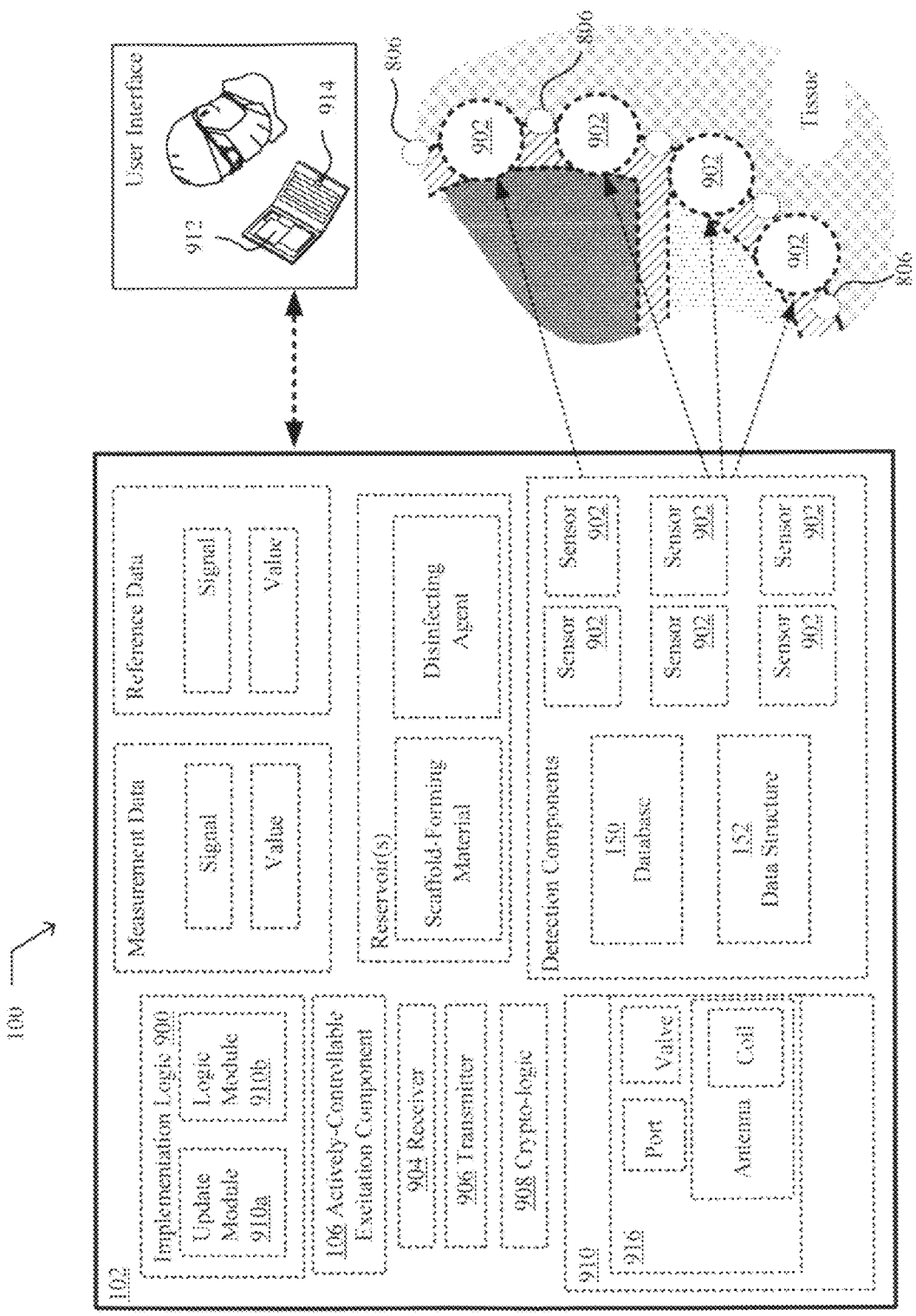
FIG. 9 is a schematic diagram of a system including an implantable device according to one illustrated embodiment.
Figure 10:
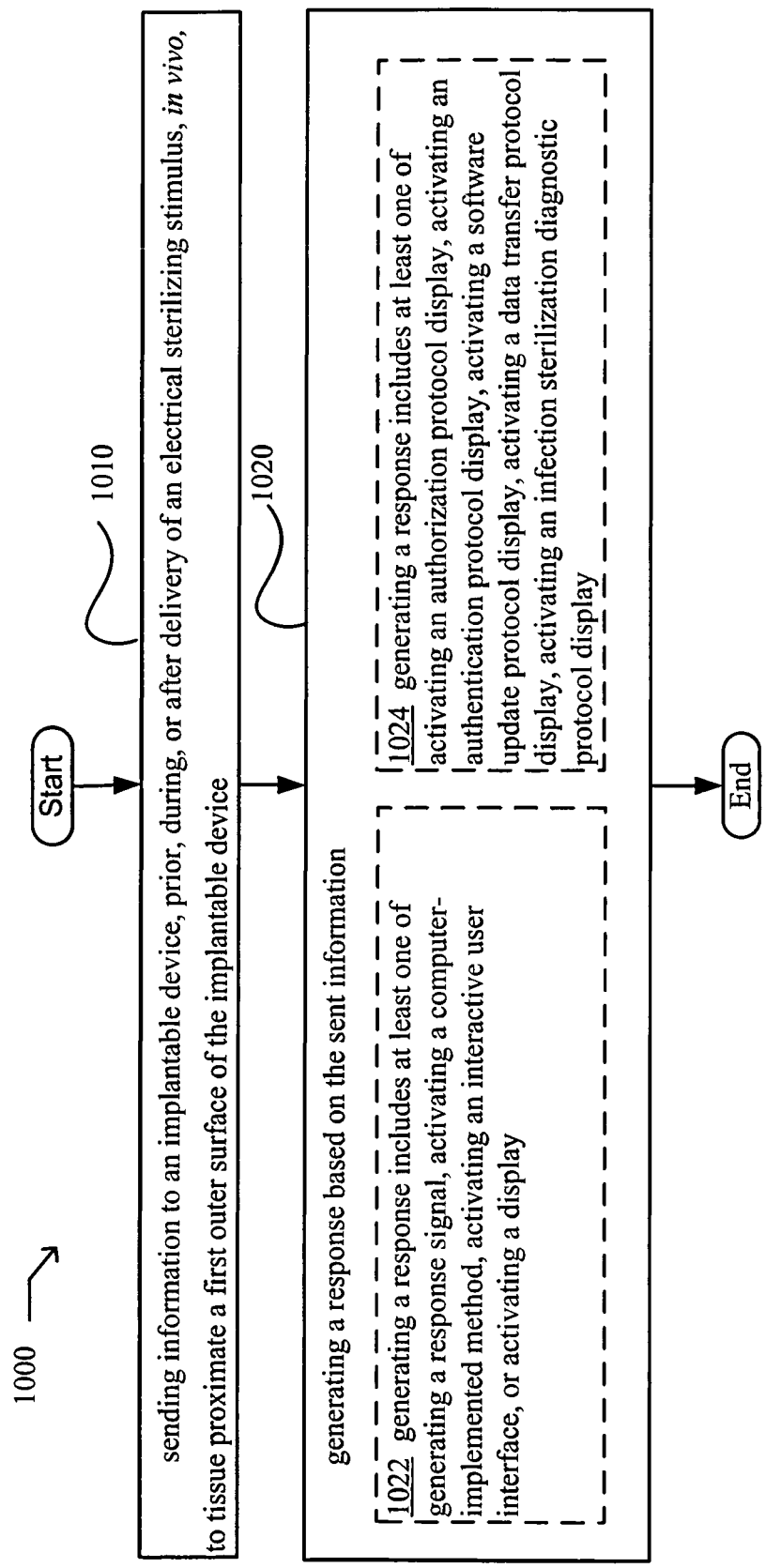
FIG. 10 is a flow diagram of a method according to one illustrated embodiment.

Referring to FIGS. 9 and 10, show a system 100 in which one or more technologies may be implemented comprising at least one implantable device 102. In an embodiment, the implantable device 102 can include, but is not limited to, one or more detection components including one or more sensors 902. In an embodiment, the one or more sensors 902 can be operable to determine (e.g., sense, measure, detect, assess, and the like) at least one of a physical quantity, an environmental attribute, a physiologic characteristic, and the like.

In an embodiment, the one or more sensors 902 are configured to determine at least one characteristic associated with a tissue proximate the implantable device 102. In an embodiment, the one or more sensors 902 are configured to determine at least one characteristic associated with a tissue proximate the implantable device 102. In an embodiment, the one or more sensors 902 are configured to determine at least one characteristic associated with a tissue proximate the first outer surface 104.

In an embodiment, the one or more sensors 902 are configured to determine a spatial dependence associated with the least one characteristic. In an embodiment, the one or more sensors 902 are configured to determine a temporal dependence associated with the least one characteristic. In an embodiment, the one or more sensors 902 are configured to concurrently or sequentially determine at least one spatial dependence associated with the least one characteristic and at least one temporal dependence associated with the least one characteristic.

Among the one or more sensors 902 examples include, but are not limited to, biosensors, blood volume pulse sensors, conductance sensors, electrochemical sensors, fluorescence sensors, force sensors, heat sensors (e.g., thermistors, thermocouples, and the like), high resolution temperature sensors, differential calorimeter sensors, optical sensors, oximetry sensors, potentiometric sensors, resistance sensors, respiration sensors, sound sensors (e.g., ultrasound), Surface Plasmon Band Gap sensor (SPRBG), physiological sensors, surface plasmon sensors, and the like. Further non-limiting examples of sensors include acoustic wave sensors, affinity sensors, bioprobes, biostatistics sensors, cantilevers, enzymatic sensors, in-situ sensors (e.g., in-situ chemical sensor), ion sensors, light sensors (e.g., visible, infrared, and the like), microbiological sensors, microhotplate sensors, micronscale moisture sensors, nanosensors, optical chemical sensors, single particle sensors, and the like. Further non-limiting examples of sensors include chemical sensors, cavitand-based supramolecular sensors, aptamer-based sensors, nucleic acid sensors, deoxyribonucleic acid sensors (e.g., electrochemical DNA sensors, and the like), supramolecular sensors, and the like. In an embodiment, at least one sensor is configured to detect or measure the presence or concentration of specific target chemicals (e.g., infecting agents, infection indication chemicals, inflammation indication chemicals, diseased tissue indication chemicals, biological agents, molecules, ions, and the like).

In an embodiment, the at least one characteristic associated with the tissue proximate the implantable device 102 includes at least one of an inflammation indication parameter, an infection indication parameter, a diseased state indication parameter (e.g., an absence, a presence, or a severity indication parameter), or a diseased tissue indication parameter. In an embodiment, the at least one characteristic associated with the tissue proximate the implantable device 102 includes at least one parameter associated with a diseased state. Non-liming suitable techniques for optically measuring a diseased state may be found in, for example, U.S. Pat. No. 7,167,734 (issued Jan. 23, 2007). In an embodiment, the at least one characteristic associated with the tissue proximate the implantable device 102 includes at least one of an electromagnetic energy absorption parameter, an electromagnetic energy emission parameter, an electromagnetic energy scattering parameter, an electromagnetic energy reflectance parameter, or an electromagnetic energy depolarization parameter. In an embodiment, the at least one characteristic associated with the tissue proximate the implantable device 102 includes at least one of an absorption coefficient, an extinction coefficient, or a scattering coefficient.

In an embodiment, the at least one characteristic associated with the tissue proximate the implantable device 102 includes at least one of a transmittance, an interrogation energy frequency change, a frequency shift, an interrogation energy phase change, or a phase shift. In an embodiment, the at least one characteristic associated with the tissue proximate the implantable device 102 includes at least one of a fluorescence, and intrinsic fluorescence, a tissue fluorescence, or a naturally occurring fluorophore fluorescence. In an embodiment, the at least one characteristic associated with the tissue proximate the implantable device 102 includes at least one of an electrical conductivity, and electrical polarizability, or an electrical permittivity. In an embodiment, the at least one characteristic associated with the tissue proximate the implantable device 102 includes at least one of a thermal conductivity, a thermal diffusivity, a tissue temperature, or a regional temperature.

In an embodiment, the at least one characteristic associated with the tissue proximate the implantable device 102 includes at least one parameter associated with an infection marker (e.g., an infectious agent marker), an inflammation marker, an infective stress marker, a systemic inflammatory response syndrome marker, or a sepsis marker. Examples of infection makers, inflammation marks, and the like may be found in, for example, Imam et al., *Radiotracers for imaging of infection and inflammation—A Review*, World J. Nucl. Med. 40-55 (2006), which is incorporated herein by reference.

In an embodiment, the at least one characteristic associated with the tissue proximate the implantable device 102 includes at least one of a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, or a pH level.

In an embodiment, the at least one characteristic associated with the tissue proximate the implantable device 102 includes at least one hematological parameter. Non-limiting examples of hematological parameters include an albumin level, a blood urea level, a blood glucose level, a globulin level, a hemoglobin level, erythrocyte count, a leukocyte count, and the like. the at least one characteristic associated with the tissue proximate the implantable device 102 includes at least one parameter associated with a red blood cell count, a lymphocyte level, a leukocyte count, a myeloid count, an erythrocyte sedimentation rate, or a C-reactive protein level.

In an embodiment, the at least one characteristic associated with the tissue proximate the implantable device 102 includes at least one parameter associated with a cytokine plasma concentration or an acute phase protein plasma concentration. In an embodiment, the at least one characteristic associated with the tissue proximate the implantable device 102 includes at least one parameter associated with a leukocyte level.

Many of the disclosed embodiments may be electrical, electromechanical, software-implemented, firmware-implemented, or other otherwise implemented, or combinations thereof. Many of the disclosed embodiments may be software or otherwise in memory, such as one or more executable instruction sequences or supplemental information as described herein. For example, in an embodiment, the implantable device 102 can include, but is not limited to, one or more processors configured to perform a comparison of the at least one characteristic associated with the tissue proximate the implantable device 102 to stored reference data, and to generate a response based at least in part on the comparison. In an embodiment, the generated response includes at least one of a response signal, a change to a sterilizing stimulus parameter, a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, or a change in a sterilizing stimulus delivery regiment parameter. In an embodiment, the control means is operably coupled to the one or more sensors 902, and is configured to determine the at least one characteristic associated with the tissue proximate the implantable device 102.

In an embodiment, the control means is operably coupled to at least a first sensor and at least a second sensor, and is configured to generate a comparison of first sensor data to second sensor data and to generate predictive information based on the comparison. In an embodiment, the control means is operably coupled to at least one sensor 902, and is configured to generate a comparison of first in time sensed data to second in time sensed data from the at least one sensor and to generate response based on the comparison. In an embodiment, the control means is operably coupled to at least one sensor 902, and is configured to generate a comparison of first in time sensed data to second in time sensed data from the at least one sensor and to generate predictive information based on the comparison. In an embodiment, the control means is operably coupled to at least one sensor 902, and is configured to generate a comparison of concurrently or sequentially detected first data to second data from the at least one sensor and to generate a response when the second data differs from the first data as a function of at least one of space and time.

In an embodiment, the control means 600 is configured to perform a comparison of the at least one characteristic associated with the tissue proximate the implantable device 102 to stored reference data, and to generate a response based at least in part on the comparison.

The implantable device 102 can include, but is not limited to, a tissue characteristic sensor component. In an embodiment, the tissue characteristic sensor component is configured to perform a comparison of the at least one characteristic associated with the tissue proximate the implantable device 102 to stored reference data, and to generate a response based at least in part on the comparison.

The implantable device 102 can include, but is not limited to, one or more sensors 902 configured to determine at least one physiological characteristic associated with a biological subject. For example, physiological characteristics such as, for example pH may be use to assess blood flow, a cell metabolic state (e.g., anaerobic metabolism, and the like), the presence of an infectious agent, a disease state, and the like. In an embodiment, the implantable device 102 can include, but is not limited to, one or more sensors 902 configured to determine at least one of a physiological characteristic of a biological subject, or a characteristic associated with a tissue proximate the implantable device 102.

Among physiological characteristics examples include, but are not limited to, at least one of a temperature, a regional or local temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, a respiratory rate, a vital statistic, and the like. In an embodiment, the at least one physiological characteristic includes at least one of a temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, or a respiratory rate.

In an embodiment, the at least one physiological characteristic includes at least one hematological parameter. In an embodiment, the hematological parameter is associated with a hematological abnormality. In an embodiment, the at least one physiological characteristic includes one or more parameters associated with at least one of leukopenia, leukophilia, lymphocytopenia, lymphocytophilia, neutropenia, neutrophilia, thrombocytopenia, disseminated intravascular coagulation, bacteremia, or viremia.

In an embodiment, the at least one physiological characteristic includes at least one of an infection marker, an inflammation marker, an infective stress marker, a systemic inflammatory response syndrome marker, or a sepsis marker. In an embodiment, the infection marker includes at least one of a red blood cell count, a lymphocyte level, a leukocyte count, a myeloid count, an erythrocyte sedimentation rate, or a C-reactive protein level. In an embodiment, the at least one physiological characteristic includes at least one of a cytokine plasma concentration or an acute phase protein plasma concentration.

In an embodiment, the control means is operably coupled to the one or more sensors 902, and is configured to determine the at least one physiological characteristic of the biological subject. In an embodiment, the control means is configured to perform a comparison of the determined at least one physiological characteristic of the biological subject to stored reference data, and to generate a response based at least in part on the comparison. In an embodiment, the generated response includes at least one of a response signal, a change to a sterilizing stimulus parameter, a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, or a change in a sterilizing stimulus delivery regiment parameter.

In an embodiment, the one or more sensors 902 are configured to determine the at least one characteristic associated with the biological sample proximate the first outer surface 104 at a plurality of successive time points. In an embodiment, the one or more sensors 902 are configured to determine a spatial dependence associated with the at least one characteristic associated with the biological sample proximate the first outer surface 104. In an embodiment, the one or more sensors 902 are configured to determine a temporal dependence associated with at least one characteristic associated with the biological sample proximate the first outer surface 104. In an embodiment, the at least one characteristic associated with the biological sample proximate the first outer surface 104 includes a tissue chromophore absorption coefficient. In an embodiment, the at least one characteristic associated with the biological sample proximate the first outer surface 104 includes a spectral change in electromagnetic energy absorption by a tissue chromophore. In an embodiment, the at least one characteristic associated with the biological sample proximate the first outer surface 104 includes a spectral characteristic indicative of a temperature dependent physiological change in a tissue. In an embodiment, the at least one characteristic associated with the biological sample proximate the first outer surface 104 includes at least one of an inflammation indication parameter, an infection indication parameter, a diseased state indication parameter, or a diseased tissue indication parameter.

In an embodiment, the at least one characteristic associated with the biological sample proximate the first outer surface 104 includes at least one of an electromagnetic energy absorption parameter, an electromagnetic energy emission parameter, an electromagnetic energy scattering parameter, an electromagnetic energy reflectance parameter, or an electromagnetic energy depolarization parameter. In an embodiment, the at least one characteristic associated with the biological sample proximate the first outer surface 104 includes at least one of a transmittance, a frequency change, a frequency shift, a phase change, or a phase shift associate with an interrogation energy stimulus. In an embodiment, the at least one characteristic associated with the biological sample proximate the first outer surface 104 includes at least one of a fluorescence, an intrinsic fluorescence, a tissue fluorescence, or a naturally occurring fluorophore fluorescence. In an embodiment, the at least one characteristic associated with the biological sample proximate the first outer surface 104 includes at least one of an electrical conductivity, an electrical polarizability, or an electrical permittivity. In an embodiment, the at least one characteristic associated with the biological sample proximate the first outer surface 104 includes at least one of a thermal conductivity, a thermal diffusivity, a tissue temperature, or a regional temperature. In an embodiment, the at least one characteristic associated with the biological sample proximate the first outer surface 104 includes at least one of an absorption coefficient, an extinction coefficient, a scattering coefficient, or a transmission coefficient. In an embodiment, the at least one characteristic associated with biological sample proximate the first outer surface 104 includes a phase change to an interrogation energy stimulus. In an embodiment, the at least one characteristic associated with biological sample proximate the first outer surface 104 includes a refractive index parameter. In an embodiment, the at least one characteristic associated with biological sample proximate the first outer surface 104 includes at least one parameter associated with an infection marker, an inflammation marker, an infective stress marker, a systemic inflammatory response syndrome marker, or a sepsis marker. In an embodiment, the at least one characteristic associated with biological sample proximate the first outer surface 104 includes at least one of a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, or a pH level. In an embodiment, the at least one characteristic associated with biological sample proximate the first outer surface 104 includes at least one parameter associated with a red blood cell count, a lymphocyte count, a leukocyte count, a myeloid count, an erythrocyte sedimentation rate, or a c-reactive protein level. In an embodiment, the at least one characteristic associated with biological sample proximate the first outer surface 104 includes at least one parameter associated with a cytokine plasma concentration or an acute phase protein plasma concentration. In an embodiment, the at least one characteristic associated with biological sample proximate the first outer surface 104 includes at least one parameter associated with a leukocyte level.

The implantable device 102 can include, but is not limited to, circuitry for performing a comparison of the determined at least one characteristic associated with the tissue proximate the first outer surface to stored reference data following delivery of the sterilizing stimulus. The implantable device 102 can include, but is not limited to, circuitry for generating a response based at least in part on the comparison.

The implantable device 102 can include, but is not limited to, one or more processors configured to perform a comparison of the at least one characteristic associated with the tissue proximate the first outer surface to stored reference data following delivery of the sterilizing stimulus, and to generate a response based at least in part on the comparison. In an embodiment, the generated response can include, but is not limited to, at least one of a response signal, a control signal, a change to an sterilizing stimulus parameter (e.g., an electrical sterilizing stimulus, an electromagnetic sterilizing stimulus, an ultrasonic sterilizing stimulus, or a thermal sterilizing stimulus), a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, a change to a sterilizing stimulus spatial pattern parameter (e.g., an electrical sterilizing stimulus spatial pattern parameter, an electromagnetic sterilizing stimulus spatial pattern parameter, an ultrasonic sterilizing stimulus spatial pattern parameter, or a thermal sterilizing stimulus spatial pattern parameter), or a change in an sterilizing stimulus delivery regiment parameter (e.g., an electrical sterilizing stimulus delivery regiment parameter, an electromagnetic sterilizing stimulus delivery regiment parameter, an ultrasonic sterilizing stimulus delivery regiment parameter, or a thermal sterilizing stimulus delivery regiment parameter).

The system 100 can include, but is not limited to, a physiological characteristic sensor component 810. In an embodiment, the physiological characteristic sensor component 810 is configured to perform a comparison of the determined at least one physiological characteristic of the biological subject to stored reference data, and to generate a response based at least in part on the comparison. The implantable device 102 can include, but is not limited to, one or more processors configured to perform a comparison of the determined at least one physiological characteristic of the biological subject to stored reference data, and to generate a response based at least in part on the comparison.

The system 100 can include, one or more implantable devices 102 including for example, but is not limited to, circuitry for obtaining information, and circuitry for storing the obtained information. In an embodiment, the circuitry for obtaining information includes circuitry for obtaining information associated with a delivery of the sterilizing stimulus. In an embodiment, the circuitry for obtaining information includes circuitry for obtaining at least one of a command stream, a software stream, or a data stream. The implantable device 102 can include, but is not limited to, one or more processors configured to perform a comparison of at least one physiological characteristic of a biological subject to the obtained information, and to generate a response based at least in part on the comparison.

Referring to FIG. 9, the system 100 can include, one or more implantable devices 102 including for example, but not limited to, at least one receiver 904 configured to acquire information. In an embodiment, the at least one receiver 904 is configured to acquire information associated with a delivery of the sterilizing stimulus. In an embodiment, the at least one receiver 904 is configured to acquire data. In an embodiment, the at least one receiver 904 is configured to acquire software. In an embodiment, the at least one receiver 904 is configured to receive data from one or more distal sensors. In an embodiment, the at least one receiver 904 is configured to receive stored reference data.

The system 100 can include, one or more implantable devices 102 including for example, but not limited to, circuitry for providing information. In an embodiment, the circuitry for providing information includes circuitry for providing status information regarding the implantable device. In an embodiment, the circuitry for providing information includes circuitry for providing information regarding at least one characteristic associated with a tissue proximate the first outer surface. The system 100 can include, one or more implantable devices 102 including for example, but not limited to, at least one transmitter 906 configured to send information. The system 100 can include, one or more implantable devices 102 including for example, but not limited to, circuitry for transmitting information.

The system 100 can include, one or more implantable devices 102 including for example, but not limited to, one or more cryptographic logic components 908. In an embodiment, at least one of the one or more cryptographic logic components 908 is configured to implement at least one cryptographic process, or cryptographic logic, or combinations thereof. Examples of a cryptographic process include, but are not limited to one or more process associated with cryptographic protocols, decryption protocols, encryption protocols, regulatory compliance protocols (e.g., FDA regulatory compliance protocols, or the like), regulatory use protocols, authentication protocols, authorization protocols, delivery protocols, activation protocols, encryption protocols, decryption protocols, and the like. Examples of a cryptographic logic include one or more crypto-algorithms signal-bearing media, crypto controllers (e.g., crypto-processors), cryptographic modules (e.g., hardware, firmware, or software, or combinations thereof for implementing cryptographic logic, or cryptographic processes), and the like.

The system 100 can include, but is not limited to, one or more modules 910 optionally operable for communication with one or more user interfaces 912 operable for relaying user output and/or input 914. Module 910 comprises one or more instances of (electrical, electromechanical, software-implemented, firmware-implemented, or other control) devices 916. Device 916 may comprise one or more instances of memory, processors, ports, valves, antennas, power, or other supplies; logic modules or other signaling modules; gauges or other such active or passive detection components; or piezoelectric transducers, shape memory elements, micro-electro-mechanical system (MEMS) elements, or other actuators.

FIG. 10 shows an example of a method 1000.

At 1010, the method 1000 includes sending information to an implantable device 102, prior, during, or after delivery of a sterilizing stimulus, in vivo, to tissue proximate a first outer surface 104 of the implantable device 102. In an embodiment, sending information to an implantable device includes sending information to an implantable device, prior, during, or after delivery of at least one of an electrical sterilizing stimulus, an electromagnetic sterilizing stimulus, an ultrasonic sterilizing stimulus, or a thermal sterilizing stimulus.

At 1020, the method 1000 includes generating a response based on the sent information. At 1022, generating the response may include at least one of generating a response signal, activating a computer-implemented method, activating an interactive user interface, or activating a display. At 1024, generating the response may include at least one of activating an authorization protocol display, activating an authentication protocol display, activating a software update protocol display, activating a data transfer protocol display, activating an infection sterilization diagnostic protocol display.

Figure 11:
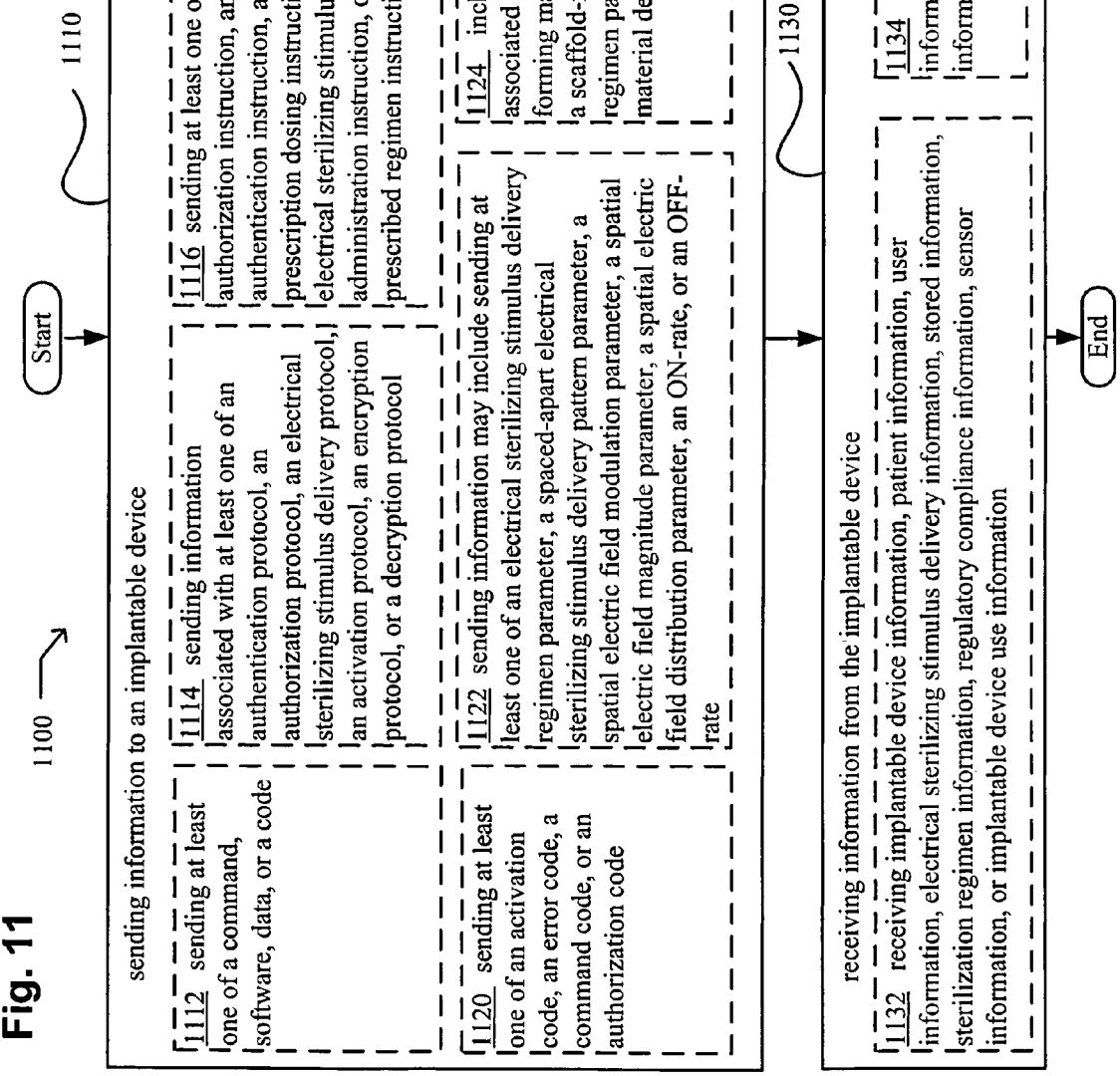
FIG. 11 is a flow diagram of a method according to one illustrated embodiment.

FIG. 11 shows an example of a method 1100.

At 1110, the method 1100 includes sending information to an implantable device that includes: a first outer surface 104, an actively-controllable excitation component 106 configured to deliver an electrical sterilizing stimulus, in vivo, to tissue proximate the first outer surface 104 of the implantable device 102, and a controller 130 communicatively coupled to the actively-controllable excitation component 106. At 1112, sending information may include sending at least one of a command, software, data, or a code. At 1114, sending information may include sending information associated with at least one of an authentication protocol, an authorization protocol, a sterilizing stimulus delivery protocol, an activation protocol, an encryption protocol, or a decryption protocol. In an embodiment, sending information may include sending information associated with at least one of an electrical sterilizing stimulus delivery protocol, an electromagnetic sterilizing stimulus delivery protocol, an ultrasonic sterilizing stimulus delivery protocol, or a thermal sterilizing stimulus delivery protocol.

At 1116, sending information may include sending at least one of an authorization instruction, an authentication instruction, a prescription dosing instruction, a sterilizing stimulus administration instruction, or a prescribed regimen instruction. At 1118, sending information may include sending at least one of an instruction stream, an encrypted data stream, an authentication data stream, or an authorization data stream. At 1120, sending information may include sending at least one of an activation code, an error code, a command code, or an authorization code. In an embodiment, sending information may include sending at least one of patient information, sensor information, sensed data, physiological sensor data, or physiological reference data.

At 1122, sending information may include sending at least one of a sterilizing stimulus delivery regimen parameter, a pulsed thermal sterilizing stimulus temporal delivery pattern parameter, a spaced-apart sterilizing stimulus delivery pattern parameter, a spatial electric field modulation parameter, a spatial electric field magnitude parameter, a spatial electric field distribution parameter, an ON-rate, or an OFF-rate. At 1124, sending information may include sending information associated with at least one of a scaffold-forming material delivery pattern parameter, a scaffold-forming material delivery regimen parameter, or a scaffold-forming material delivery rate parameter. In an embodiment, sending information may include sending information associated with at least one of an electrical sterilizing stimulus delivery pattern parameter, an electromagnetic sterilizing stimulus delivery pattern parameter, an ultrasonic sterilizing stimulus delivery pattern parameter or a thermal sterilizing stimulus delivery pattern parameter. In an embodiment, sending information may include sending information associated with at least one of an electrical sterilizing stimulus delivery regimen parameter, an electromagnetic sterilizing stimulus delivery regimen parameter, an ultrasonic sterilizing stimulus delivery regimen parameter or a thermal sterilizing stimulus delivery regimen parameter.

At 1130, the method 1100 may include receiving information from the implantable device 102. At 1132, receiving information from the implantable device 102 may include receiving implantable device information, patient information, user information, sterilizing stimulus delivery information, stored information, sterilization regimen information, regulatory compliance information, sensor information, or implantable device use information. At 1134, receiving information from the implantable device 102 may include receiving regulatory compliance information or regulatory use information. In an embodiment, receiving information may include receiving sensor data. In an embodiment, receiving information may include receiving a control signal. In an embodiment, receiving information may include includes receiving a request for transmission of information. In an embodiment, receiving information may include receiving a request for transmission of at least one of data, a command, an authorization, an update, or a code.

Figure 12:
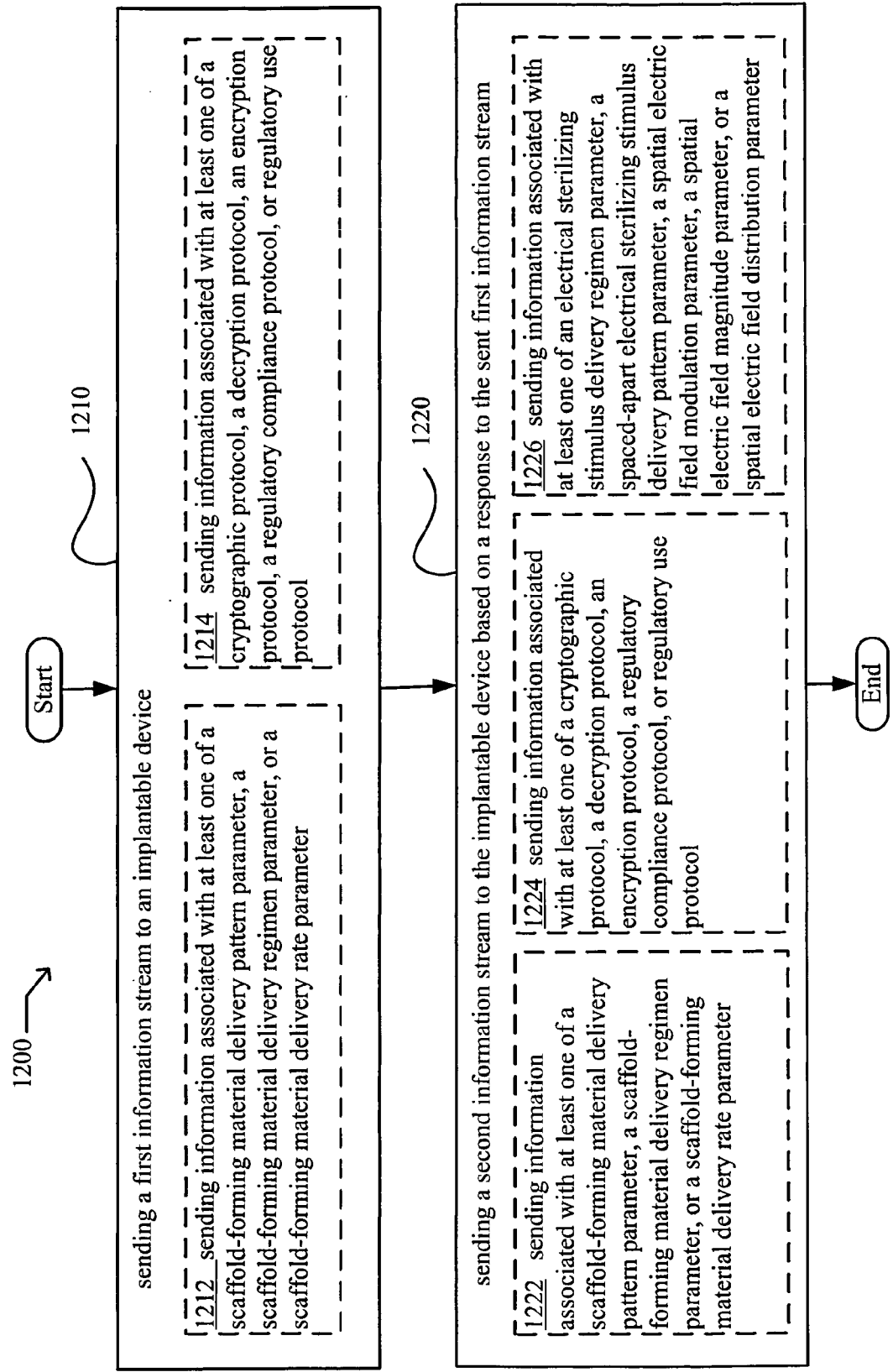
FIG. 12 is a flow diagram of a method according to one illustrated embodiment.

FIG. 12 shows an example of a method 1200.

At 1210, the method 1200 includes sending a first information stream to an implantable device 102. At 1212, sending the first information stream may include includes sending information associated with at least one of a scaffold-forming material delivery pattern parameter, a scaffold-forming material delivery regimen parameter, or a scaffold-forming material delivery rate parameter. At 1214, sending the first information stream may include sending information associated with at least one of a cryptographic protocol, a decryption protocol, an encryption protocol, a regulatory compliance protocol, or regulatory use protocol.

At 1220, the method 1200 includes sending a second information stream to the implantable device 102 based on a response to the sent first information stream. At 1222, sending the second information stream may include sending information associated with at least one of a scaffold-forming material delivery pattern parameter, a scaffold-forming material delivery regimen parameter, or a scaffold-forming material delivery rate parameter. At 1224, sending the second information stream may include sending information associated with at least one of a cryptographic protocol, a decryption protocol, an encryption protocol, a regulatory compliance protocol, or regulatory use protocol. At 1226, sending the second information stream may include sending information associated with at least one of a sterilizing stimulus delivery regimen parameter, a spaced-apart sterilizing stimulus delivery pattern parameter, a spatial electric field modulation parameter, a spatial electric field magnitude parameter, or a spatial electric field distribution parameter.

FIG. 13 shows an example of a method 1300.

At 1310, the method 1300 includes receiving information from an implantable device 102 that includes: a first outer surface 104, an actively-controllable excitation component 106 configured to deliver a sterilizing stimulus, in vivo, to tissue proximate the first outer surface of the implantable device 102, and a controller 130 communicatively coupled to the actively-controllable excitation component. At 1312, receiving information may include receiving at least one of a command, an update, data, or a code. At 1314, receiving information may include receiving information associated with at least one of an illumination pattern an excitation intensity, an excitation frequency, an excitation pulse frequency, an excitation pulse ratio, an excitation pulse intensity, an excitation pulse duration time, an excitation pulse repetition rate, an ON-rate, or an OFF-rate. At 1316, receiving information may include receiving information associated with an electrical sterilizing stimulus delivery regimen. At 1318, receiving information may include receiving information associated with at least one of a spaced-apart electrical sterilizing stimulus delivery pattern parameter, a spatial electric field modulation parameter, a spatial electric field magnitude parameter, or a spatial electric field distribution parameter. In an embodiment, receiving information may include receiving sensor data. In an embodiment, receiving information may include receiving a control signal. In an embodiment, receiving information may include receiving a request for transmission of information. In an embodiment, receiving information may include receiving a request for transmission of at least one of data, a command, an authorization, an update, or a code.

At 1320, the method 1300 may include generating a response based on the received information. At 1322, generating the response may include generating at least one of a response signal, an authentication response, an authorization response. At 1324, generating the response may include at least one of storing at least one parameter associated with the received information, storing at least a portion of the received information, or decrypting at least a portion of the received information. At 1326, generating the response may include at least one of initiating a cryptographic protocol, initiating a decryption protocol, or initiating an encryption protocol. In an embodiment, generating the response may include generating at least one of a control signal, data, a command, an authorization, an update, or a code.

Figure 14A:
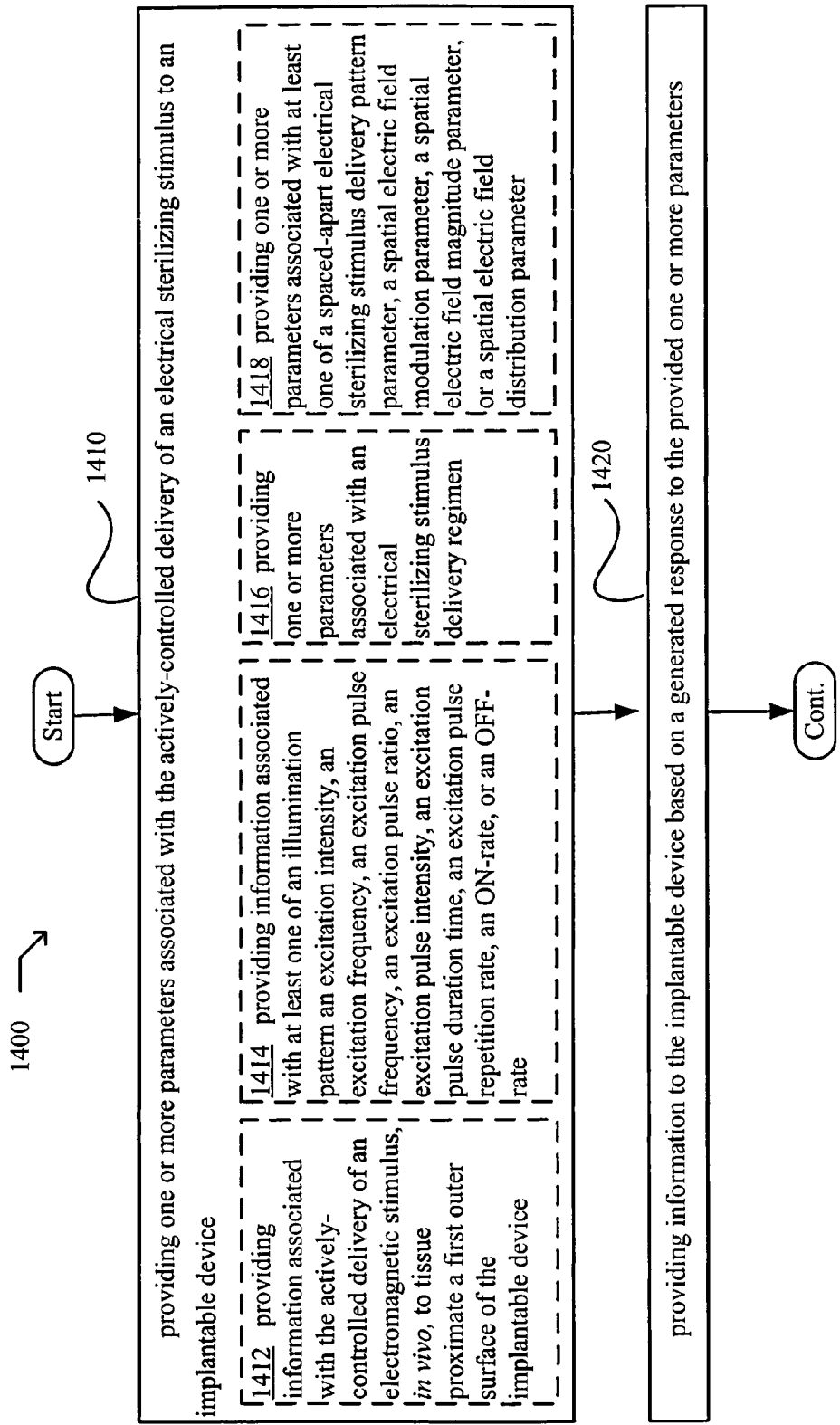
FIGS. 14A and 14B are flow diagrams of a method according to one illustrated embodiment.
Figure 14B:
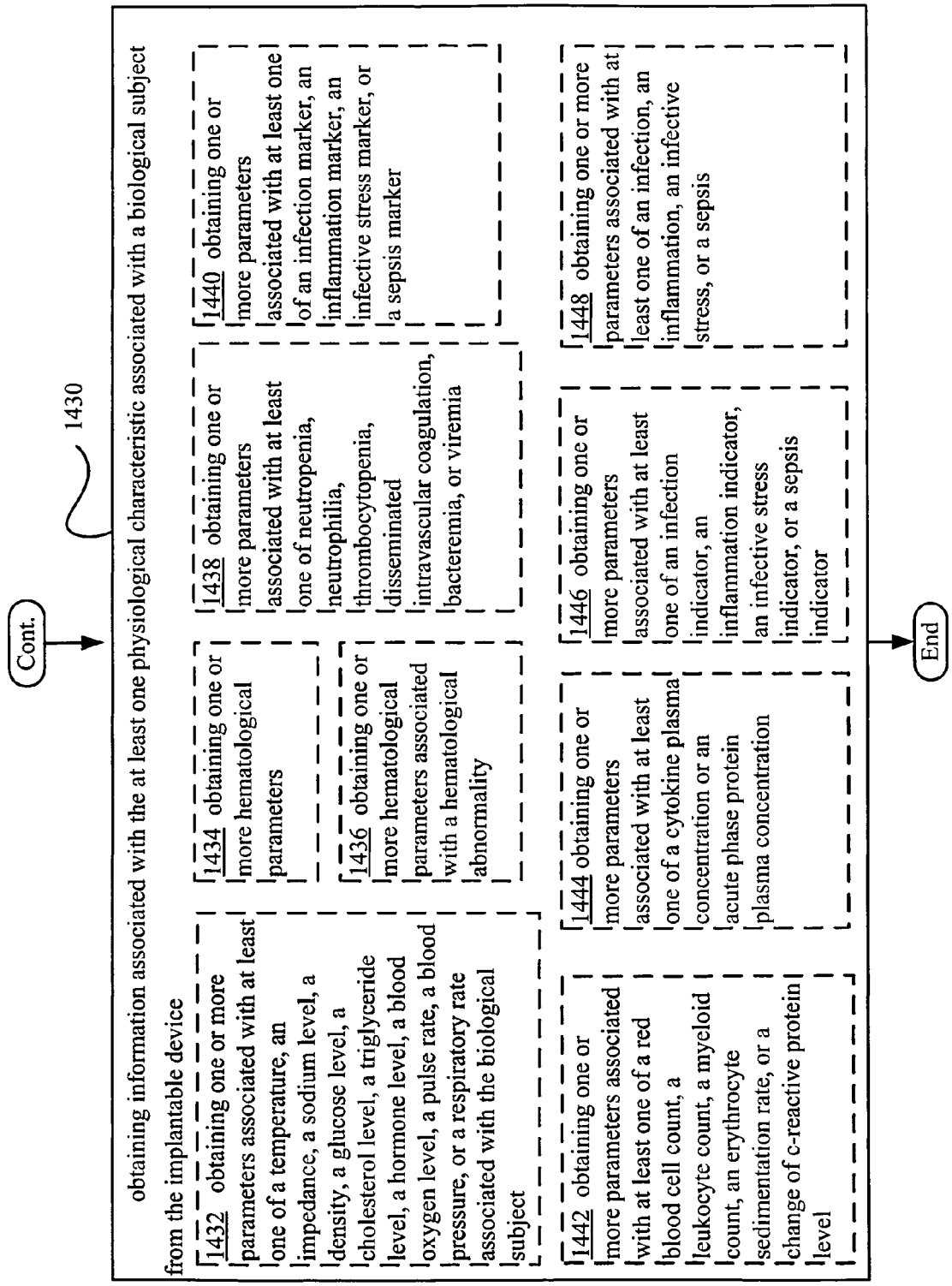

FIGS. 14A and 14B show an example of a method 1400.

At 1410, the method 1400 includes providing one or more parameters associated with the actively-controlled delivery of a sterilizing stimulus to an implantable device 102. In an embodiment, providing the one or more parameters includes providing information to the implantable device, the information associated with the actively-controlled delivery of at least one of an electrical sterilizing stimulus, an electromagnetic sterilizing stimulus, an ultrasonic sterilizing stimulus, or a thermal sterilizing stimulus, in vivo, to tissue proximate the implantable device. In an embodiment, providing the one or more parameters includes providing information associated with the actively-controlled delivery of an electrical stimulus, in vivo, to tissue proximate a first outer surface of the implantable device. At 1412, providing the one or more parameters may include providing information associated with the actively-controlled delivery of an electromagnetic stimulus, in vivo, to tissue proximate a first outer surface of the implantable device 102. At 1414, providing the one or more parameters may include providing information associated with at least one of an illumination pattern an excitation intensity, an excitation frequency, an excitation pulse frequency, an excitation pulse ratio, an excitation pulse intensity, an excitation pulse duration time, an excitation pulse repetition rate, an ON-rate, or an OFF-rate. At 1416, providing the one or more parameters may include providing one or more parameters associated with an electrical sterilizing stimulus delivery regimen. At 1418, providing the one or more parameters may include providing one or more parameters associated with at least one of a spaced-apart electrical sterilizing stimulus delivery pattern parameter, a spatial electric field modulation parameter, a spatial electric field magnitude parameter, or a spatial electric field distribution parameter. In an embodiment, providing the one or more parameters includes providing information associated with the actively-controlled delivery of an ultrasonic stimulus, in vivo, to tissue proximate a first outer surface of the implantable device. In an embodiment, providing the one or more parameters includes providing information associated with the actively-controlled delivery of a thermal stimulus, in vivo, to tissue proximate a first outer surface of the implantable device. In an embodiment, providing the one or more parameters includes providing information associated with a spatial-pattern of the sterilizing stimulus. In an embodiment, providing the one or more parameters includes providing information associated with a spatial-pattern distribution of the sterilizing stimulus. In an embodiment, providing the one or more parameters includes providing information associated with a temporal-pattern of the sterilizing stimulus. In an embodiment, providing the one or more parameters includes providing the one or more parameters based at least in part on obtained information.

At 1420 the method 1400 may includes providing information to the implantable device 102 based on a generated response to the provided one or more parameters. In an embodiment, providing the one or more parameters includes providing the one or more parameters based at least in part on obtained information. In an embodiment, providing the one or more parameters includes providing the one or more parameters in response to the obtained information.

At 1430, the method 1400 may include obtaining information associated with the at least one physiological characteristic associated with a biological subject from the implantable device 102. At 1432, obtaining information may include obtaining one or more parameters associated with at least one of a temperature, an impedance, a sodium level, a density, a glucose level, a lipoprotein level, a cholesterol level, a triglyceride level, a hormone level, a blood oxygen level, a pulse rate, a blood pressure, or a respiratory rate associated with the biological subject. At 1434, obtaining information may include obtaining one or more hematological parameters. At 1436, obtaining information may include includes obtaining one or more hematological parameters associated with a hematological abnormality. At 1438, obtaining information may include obtaining one or more parameters associated with at least one of leukopenia, leukophilia, lymphocytopenia, lymphocytophilia, neutropenia, neutrophilia, thrombocytopenia, disseminated intravascular coagulation, bacteremia, or viremia. At 1440, obtaining information may include obtaining one or more parameters associated with at least one of an infection marker, an inflammation marker, an infective stress marker, a systemic inflammatory response syndrome marker, or a sepsis marker. At 1442, obtaining information may include obtaining one or more parameters associated with at least one of a red blood cell count, a lymphocyte count, a lymphocyte count, a leukocyte count, a myeloid count, an erythrocyte sedimentation rate, or a change of C-reactive protein level. At 1444, obtaining information may include obtaining one or more parameters associated with at least one of a cytokine plasma concentration or an acute phase protein plasma concentration. At 1446, obtaining information may include obtaining one or more parameters associated with at least one of an infection indicator, an inflammation indicator, an infective stress indicator, a systemic inflammatory response syndrome indicator, or a sepsis indicator. At 1448, obtaining information may include obtaining one or more parameters associated with at least one of an infection, an inflammation, an infective stress, systemic inflammatory response syndrome, or a sepsis. In an embodiment, obtaining information may include obtaining one or more parameters associated with at least one of an infection, an inflammation, an infective stress, a systemic inflammatory response syndrome, or a sepsis.

Figure 15:
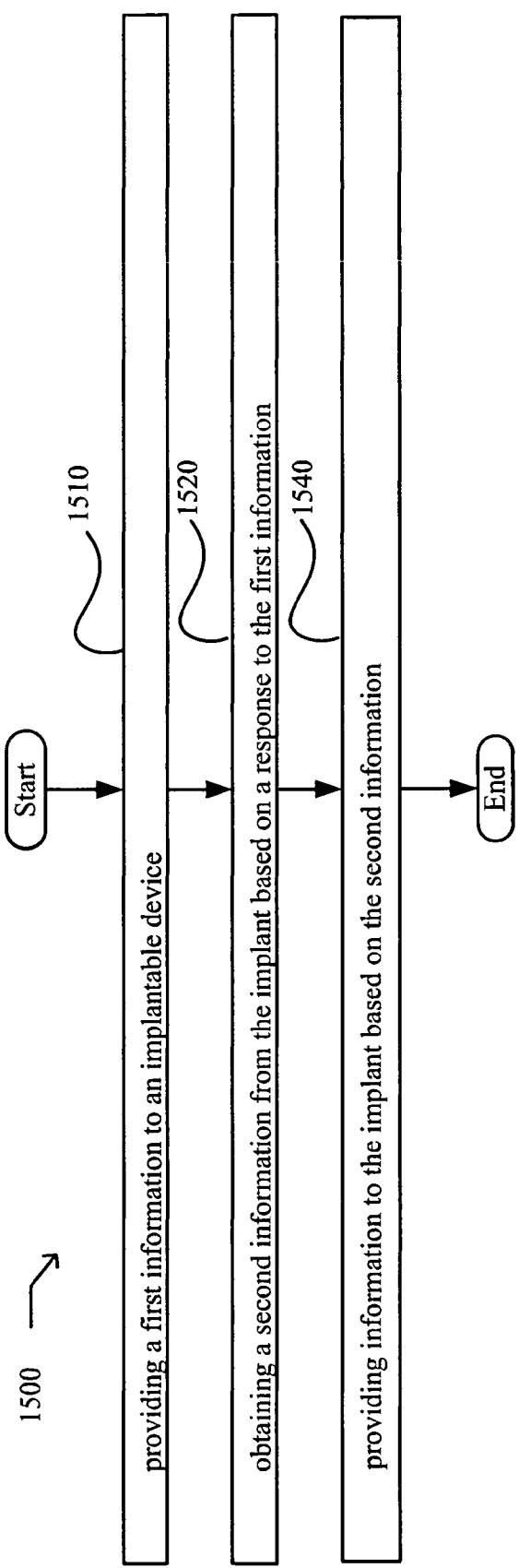
FIG. 15 is a flow diagram of a method according to one illustrated embodiment.

FIG. 15 shows an example of a method 1500.

At 1510, the method 1500 includes providing a first information to an implantable device 102. At 1520, the method 1500 includes obtaining a second information from the implant based on a response to the first information. At 1530, the method 1500 includes providing information to the implant based on the second information.

FIG. 16 shows an example of a method 1600.

At 1610, the method 1600 includes receiving information from an implantable device 102, during delivery of a sterilizing stimulus, in vivo, to tissue proximate a first outer surface of the implantable device 102. At 1620, the method 1600 includes generating a response based on the received information.

FIG. 17 shows an example of a method 1700.

At 1710, the method 1700 includes receiving information from an implantable device 102, after delivery of a sterilizing stimulus, in vivo, to tissue proximate a first outer surface of the implantable device 102. At 1720, the method 1700 includes generating a response based on the received information.

Figure 18:
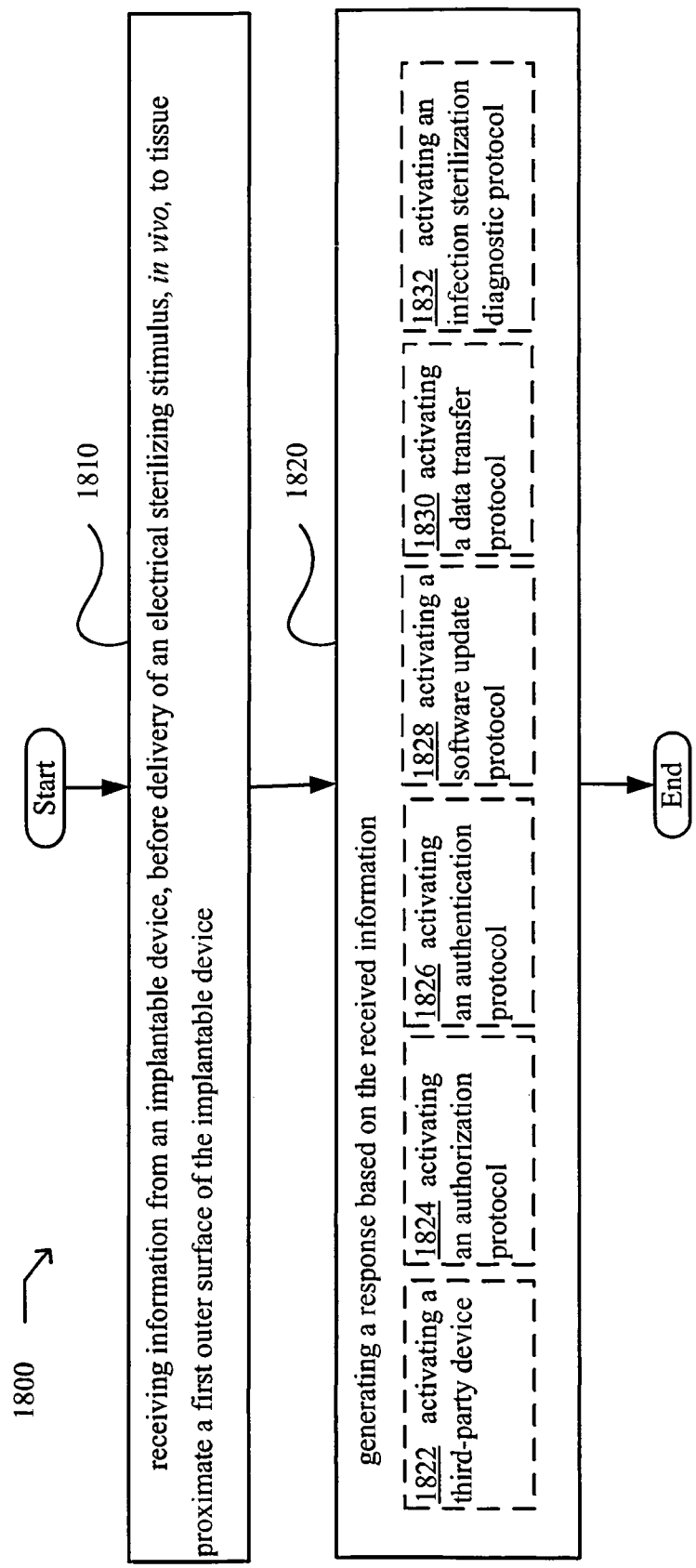
FIG. 18 is a flow diagram of a method according to one illustrated embodiment.

FIG. 18 shows an example of a method 1800.

At 1810, the method 1800 includes receiving information from an implantable device 102, before delivery of a sterilizing stimulus, in vivo, to tissue proximate a first outer surface of the implantable device 102. At 1820, the method 1800 includes generating a response based on the received information. At 1822, generating the response may include activating a third-party device. At 1824, generating the response may include activating an authorization protocol. At 1826, generating the response may include activating an authentication protocol. At 1828, generating the response may include activating a software update protocol. At 1830, generating the response may include activating a data transfer protocol. At 1832, generating the response may include activating an infection sterilization diagnostic protocol.

Figure 19:
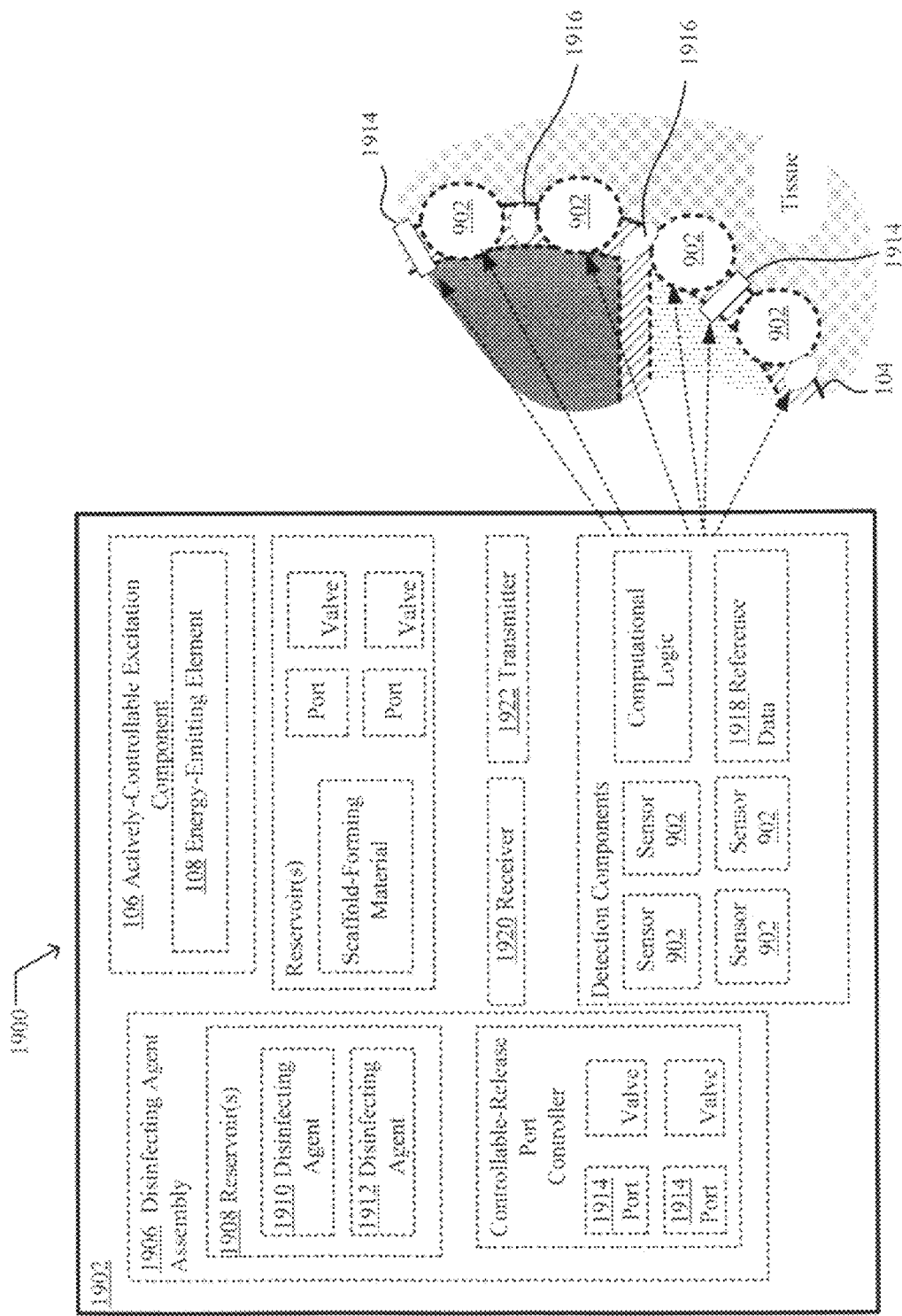
FIG. 19 is a schematic diagram of a system including an implantable medical device according to one illustrated embodiment.

FIG. 19 shows a system 1900 in which one or more methodologies or technologies may be implemented such as, for example, actively, sensing, treating, or preventing an infection (e.g., an implant-associated infection, hematogenous implant-associated infection, and the like), a hematological abnormality, and the like, or for implementing any of the disclosed methods or processes.

The system 1900 can include, but is not limited to, one or more implantable medical devices 1902. In an embodiment, the implantable medical device 1902 includes, but is not limited to, a body having at least one outer surface 104, and one or more disinfecting agent assemblies 1906 including at least one disinfecting active agent reservoir 1908. In an embodiment, the disinfecting agent assembly 1906 is configured to deliver at least one disinfecting agent 1910 from the at least one disinfecting active agent reservoir 1908 to tissue proximate the at least one outer surface 104 of the implantable medical device 1902. In an embodiment, the disinfecting agent assembly 1906 is configured to deliver the at least one disinfecting agent 1910 in a spatially-patterned distribution.

In an embodiment, the disinfecting agent assembly 1906 is configured to deliver at least one energy-activateable disinfecting agent 1912 from the at least one disinfecting active agent reservoir 1908 to tissue proximate the at least one outer surface 104 of the implantable medical device 1902. In an embodiment, the disinfecting agent assembly 1906 is configured to deliver the at least one energy-activateable disinfecting agent 1912 in a spatially-patterned distribution.

Among disinfecting agents, examples include, but are not limited to, energy (e.g., chemical energy, electrical resistance, laser energy, microwave energy, optical energy, radio frequency energy, sonic energy, thermal energy, thermal resistance heating energy or ultrasonic energy, or the like)-activateable disinfecting agents, and the like. Non-limiting examples of energy-activateable disinfecting agents include radiation absorbers, light energy absorbers, X-ray absorbers, photoactive agents, and the like. Non-limiting examples of photoactive agents include, but are not limited to photoactive antimicrobial agents (e.g., eudistomin, photoactive porphyrins, photoactive $TiO_2$, antibiotics, silver ions, antibodies, nitric oxide, and the like), photoactive antibacterial agents, photoactive antifungal agents, and the like.

Further examples of disinfecting agents include, but are not limited to, triplet excited-state photosensitizers, reactive oxygen species, reactive nitrogen species, any other inorganic or organic ion or molecules that include oxygen ions, free radicals, peroxides, or the like.

In an embodiment, the at least one energy-activateable disinfecting agent includes at least one photoactive agent, or a metabolic precursor thereof. In an embodiment, the at least one energy-activateable disinfecting agent includes at least one X-ray absorber. In an embodiment, the at least one energy-activateable disinfecting agent includes at least one radiation absorber.

Further non-limiting examples of disinfecting agents include compounds, molecules, or treatments that elicit a biological response from any biological subject. Further non-limiting examples of disinfecting agents include therapeutic agents (e.g., antimicrobial therapeutic agents), pharmaceuticals (e.g., a drug, a therapeutic compound, pharmaceutical salts, and the like) non-pharmaceuticals (e.g., a cosmetic substance, and the like), neutraceuticals, antioxidants, phytochemicals, homeopathic agents, and the like. Further non-limiting examples of disinfecting agents include peroxidases (e.g., haloperoxidases such as chloroperoxidase, and the like), oxidoreductase (e.g., myeloperoxidase, eosinophil peroxidase, lactoperoxidase, and the like) oxidases, and the like.

Further non-limiting examples of disinfecting agents include one or more pore-forming toxins. Non limiting Examples of pore-forming toxins include beta-pore-forming toxins, e.g., hemolysin, Panton-Valentine leukocidin S, aerolysin, Clostridial epsilon-toxin; binary toxins, e.g., anthrax, C. perfringens iota toxin, C. difficile cytolethal toxins; cholesterol-dependent cytolysins; pneumolysin; small pore-forming toxins; and gramicidin A.

Further non-limiting examples of disinfecting agents include one or more pore-forming antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. More than 800 different antimicrobial peptides have been identified or predicted from nucleic acid sequences, a subset of which have are available in a public database (see, e.g., Wang & Wang, *Nucleic Acids Res.* 32:D590-D592, 2004); http://aps.unmc.edu/AP/main.php, which is incorporated herein by reference). More specific examples of antimicrobial peptides include, but are not limited to, anionic peptides, e.g., maximin H5 from amphibians, small anionic peptides rich in glutamic and aspartic acids from sheep, cattle and humans, and dermcidin from humans; linear cationic alpha-helical peptides, e.g., cecropins (A), andropin, moricin, ceratotoxin, and melittin from insects, cecropin P1 from *Ascaris nematodes*, magainin (2), dermaseptin, bombinin, brevinin-1, esculentins and buforin II from amphibians, pleurocidin from skin mucous secretions of the winter flounder, seminalplasmin, BMAP, SMAP (SMAP29, ovispirin), PMAP from cattle, sheep and pigs, CAP18 from rabbits and LL37 from humans; cationic peptides enriched for specific amino acids, e.g., praline-containing peptides including abaecin from honeybees, praline- and arginine-containing peptides including apidaecins from honeybees, drosocin from *Drosophila*, pyrrhocoricin from European sap-sucking bug, bactenicins from cattle (Bac7), sheep and goats and PR-39 from pigs, praline- and phenylalanine-containing peptides including prophenin from pigs, glycine-containing peptides including hymenoptaecin from honeybees, glycine- and praline-containing peptides including coleoptericin and holotricin from beetles, tryptophan-containing peptides including indolicidin from cattle, and small histidine-rich salivary polypeptides, including histatins from humans and higher primates; anionic and cationic peptides that contain cysteine and from disulfide bonds, e.g., peptides with one disulphide bond including brevinins, peptides with two disulfide bonds including alpha-defensins from humans (HNP-1, HNP-2, cryptidins), rabbits (NP-1) and rats, beta-defensins from humans (HBD1, DEFB118), cattle, mice, rats, pigs, goats and poultry, and rhesus theta-defensin (RTD-1) from rhesus monkey, insect defensins (defensin A); and anionic and cationic peptide fragments of larger proteins, e.g., lactoferricin from lactoferrin, casocidin 1 from human casein, and antimicrobial domains from bovine alpha-lactalbumin, human hemoglobin, lysozyme, and ovalbumin (see, e.g., Brogden, *Nat. Rev. Microbiol.* 3:238-250, 2005, which is incorporated herein by reference).

Further non-limiting examples of disinfecting agents include antibacterial drugs. Non-limiting examples of antibacterial drugs include beta-lactam compounds such as penicillin, methicillin, nafcillin, oxacillin, cloxacillin, dicloxacillin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, silfamethizole, sulfadiazine, sulfamethoxazole, sulfapyridine, and sulfadoxine; fluoroquinolones such as ciprofloxacin, gatifloxacin, gemifloxacin, levofloxacin, lomefloxacin, moxifloxacin, norfloxacin, and ofloxacin; antimycobacteria drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole.

Further non-limiting examples of disinfecting agents include antifungal agents. Non-limiting examples of antifungal agents include anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

Further non-limiting examples of disinfecting agents include anti-parasite agents. Non-limiting examples of anti-parasite agents include antimalaria drugs such as chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins; treatments for amebiasis such as metronidazole, iodoquinol, paromomycin, diloxanide furoate, pentamidine, sodium stibogluconate, emetine, and dehydroemetine; and other anti-parasite agents such as pentamidine, nitazoxanide, suramin, melarsoprol, eflornithine, nifurtimox, clindamycin, albendazole, and tinidazole.

In an embodiment, the antimicrobial agent may be an antimicrobial peptide. Amino acid sequence information for a subset of these may be found as part of a public database (see, e.g., Wang & Wang, *Nucleic Acids Res.* 32:D590-D592, 2004); http://aps.unmc.edu/AP/main.php, which is incorporated herein by reference). Alternatively, a phage library of random peptides may be used to screen for peptides with antimicrobial properties against live bacteria, fungi and/or parasites. The DNA sequence corresponding to an antimicrobial peptide may be generated ex vivo using standard recombinant DNA and protein purification techniques.

In an embodiment, the disinfecting agents include, but are not limited to oxidizing chemicals suitable to disrupt or destroy cell membranes. For example, some oxidizing chemicals may withdraw electrons from a cell membrane causing it to, for example, become destabilized. Destroying the integrity of cell membranes of, for example, a pathogen may lead to cell death.

The at least one active agent reservoir 1908 can include, for example, but not limited to an acceptable carrier. In an embodiment, the at least one energy-activateable disinfecting agent 1912 is carried by, encapsulated in, or forms part of, an energy-sensitive (e.g., energy-activateable), carrier, vehicle, vesicle, pharmaceutically vehicle, pharmaceutically carrier, pharmaceutically acceptable vehicle, pharmaceutically acceptable carrier, or the like.

Non-limiting examples of carriers include any matrix that allows for transport of, for example, a disinfecting agent across any tissue, cell membranes, and the like of a biological subject, or that is suitable for use in contacting a biological subject, or that allows for controlled release formulations of the compositions disclosed herein. Further non-limiting examples of carriers include at least one of creams, liquids, lotions, emulsions, diluents, fluid ointment bases, gels, organic and inorganic solvents, degradable or non-degradable polymers, pastes, salves, vesicle, and the like. Further non-limiting examples of carriers include cyclic oligosaccharides, ethasomes, hydrogels, liposomes, micelle, microspheres, nisomes, non-ionic surfactant vesicles, organogels, phospholipid surfactant vesicles, phospholipid surfactant vesicles, transfersomes, virosomes. Further non-limiting examples of energy-sensitive carriers and the like include electrical energy-sensitive, light sensitive, pH-sensitive, ion-sensitive, sonic energy sensitive, ultrasonic energy sensitive carriers. Further non-limiting examples of energy-sensitive carriers and the like include cavitationally activated drug delivery carriers, acoustically activated drug delivery carries, and the like In an embodiment, the at least one energy-activateable disinfecting agent 1912 is carried by energy-sensitive vesicles (e.g., energy-sensitive cyclic oligosaccharides, etha-somes, hydrogels, liposomes, micelles, microspheres, nisomes, non-ionic surfactant vesicles, organogels, phospholipid surfactant vesicles, transfersomes, virosomes, and the like.). In an embodiment, at least one of the one or more energy-emitting elements 108 is configured to provide energy of a character and for a time sufficient to liberate at least a portion of the disinfecting agent carried by the energy-sensitive vesicles.

In an embodiment, the at least one energy-activateable disinfecting agent includes at least one active agent that selectively targets bacteria. For example, in an embodiment, the at least one energy-activateable disinfecting agent 1912 includes at least one bacteriophage that may, for example, selectively target bacteria. Bacteriophages generally comprise an outer protein hull enclosing genetic material. The genetic material can be ssRNA, dsRNA, ssDNA, or dsDNA. Bacteriophages are generally smaller than the bacteria they destroy generally ranging from about 20 nm to about 200 nm. Non-limiting examples of bacteriophages include T2, T4, T6, phiX-174, MS2, and the like).

In an embodiment, the implantable medical device 1902 includes a plurality of spaced apart release ports 1914 adapted to deliver the at least one energy-activateable disinfecting agent 1912 in a spatially-patterned distribution. In an embodiment, the implantable medical device 1902 includes a plurality of spaced apart controllable-release ports 1916 adapted to deliver the at least one energy-activateable disinfecting agent 1912 in a spatially-patterned distribution. In an embodiment, the controller is operably coupled to the disinfecting agent assembly and configured to control at least one of a disinfecting agent delivery rate, a disinfecting agent delivery amount, a disinfecting agent delivery composition, a port release rate, a port release amount, or a port release pattern. In an embodiment, the controller is operably coupled to the disinfecting agent assembly and configured to actively control one or more of the plurality of spaced apart release ports.

In an embodiment, the disinfecting agent assembly 1906 is configured to deliver at least one energy-activateable steroid to tissue proximate the at least one outer surface 104 of the implantable medical device 1902.

In an embodiment, the implantable medical device 1902 includes for example, but not limited to, one or more energy-emitting elements 108. In an embodiment, a controller 130 communicatively coupled to the one or more energy-emitting elements 108, and is configured to regulate at least one of an illumination intensity, an energy-emitting pattern, a peak emission wavelength, an ON-pulse duration, an OFF-pulse duration, or a pulse frequency of the one or more energy-emitting elements 108. In an embodiment, the one or more energy-emitting elements 108 include at least one of a laser, a laser diode, a light-emitting diode, an arc flashlamp, or a continuous wave bulb. In an embodiment, the one or more energy-emitting elements 108 include at least one of a light-emitting diode, a quantum dot, an organic light-emitting diode, or a polymer light-emitting diode.

In an embodiment, the one or more energy-emitting elements 108 are configured to emit electromagnetic radiation having a peak emission wavelength in the x-ray, ultraviolet, visible, infrared, near infrared, microwave, or radio frequency spectrum, or combinations thereof. In an embodiment, the one or more energy-emitting elements 108 are operable to emit a sufficient amount of electromagnetic radiation to increase the temperature of at least a portion of the tissue proximate the at least one outer surface 104 of the implantable medical device 1902 by about 5° C. to about 20° C. In an embodiment, the one or more energy-emitting elements are operable to emit optical energy having one or more peak emission wavelengths in the infrared, visible, or ultraviolet spectrum, or combinations thereof.

In an embodiment, the one or more energy-emitting elements are configured to provide a spatially-patterned sterilizing stimulus. In an embodiment, the one or more energy-emitting elements are configured to provide a sterilizing stimulus pattern comprising at least a first region and a second region, the second region having at least one of an illumination intensity, an energy-emitting pattern, a peak emission wavelength, an ON-pulse duration, an OFF-pulse duration, or a pulse frequency different than the first region.

In an embodiment, it may be possible to, for example, monitor the delivery of the one or more disinfecting agents. In an embodiment, it may be possible to, for example, detect the concentration or location of the one or more disinfecting agents within tissue proximate the one or more implantable medical devices 1902. In an embodiment, it may be possible to, for example, detect the concentration or location of the one or more disinfecting agents within tissue proximate the one or more implantable medical devices 1902 prior, during, or after delivery, of a sterilizing stimulus. In an embodiment, it may be possible to, for example, detect a spatially-patterned distribution of the one or more disinfecting agents using one or more tracer agents.

The system 1900 can include, but is not limited to, one or more tracer agent delivery assemblies configured to deliver one or more tracer agents. In an embodiment, the disinfecting agent assembly 1906 is configured to deliver one or more tracer agents. In an embodiment, disinfecting agent assembly 1906 is further configured to concurrently or sequentially deliver one or more tracer agents and one or more one energy-activateable disinfecting agents. In an embodiments, the disinfecting agent assembly 1906 is further configured to deliver one or more tracer agents for indicating the presence or concentration of one or more one energy-activateable disinfecting agents in at least a portion of tissue proximate the implantable medical device 1902. In an embodiment, the disinfecting agent assembly 1906 is further configured to deliver one or more tracer agents for indicating the response of the one or more one energy-activateable disinfecting agents to energy emitted from the one or more energy-emitting elements 108.

Among tracer agents, examples include one or more in vivo clearance agents, magnetic resonance imaging agents, contrast agents, dye-peptide compositions, fluorescent dyes, or tissue specific imaging agents. In an embodiments, the one or more tracer agent include at least one fluorescent dye. In an embodiments, the one or more tracer agent includes indocyanine green.

The system can include for example, but not limited to, a power source 700, the power source 700 including at least one of a thermoelectric generator 704, piezoelectric generator 706, an electromechanical generator 708, or a biomechanical-energy harvesting generator 710.

The system 1900 can include for example, but not limited to, a power source 700, the power source 700 electromagnetically, magnetically, ultrasonically, optically, inductively, electrically, or capacitively-coupled to the actively-controllable excitation component. In an embodiment, the power source 700 is carried by the implantable medical device. In an embodiment, power source 700 comprises at least one of a button cell, a chemical battery cell, a fuel cell, a secondary cell, a lithium ion cell, a micro-electric patch, a nickel metal hydride cell, silver-zinc cell, a capacitor, a super-capacitor, a thin film secondary cell, an ultra-capacitor, or a zinc-air cell.

The system 1900 can include for example, but not limited to, one or more sensors 902 configured to determine at least one characteristic associated with the tissue proximate the at least one outer surface 104. In an embodiment, the at least one characteristic associated with the tissue proximate the at least one outer surface 104 includes at least one of an inflammation indication parameter, an infection indication parameter, a diseased state indication parameter, or a diseased tissue indication parameter. In an embodiment, the at least one characteristic associated with the tissue proximate the at least one outer surface 104 includes at least one of an inflammation indication parameter, an infection indication parameter, a diseased state indication parameter, or a diseased tissue indication parameter. In an embodiment, the at least one characteristic associated with the tissue proximate the at least one outer surface 104 includes at least one parameter associated with an amount of energy-activateable disinfecting agent present in at least a portion of the tissue proximate the at least one outer surface 104, a sodium ion content, a chloride content, a superoxide anion content, or a hydrogen peroxide content. In an embodiment, the at least one characteristic associated with the tissue proximate the at least one outer surface 104 includes at least one of an absorption coefficient, an extinction coefficient, or a scattering coefficient.

In an embodiment, the at least one characteristic associated with the tissue proximate the at least one outer surface 104 includes at least one parameter associated with an infection marker, an inflammation marker, an infective stress marker, or a sepsis marker. In an embodiment, the infection marker includes at least one of a red blood cell count, a lymphocyte count, a leukocyte count, a myeloid count, an erythrocyte sedimentation rate, or a C-reactive protein level.

In an embodiment, the at least one characteristic associated with the tissue proximate the at least one outer surface 104 includes at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, or a pH level. In an embodiment, the at least one characteristic associated with the tissue proximate the at least one outer surface 104 includes at least one parameter associated with a cytokine plasma concentration or an acute phase protein plasma concentration. In an embodiment, the at least one characteristic associated with the tissue proximate the at least one outer surface 104 includes at least one parameter associated with a leukocyte level. In an embodiment, the controller is communicatively coupled to the one or more sensors 902 configured to determine the at least one characteristic associated with the tissue proximate the at least one outer surface 104. In an embodiment, the controller is configured to perform a comparison of the at least one characteristic associated with the tissue proximate the at least one outer surface 104 to stored reference data, and to generate a response based at least in part on the comparison.

The system 1900 can include for example, but not limited to, one or more processors configured to perform a comparison of the at least one characteristic associated with the tissue proximate the at least one outer surface 104 to stored reference data 1918, and to generate a response based at least in part on the comparison. In an embodiment, the generated response includes at least one parameter associated with delivery of the energy-activateable disinfecting agent 1912. The system 1900 can include for example, but not limited to, circuitry for obtaining information; and circuitry for storing the obtained information. In an embodiment, the circuitry for obtaining information includes circuitry for obtaining information associated with a delivery of the sterilizing stimulus. In an embodiment, the circuitry for obtaining information includes circuitry for obtaining at least one of a command stream, a software stream, or a data stream. The system 1900 can include for example, but not limited to, one or more processors configured to perform a comparison of the determined at least one physiological characteristic of the biological subject to the obtained information, and to generate a response based at least in part on the comparison. The system 1900 can include for example, but not limited to, at least one receiver 1920 configured to acquire information. In an embodiment, the at least one receiver 1920 is configured to acquire at least one of instructions, information associated with a delivery of the sterilizing stimulus, acquire data, acquire software. The system 1900 can include for example, but not limited to, circuitry for providing information. In an embodiment, the circuitry for providing information includes circuitry for providing information regarding at least one characteristic associated with a tissue proximate the first outer surface. The system 100 can include for example, but not limited to, at least one transmitter 1922 configured to send information. In an embodiment, the at least one transmitter 1922 is configure to report actions (e.g., detected health status, disease status, treatment actions, treatment response, and the like).

Figure 20:
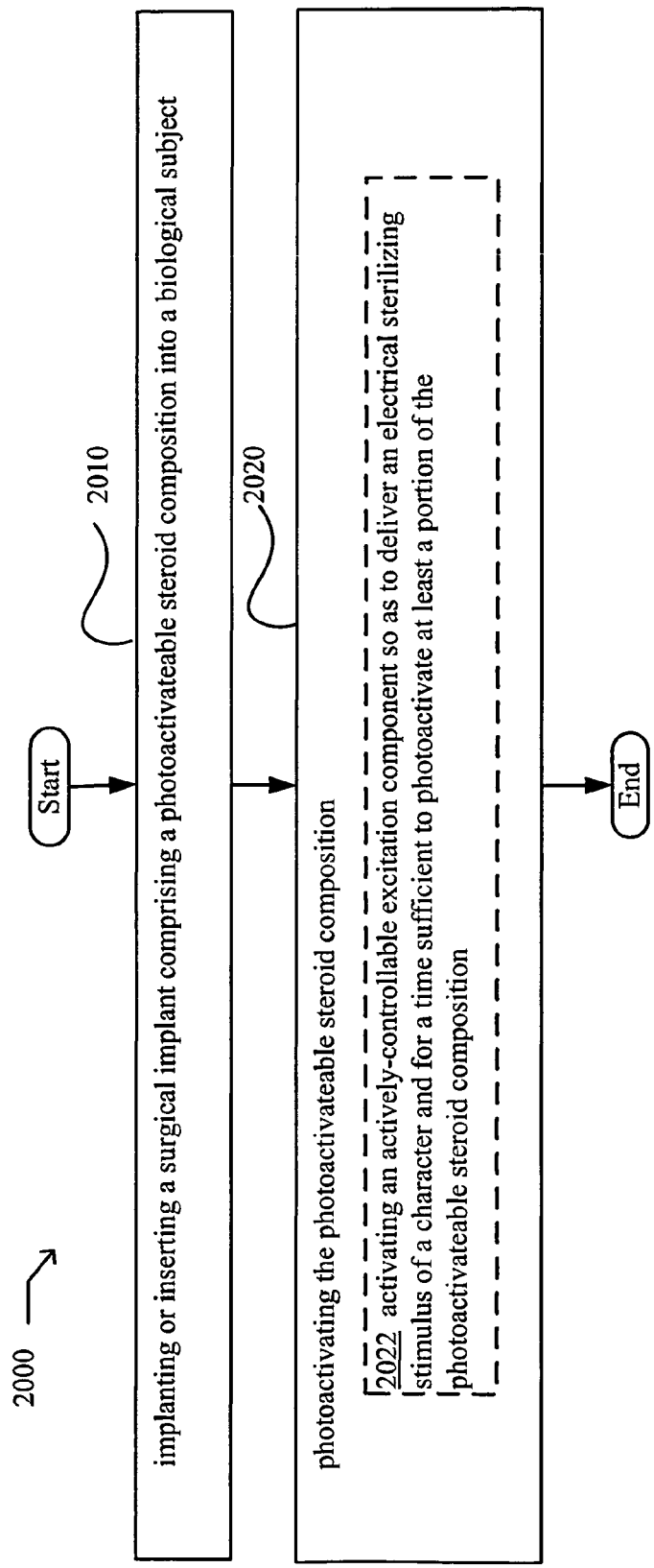
FIG. 20 is a flow diagram of a method of treating scar formation post surgery according to one illustrated embodiment.

FIG. 20 shows an example of a method 2000 of treating scar formation post surgery.

Following an injury to a tissue, localized release of inflammatory mediators may occur as a result of damaged endothelial cells and platelet aggregation at the site of injury. This inflammatory response is a normal part of the wound repair process, preventing infection and promoting fibrosis and wound closure. Inflammatory mediators such as transforming growth factor (TGF) β family, platelet-derived growth factors (PDGF), and epidermal growth factors (EGF) stimulate fibroblast proliferation and matrix secretion, and promote leukocyte recruitment. The recruited leukocytes release additional mediators such as fibroblast growth factors (FGF), vascular endothelial growth factors (VEGF), and other factors that reinforce fibroblast proliferation and differentiation, fight infection, and increase vascular permeability and ingrowth. Although important in the wound healing process, inflammatory mediators such as TGF-β have been implicated in scar formation. Accordingly, it may be possible to attenuate scar formation by regulating the activity of mediators involved in the wound repair process.

In an embodiment, astroglial cells, in their immature, activated state, may be used to reduce secondary cell death (necrosis) glial scar formation, promote axon regeneration, or promote blood vessel growth. See e.g., U.S. Pat. No. 4,900,553. For example, in an embodiment, a method of reducing glial scar formation includes inducing apoptosis in reactive astrocytes (e.g., microglia, endothelial cells, fibroblasts, or the like), providing one or more neural stem cells, nonreactive astrocytes or the like, and providing a stimulus (an electrical an electromagnetic an ultrasonic or a thermal stimulus, or the like) of a character and duration to promote growth of the one or more neural stem cells, or nonreactive astrocytes.

At 2010, the method 2000 includes implanting or inserting a surgical implant comprising a photoactivateable steroid composition into a biological subject. In an embodiment, implanting or inserting the surgical implant can include implanting or inserting a surgical implant comprising a photoactivateable steroid composition including one or more growth promoting materials. At 2020, the method 2000 includes photoactivating the photoactivateable steroid composition. At 2022, photoactivating the photoactivateable steroid composition may include controlling an actively-controllable excitation component 106 so as to deliver a sterilizing stimulus of a character and for a time sufficient to photoactivate at least a portion of the photoactivateable steroid composition. In an embodiment, photoactivating the photoactivateable steroid composition can include controlling an actively-controllable excitation component so as to deliver a sterilizing stimulus of a character and for a time sufficient to stimulate non-scaring tissue formation.

In an embodiment, the method 2000 may further include concurrently or sequentially delivering a first electrical stimulus and a second electrical stimulus, in vivo, to target tissue proximate the implanted or inserted surgical implant. In an embodiment, the first electrical stimulus or the second electric stimulus is of a character and duration to inhibit growth of tissue of a first type, and the other of the first electrical stimulus or the second electric stimulus is of a character and duration to promote growth of tissue of a second type. In an embodiment, the method 2000 may include concurrently or sequentially delivering a first electrical stimulus and a second electrical stimulus, in vivo, to target tissue proximate the implanted or inserted surgical implant, such that the first electrical stimulus or the second electric stimulus is of a character and duration to inhibit (e.g., minimize, reduce, prevent, or the like) a scar formation process, and the other of the first electrical stimulus or the second electric stimulus is of a character and duration to promote growth of tissue. In an embodiment, the method 2000 may further include concurrently or sequentially delivering a spatially patterned electrical stimulus including a first electrical stimulus and a second electrical stimulus, in vivo, to target tissue proximate the implanted or inserted surgical implant, the first electrical stimulus or the second electric stimulus of a character and duration to inhibit scar formation in a first region proximate the implanted device and the other of the first electrical stimulus or the second electric stimulus of a character and duration to promote growth of tissue in a second region proximate the implanted, the second region differing in at least one of area, volume, or location of the first region.

Figure 21:
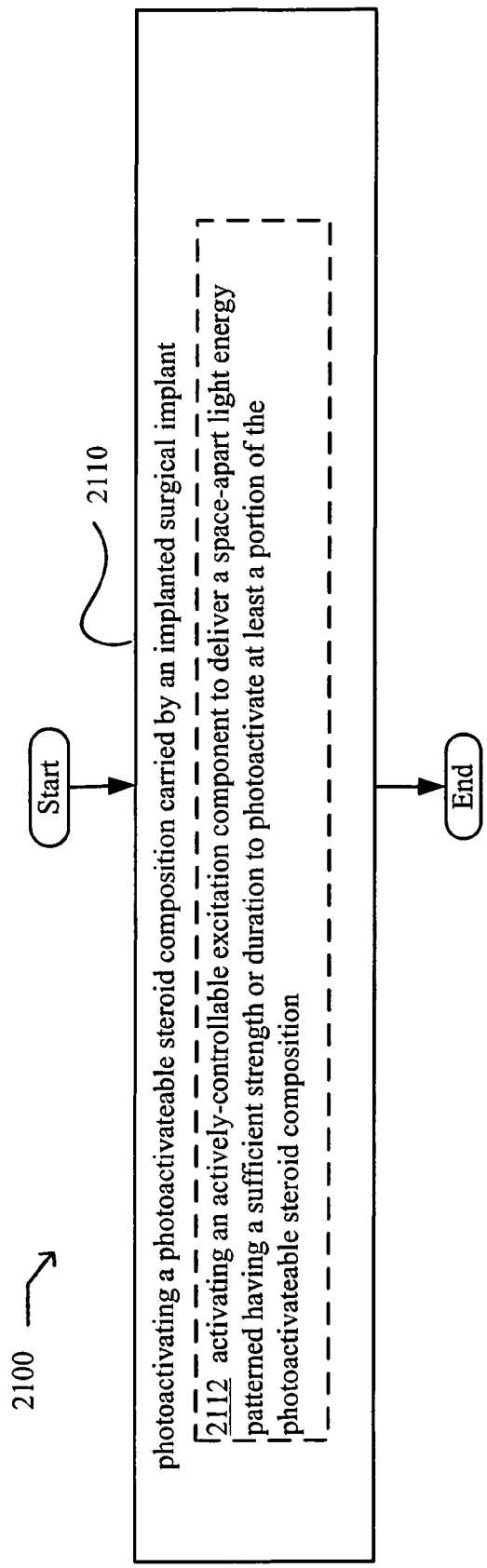
FIG. 21 is a flow diagram of a method of treating scar formation post surgery according to one illustrated embodiment.

FIG. 21 shows an example of a method 2100 of treating scar formation post surgery.

At 2110, the method 2100 includes photoactivating a photoactivateable steroid composition carried by an implanted surgical implant. At 2112, photoactivating the photoactivateable steroid composition may include activating an actively-controllable excitation component 106 to deliver a space-apart light energy patterned having a sufficient strength or duration to photoactivate at least a portion of the photoactivateable steroid composition.

Referring to FIG. 22, a powered surgical implant 2202 can include for example, but not limited to, a plurality of electrodes 118. In an embodiment, the plurality of electrodes 188 are configured to energize an aqueous salt composition in the presence of an applied potential. The powered surgical implant 2202 can include for example, but not limited to, a power source 700 electromagnetically, magnetically, ultrasonically, optically, inductively, electrically, or capacitively to one or more of the plurality of electrodes 118. In an embodiment, the power source 700 is configured to deliver a pulsed nondestructive field through tissue of the biological subject that is adjacent to the plurality of electrodes.

The powered surgical implant 2202 can include for example, but not limited to, a control means 2206 for operably coupling to the plurality of electrodes 118. In an embodiment, the control means 2206 is adapted to apply a potential across the plurality of electrodes 2206 from the power source 700. In an embodiment, the applied potential is sufficient to produce superoxidized water from an aqueous salt composition proximate the plurality of electrodes 118 when the powered surgical implant 2202 s implanted within a biological subject. In an embodiment, the applied potential is sufficient to produce at least one of a triplet excited-state specie, a reactive oxygen specie, a reactive nitrogen specie, a free radical, a peroxide, or any other inorganic or organic ion or molecules that include oxygen ions.

In an embodiment, the control means 2206 is operable to control at least one of a spaced-apart electrical sterilizing stimulus delivery pattern component 2206, a spaced-apart electrical sterilizing stimulus delivery pattern component 2208, a spatial electric field modulation component 2210, a spatial electric field distribution component 2212, a spatial illumination field modulation component 2214, or an electrical sterilizing stimulus delivery regimen component 2216.

The powered surgical implant 2202 can include for example, but not limited to, at least one active agent reservoir 2209 for storing a superoxide-forming composition.

Figure 23:
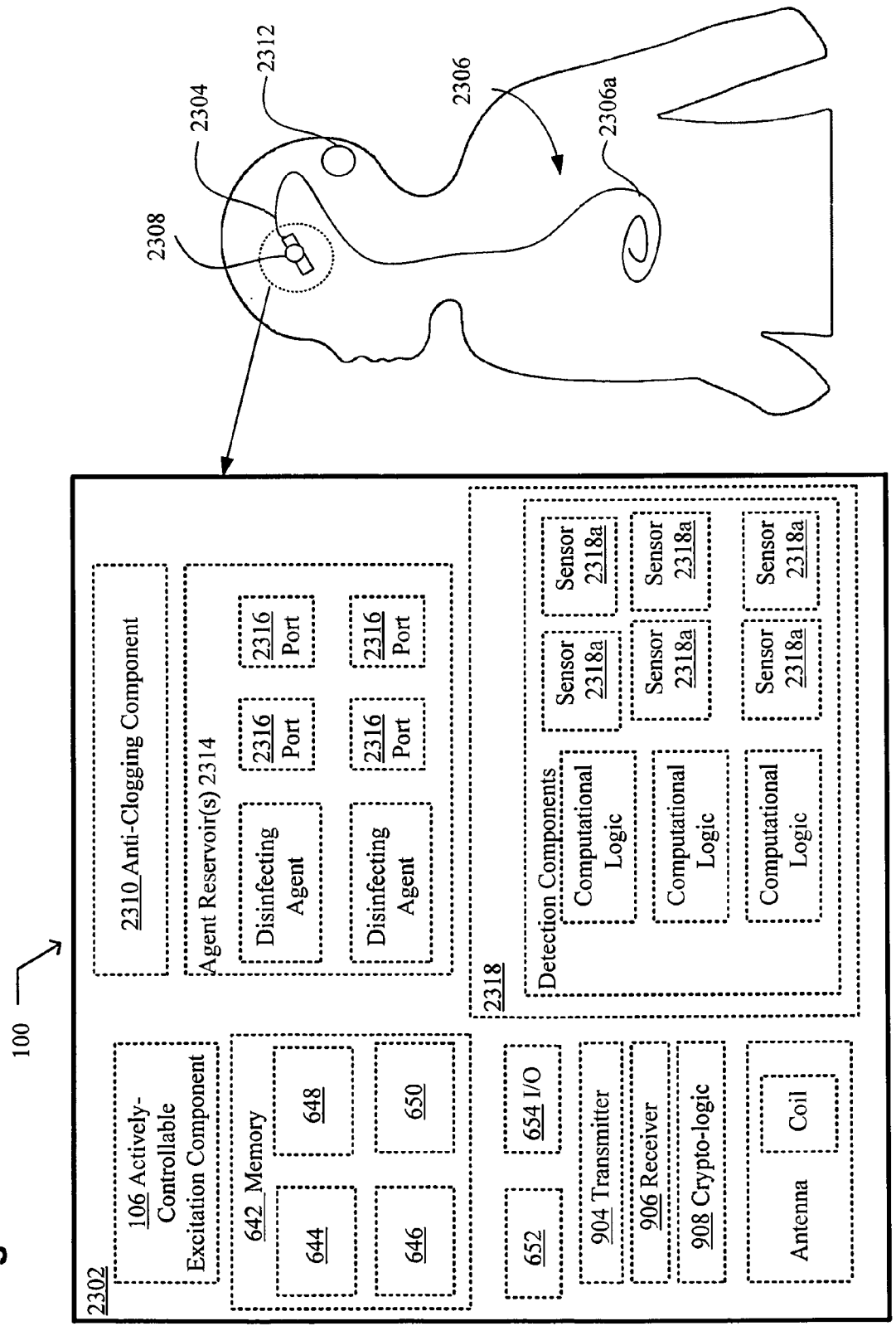
FIG. 23 is a schematic diagram of a system including an implantable device in the form of a cerebrospinal fluid shunt, according to one illustrated embodiment.

The powered surgical implant 2202 can include for example, but not limited to one or more release ports configured to deliver a superoxide-forming composition stored in the active agent reservoir. For example, the powered surgical implant 2202 can include for example, but not limited to one or more controllable-release ports 2211 configured to deliver a superoxide-forming composition stored in the active agent reservoir. In an embodiment, the superoxide-forming composition is an aqueous salt composition. In an embodiment, one or more electrodes of the plurality of electrodes 2206 include a titanium or titanium alloy coating. In an embodiment, the powered surgical implant 2202 comprises a cerebrospinal fluid shunt (FIG. 23). In an embodiment, the powered surgical implant comprises an artificial joint (FIG. 2 is an example of a hip joint implant). The powered surgical implant 2202 can include for example, but not limited to, a first outer coating 2213, the first outer coating including a superoxide-forming composition.

The powered surgical implant 2202 can include for example, but not limited to, one or more outer coatings. In an embodiment, the powered surgical implant 2202 can include a first outer coating including, for example, but not limited to, a self-cleaning coating composition.

In an embodiment, the control means 2206 is adapted to apply a potential across the plurality of electrodes 2206 having parameters selected to produce superoxide species in an interstitial fluid proximate the plurality of electrodes when the powered surgical implant 2202 is implanted within the biological subject. In an embodiment, the applied potential is sufficient to produce superoxide species in an interstitial fluid proximate the plurality of electrodes 2206 when the powered surgical implant 2202 is implanted within the biological subject.

Referring to FIG. 23, in an embodiment, an implantable device 102 comprises an actively-controllable disinfecting cerebrospinal fluid (CSF) shunt (e.g., ventricular shunt) 2302. CSF shunts may be useful to treat, for example, hydrocephalus (a condition including enlarged ventricles). In hydrocephalus, pressure from the cerebrospinal fluid generally increases. Hydrocephalus develops when CSF cannot flow through the ventricular system, or when absorption into the blood stream is not the same as the amount of CSF produced. Indicators for hydrocephalus may include headache, personality disturbances and loss of intellectual abilities (dementia), problems in walking, irritability, vomiting, abnormal eye movements, a low level of consciousness, and the like. Normal pressure hydrocephalus is associated with progressive dementia, problems in walking, and loss of bladder control (urinary incontinence). Non-limiting examples of shunts may be found in, for example the following documents (the contents of which are incorporated herein by reference): U.S. Patent Publication Nos. 2008/0039768 (published Feb. 14, 2008) and 2006/0004317 (published Jan. 5, 2006).

The CSF shunt 2302 can include for example, but is not limit to entry conduits 2304, such as a proximal (ventricular) catheter, into cranium and lateral ventricle, subcutaneous conduits 2306, such as a distal catheter 2306*a*, and one or more valves 2308 for regulation flow of fluid out of the brain and into a peritoneal cavity.

Among valves, examples include, but are not limited to differential pressure valves, one-way valves, flow-regulating or restricting valves, fixed pressure valves, (e.g., DELTA valves by Medtronic Neurological and Spinal), adjustable pressure valves (PS MEDICAL STRATA and STRATA valves by Medtronic Neurological and Spinal), CSF-flow control valves (Medtronic Neurological and Spinal).

The valve can include a flow controlling mechanism that can be non-invasively adjusted to comport, for example, with patient's needs. In an embodiment, The CSF shunt 2302 can include for example, but is not limit to one or more anti-clogging devices 2310.

In an embodiment, a reservoir 2312 may be attached to the tubing and placed under the scalp. This reservoir 2312 can permit samples of cerebrospinal fluid to be removed with a syringe to check the pressure. Fluid from the reservoir 2312 can also be examined for bacteria, cancer cells, blood, or protein, depending on the cause of hydrocephalus. The reservoir 2312 may also be used to inject antibiotics for cerebrospinal fluid infection or chemotherapy medication for meningeal tumors.

In an embodiment, the implantable device 2302 can include, but is not limited to, at least one disinfecting agent reservoir 2314. In an embodiment, disinfecting agent reservoir 2314 includes one or more controllable-release ports 2316 to deliver the at least one disinfecting agent composition form the at least one disinfecting agent reservoir 2314 to an outer surface of the implantable device 2302.

The reservoir 2312 may include circuitry 2318 for, for example, sensing at least one physical quantity, environmental attribute, or physiologic characteristic associated with, for example, a shunting process. For example, in an embodiment, the implantable device 2302 can include, but is not limited to, one or more sensors 2318*a*. In an embodiment, the one or more sensors 2318*a* are configured to determine (e.g., sense, measure, detect, assess, and the like) at least one characteristic associated with the tissue or fluid proximate the outer surface of the implantable device 2302. In an embodiment, the one or more sensors 2318*a* are configured to determine (e.g., sense, measure, detect, assess, and the like) at least one physiological characteristic of the biological subject.

Figure 24:
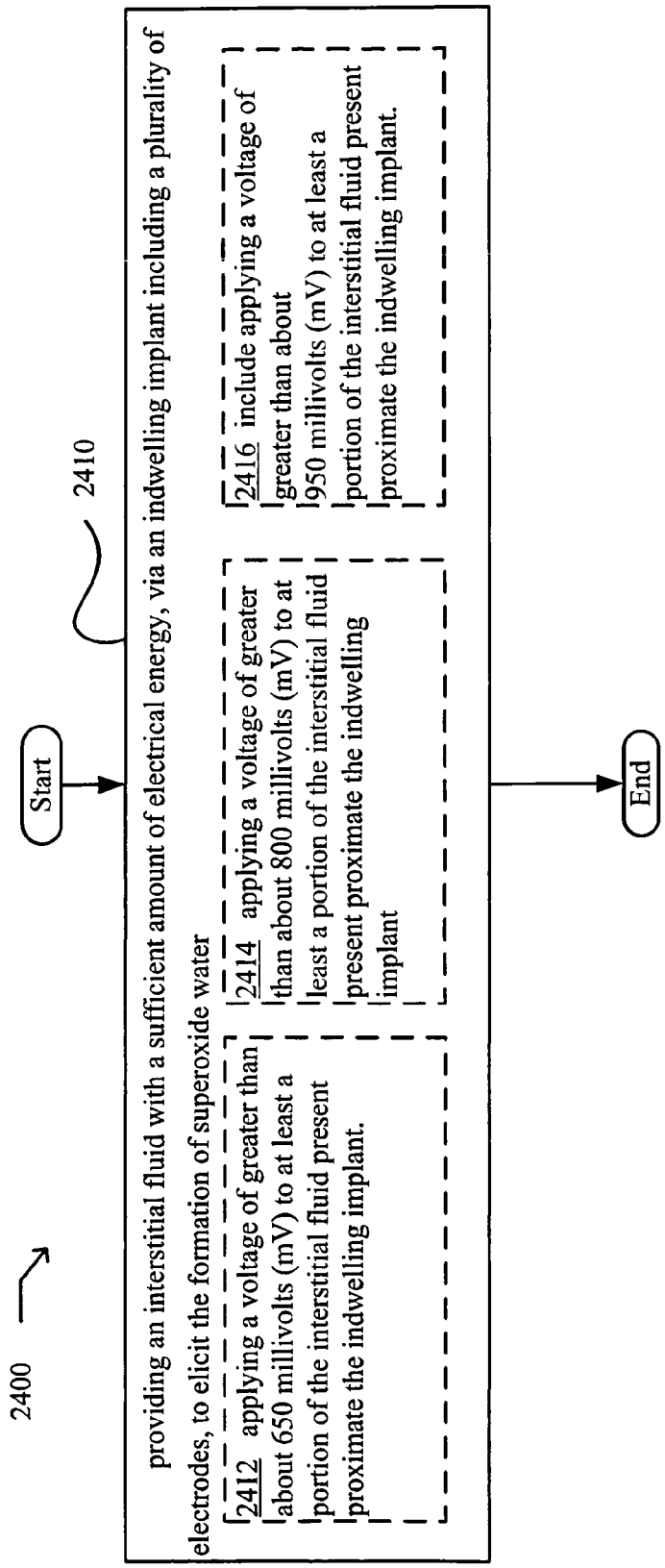
FIG. 24 is a flow diagram of a method of forming an antimicrobial agent, in vivo, according to one illustrated embodiment.

FIG. 24 shows an example of a method 2400 of forming an antimicrobial agent, in vivo.

At 2410, the method 2400 includes providing an interstitial fluid with a sufficient amount of electrical energy, via an indwelling implant including a plurality of electrodes, to elicit the formation of superoxidized water. In an embodiment, the resulting superoxidized water may affect one or more healing or growth promoting properties to the tissue. At 2412, providing the interstitial fluids with the sufficient amount of electrical energy may include applying a voltage of greater than about 650 millivolts (mV) to at least a portion of the interstitial fluid proximate the indwelling implant. At 2414, providing the interstitial fluids with the sufficient amount of electrical energy may include applying a voltage of greater than about 800 millivolts (mV) to at least a portion of the interstitial fluid proximate the indwelling implant. Applying a sufficient voltage to tissue infected with, for example, pathogenic bacteria, may lead to a reduction of the pathogenic bacteria in at least a portion of the infected tissue.

At 2416, providing the interstitial fluids with the sufficient amount of electrical energy may include applying a voltage of greater than about 950 millivolts (mV) to at least a portion of the interstitial fluid proximate the indwelling implant.

Figure 25:
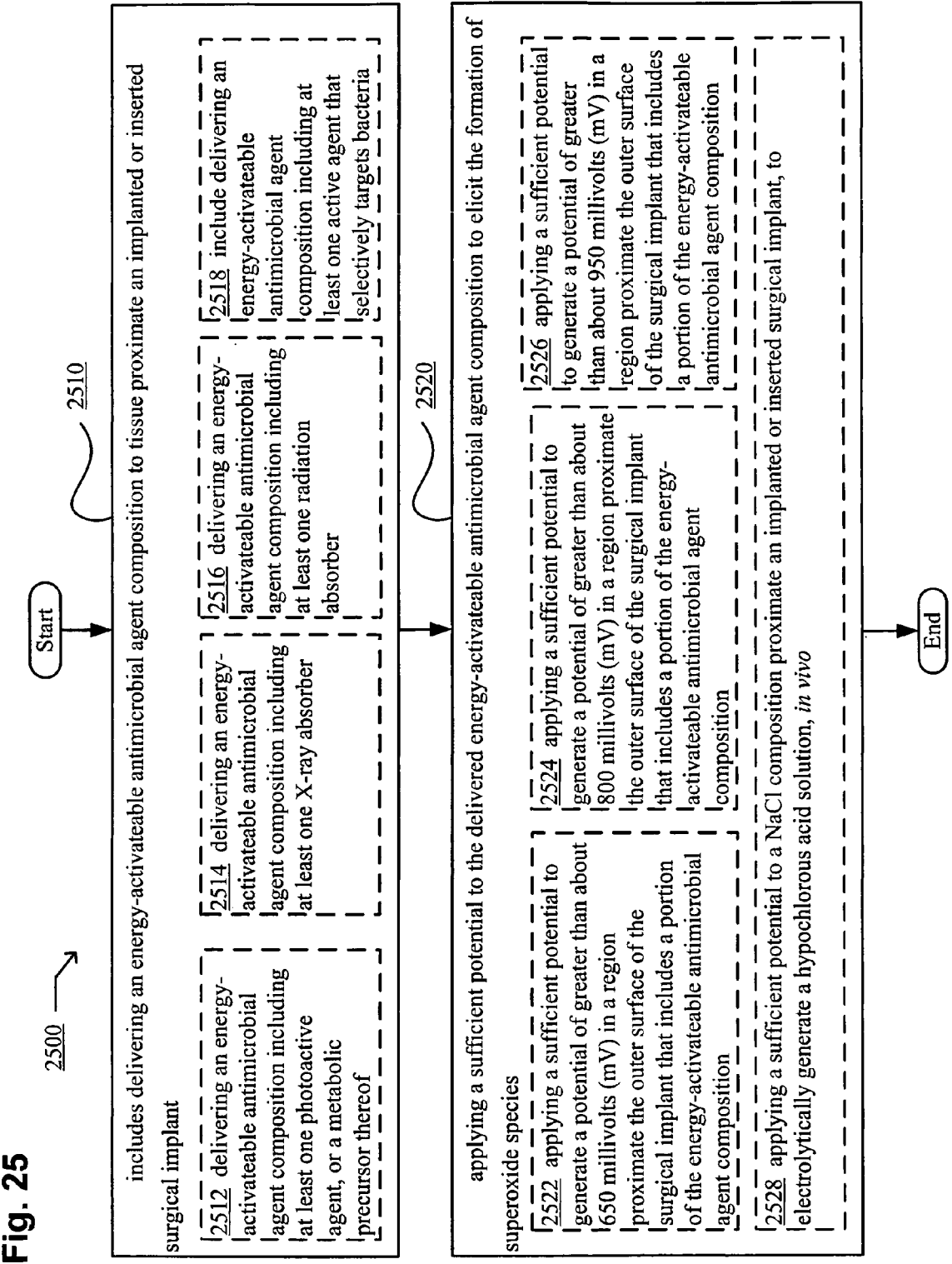
FIG. 25 is a flow diagram of a method of forming an antimicrobial agent, in vivo, according to one illustrated embodiment.

FIG. 25 shows an example of a method 2500 of forming an antimicrobial agent, in vivo.

At 2510, the method 2500 includes delivering an energy-activateable antimicrobial agent composition to tissue proximate an implanted or inserted surgical implant, the implanted or inserted surgical implant including at least one antimicrobial agent reservoir, the antimicrobial agent reservoir configured to deliver an energy-activateable antimicrobial agent composition to tissue proximate an outer surface of the surgical implant, and a plurality of electrodes, the plurality of electrodes operable to energize an energy-activateable antimicrobial agent composition in the presence of an applied potential.

Among antimicrobial agent compositions, examples include, but are not limited to, diluted solutions of NaCl, hypochlorous acid solutions (HAS), oxidative reduction potential aqueous compositions, STERILOX TX (PuriCore Inc.), STERILOX Solutions (PuriCore Inc.), MICROCYN (Nofil Corp.), superoxidized aqueous compositions, superoxidized water, superoxide dismutase compositions, physiologically balanced ionized acidic solutions, and the like. Further non-limiting examples of antimicrobial agent compositions may be found in, for example, the following documents (the contents of which are incorporated herein by reference): U.S. Pat. No. 7,276,255 (issued Oct. 2, 2007), U.S. Pat. No. 7,183,048 (issued Feb. 27, 2007), U.S. Pat. No. 6,506,416 (issued Jan. 14, 2003), U.S. Pat. No. 6,426,066 (issued Jul. 30, 2002), and U.S. Pat. No. 5,622,848 (Apr. 22, 1997); and U.S. Patent Nos. 2007/0196357 (published Aug. 23, 2007), 2007/0173755 (published Jul. 26, 2007), and 2005/0142157 (published Jun. 30, 2005).

At 2512, delivering an energy-activateable antimicrobial agent composition may include delivering an energy-activateable antimicrobial agent composition including at least one photoactive agent, or a metabolic precursor thereof.

At 2514, delivering an energy-activateable antimicrobial agent composition may include delivering an energy-activateable antimicrobial agent composition including at least one X-ray absorber.

At 2516, delivering an energy-activateable antimicrobial agent composition may include delivering an energy-activateable antimicrobial agent composition including at least one radiation absorber.

At 2518, delivering an energy-activateable antimicrobial agent composition may include delivering an energy-activateable antimicrobial agent composition including at least one active agent that selectively targets bacteria.

At 2520, the method 2500 includes applying a sufficient potential to the delivered energy-activateable antimicrobial agent composition to elicit the formation of superoxide species. At 2522, applying the sufficient potential to the delivered energy-activateable antimicrobial agent composition may include applying a sufficient potential to generate a potential of greater than about 650 millivolts (mV) in a region proximate the outer surface of the surgical implant that includes a portion of the energy-activateable antimicrobial agent composition. At 2524, applying the sufficient potential to the delivered energy-activateable antimicrobial agent composition may include applying a sufficient potential to generate a potential of greater than about 800 millivolts (mV) in a region proximate the outer surface of the surgical implant that includes a portion of the energy-activateable antimicrobial agent composition. At 2526, applying the sufficient potential to the delivered energy-activateable antimicrobial agent composition may include applying a sufficient potential to generate a potential of greater than about 950 millivolts (mV) in a region proximate the outer surface of the surgical implant that includes a portion of the energy-activateable antimicrobial agent composition. In an embodiment, the antimicrobial agent compositions ranges in pH from about 5.0 to about 6.5.

At 2528, applying the sufficient potential to the delivered energy-activateable antimicrobial agent composition may include applying a sufficient potential to a NaCl composition proximate an implanted or inserted surgical implant, to electrolytically generate a hypochlorous acid solution (HAS), in vivo, in a region. In an embodiment, the pH of the generated HAS ranges from about 5.5 to about 6.2.

Figure 26:
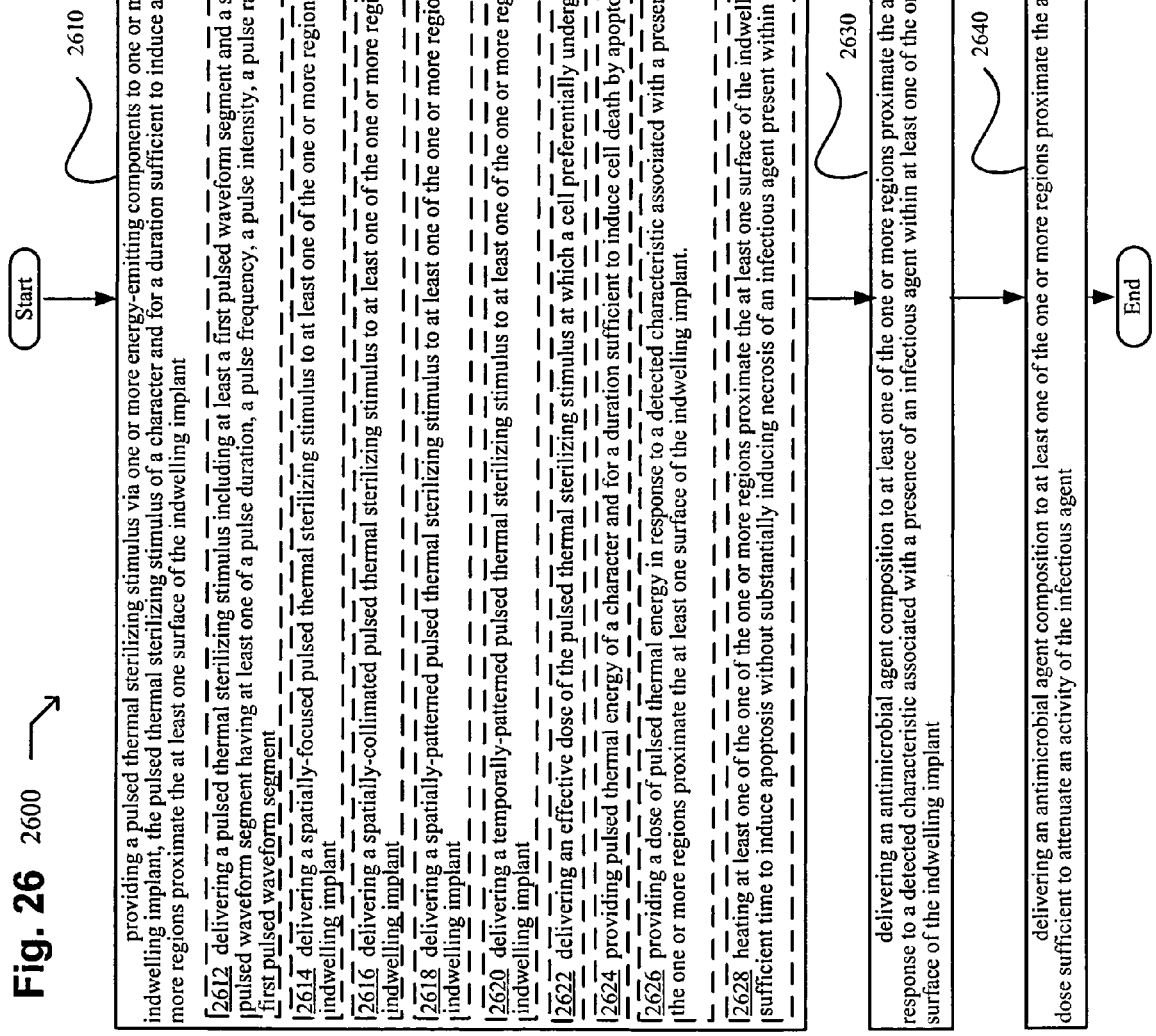
FIG. 26 is a flow diagram of an in vivo method of treating an infectious agent, according to one illustrated embodiment.

FIG. 26 shows an example of an in vivo method 2600 of treating an infectious agent. At 2610, the method 2600 includes providing a pulsed thermal sterilizing stimulus via one or more energy-emitting components to one or more regions proximate at least one surface of an indwelling implant, the pulsed thermal sterilizing stimulus of a character and for a duration sufficient to induce apoptosis of an infectious agent within the one or more regions proximate the at least one surface of the indwelling implant.

At 2612, providing the pulsed thermal sterilizing stimulus includes delivering a pulsed thermal sterilizing stimulus including at least a first pulsed waveform segment and a second pulsed waveform segment, the second pulsed waveform segment having at least one of a pulse duration, a pulse frequency, a pulse intensity, a pulse ratio, or a pulse repetition rate different from the first pulsed waveform segment. In an embodiment, providing the pulsed thermal sterilizing stimulus includes delivering a pulsed thermal sterilizing stimulus including at least a first pulsed waveform segment and a second pulsed waveform segment, the second pulsed waveform segment having a spatial profile different from the first pulsed waveform segment.

At 2614, providing the pulsed thermal sterilizing stimulus includes delivering a spatially-focused pulsed thermal sterilizing stimulus to at least one of the one or more regions proximate the at least one surface of the indwelling implant.

At 2616, providing the pulsed thermal sterilizing stimulus includes delivering a spatially-collimated pulsed thermal sterilizing stimulus to at least one of the one or more regions proximate the at least one surface of the indwelling implant.

At 2618, providing the pulsed thermal sterilizing stimulus includes delivering a spatially-patterned pulsed thermal sterilizing stimulus to at least one of the one or more regions proximate the at least one surface of the indwelling implant.

At 2620, providing the pulsed thermal sterilizing stimulus includes delivering a temporally-patterned pulsed thermal sterilizing stimulus to at least one of the one or more regions proximate the at least one surface of the indwelling implant.

At 2622, providing the pulsed thermal sterilizing stimulus includes delivering an effective dose of the pulsed thermal sterilizing stimulus at which a cell preferentially undergoes apoptosis compared to necrosis.

At 2624, providing the pulsed thermal sterilizing stimulus includes providing pulsed thermal energy of a character and for a duration sufficient to induce cell death by apoptosis.

At 2626, providing the pulsed thermal sterilizing stimulus includes providing a dose of pulsed thermal energy in response to a detected characteristic associated with a presence of an infectious agent within at least one of the one or more regions proximate the at least one surface of the indwelling implant.

At 2628, providing the pulsed thermal sterilizing stimulus includes heating at least one of the one of the one or more regions proximate the at least one surface of the indwelling implant at a temperature and for a sufficient time to induce apoptosis without substantially inducing necrosis of an infectious agent present within the at least one of the one or more regions.

At 2630, the method 2600 can include delivering an antimicrobial agent composition to at least one of the one or more regions proximate the at least one surface of the indwelling implant in response to a detected characteristic associated with a presence of an infectious agent within at least one of the one or more regions proximate the at least one surface of the indwelling implant.

At 2640, the method 2600 can include delivering an antimicrobial agent composition to at least one of the one or more regions proximate the at least one surface of the indwelling implant at a dose sufficient to attenuate an activity of the infectious agent. At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact, many other architectures may be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include but are not limited to physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

Although specific dependencies have been identified in the claims, it is to be noted that all possible combinations of the features of the claims are envisaged in the present application, and therefore the claims are to be interpreted to include all possible multiple dependencies.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. An implantable device, comprising:
    an actively-controllable excitation component configured to deliver a pulsed thermal sterilizing stimulus, in vivo, to a region proximate a surface of the implantable device;
    at least one scaffold-forming material reservoir including one or more controllable-release ports operable to deliver a scaffold-forming material from the at least one scaffold-forming material reservoir to a region proximate a surface of the implantable device;
    a control means operably coupled to the actively-controllable excitation component and configured to regulate at least one of a delivery regimen parameter, a spaced-apart delivery pattern parameter, and a temporal delivery pattern parameter associated with the delivery of the pulsed thermal sterilizing stimulus; and
    a control means configured to control at least one component associated with delivery of the scaffold-forming material from the at least one scaffold-forming material reservoir to a region proximate a surface of the implantable device.

2. The implantable device of claim 1, wherein the actively-controllable excitation component is configured to deliver a pulsed thermal sterilizing stimulus including at least a first pulsed waveform segment and a second pulsed waveform segment, the second pulsed waveform segment having at least one of a pulse duration, a pulse frequency, a pulse intensity, a pulse ratio, or a pulse repetition rate different from the first pulsed waveform segment.

3. The implantable device of claim 2, wherein the control means is configured to control one or more parameters associated with at least one of a pulse duration, a pulse frequency, a pulse intensity, a pulse ratio, or a pulse repetition rate associated with at least one of the first pulsed waveform segment or the second pulsed waveform segment.

4. The implantable device of claim 1, wherein the actively-controllable excitation component is configured to deliver at least one of a spatially-patterned pulsed thermal sterilizing stimulus or a temporally-patterned pulsed thermal sterilizing stimulus.

5. The implantable device of claim 1, wherein the actively-controllable excitation component is configured to concurrently or sequentially provide at least a first pulsed thermal sterilizing stimulus and a second pulsed thermal sterilizing stimulus, the second pulsed thermal sterilizing stimulus having at least one of a duration, a frequency, or an intensity different from the first pulsed thermal sterilizing stimulus.

6. The implantable device of claim 1, wherein the actively-controllable excitation component is configured to concurrently or sequentially provide at least a first pulsed thermal sterilizing stimulus and a second pulsed thermal sterilizing stimulus, the second pulsed thermal sterilizing stimulus having a spatial pattern different from the first pulsed thermal sterilizing stimulus.

7. The implantable device of claim 1, wherein the actively-controllable excitation component is configured to deliver a pulsed thermal sterilizing stimulus of a character and for a duration sufficient to induce a temperature gradient in one or more regions proximate a first outer surface.

8. The implantable device of claim 1, further comprising:
    one or more sensors configured to determine at least one characteristic associated with a biological sample proximate the first outer surface.

9. The implantable device of claim 8, wherein the control means is configured to change at least one of the delivery regimen parameter, the spaced-apart delivery pattern parameter, or the temporal delivery pattern parameter in response to a comparison between one or more real-time measurands associated with a tissue proximate the first outer surface and user specific information.

10. The implantable device of claim 8, wherein the one or more sensors are configured to determine a spatial dependence associated with the at least one characteristic associated with the biological sample proximate the first outer surface.

11. The implantable device of claim 8, wherein the one or more sensors are configured to determine a temporal dependence associated with at least one characteristic associated with the biological sample proximate the first outer surface.

12. The implantable device of claim 8, wherein the at least one characteristic associated with the biological sample proximate the first outer surface includes at least one of a thermal conductivity, a thermal diffusivity, a tissue temperature, or a regional temperature.

13. The implantable device of claim 8, wherein the at least one characteristic associated with biological sample proximate the first outer surface includes a phase change to an interrogation energy stimulus.

14. The implantable device of claim 8, wherein the at least one characteristic associated with the biological sample proximate the first outer surface includes a refractive index parameter.

15. The implantable device of claim 8, wherein the control means is operably coupled to at least a first sensor and at least a second sensor, and is configured to generate a comparison of first sensor data to second sensor data and to generate predictive information based on the comparison.

16. The implantable device of claim 8, wherein the control means is configured to perform a comparison of the at least one characteristic associated with the biological sample proximate the first outer surface to stored reference data and to generate a response based at least in part on the comparison.

17. The implantable device of claim 1, further comprising:
a power source, the power source including at least one of a thermoelectric generator, a piezoelectric generator, an electromechanical generator, or a biomechanical-energy harvesting generator.

18. The implantable device of claim 17, further comprising:
at least one of a battery, a capacitor, and a mechanical energy store.

19. The implantable device of claim 1, further comprising:
a transcutaneous energy transfer system, the transcutaneous energy transfer system electromagnetically, magnetically, ultrasonically, optically, inductively, electrically, or capacitively-coupled to the actively-controllable excitation component.

20. The implantable device of claim 1, further comprising:
a power receiver configured to receive power from an ex vivo power source.

21. The implantable device of claim 1, further comprising:
a power receiver configured to receive power from an in vivo power source.

22. The implantable device of claim 1, further comprising:
a transmitter.

23. An indwelling medical implant, comprising:
a sensor component configured to perform a real-time comparison of a measurand associated with a biological sample proximate one or more regions of at least one surface of the indwelling implant to stored reference data;
one or more energy emitters configured to emit a pulsed thermal sterilizing stimulus of a character and for a time sufficient to induce apoptosis without substantially inducing necrosis of at least a portion of cells proximate the indwelling medical implant in response to the comparison; and
at least one scaffold-forming material reservoir operable to deliver a scaffold-forming material from the at least one scaffold-forming material reservoir to a region proximate a surface of the implantable device.

24. The indwelling medical implant of claim 23, wherein at least one of the one or more energy emitters is configured to emit a pulsed thermal sterilizing stimulus of a character and for a time sufficient to induce apoptosis without substantially inducing necrosis of an infectious agent within a tissue proximate the indwelling medical implant in response to a detected level of an infectious agent.

25. The indwelling medical implant of claim 23, wherein at least one of the one or more energy emitters is configured to emit a pulsed thermal sterilizing stimulus of a character and for a time sufficient to induce apoptosis without substantially inducing necrosis of a pathogen within a region proximate the indwelling medical implant.

26. The indwelling medical implant of claim 23, wherein the one or more energy emitters are operable to emit a sufficient amount of a pulsed thermal sterilizing stimulus to increase the temperature of at least a portion of cells proximate the indwelling medical implant by about 3° C. to about 22° C.

27. An implantable system, comprising:
circuitry for delivering a pulsed thermal sterilizing stimulus, in vivo, to a region proximate a surface of an indwelling medical implant, the pulsed thermal sterilizing stimulus of a character and for a time sufficient to induce apoptosis without substantially inducing necrosis of at least a portion of cells within the region proximate the indwelling medical implant;
circuitry for regulating at least one parameter associated with the delivery of the pulsed thermal sterilizing stimulus in response to a determination that an infectious agent is present within the region proximate the indwelling medical implant; and
circuitry for controlling at least one parameter associated with a delivery of a scaffold-forming material to a region proximate a surface of an indwelling medical implant.

28. The implantable system of claim 27, wherein the circuitry for delivering the pulsed thermal sterilizing stimulus includes one or more energy emitters configured to deliver a pulsed thermal sterilizing stimulus of a character and for a time sufficient to induce apoptosis without substantially inducing necrosis of the at least a portion of cells proximate the indwelling medical implant.

29. The implantable system of claim 27, wherein the circuitry for delivering the pulsed thermal sterilizing stimulus includes an actively-controllable excitation component configured to deliver a spatially-focused pulsed thermal sterilizing stimulus.

30. The implantable system of claim 27, wherein the circuitry for delivering the pulsed thermal sterilizing stimulus includes an actively-controllable excitation component configured to deliver a spatially-collimated pulsed thermal sterilizing stimulus.

31. The implantable system of claim 27, wherein the circuitry for delivering the pulsed thermal sterilizing stimulus includes an actively-controllable excitation component configured to deliver at least one of a spatially-patterned pulsed thermal sterilizing stimulus or a temporally-patterned pulsed thermal sterilizing stimulus.

32. The implantable system of claim 27, wherein the circuitry for regulating the at least one parameter associated with the delivery of the pulsed thermal sterilizing stimulus is operably coupled to the circuitry for delivering the pulsed thermal sterilizing stimulus and configured to control at least one of a pulsed thermal sterilizing stimulus delivery regimen parameter, a spaced-apart pulsed thermal sterilizing stimulus delivery pattern parameter, or a pulsed thermal sterilizing stimulus temporal delivery pattern parameter.

33. The implantable system of claim 27, wherein the circuitry for regulating the at least one parameter associated with the delivery of the pulsed thermal sterilizing stimulus is configured to control at least one of a pulsed thermal sterilizing stimulus delivery regimen parameter, a pulsed thermal sterilizing stimulus temporal delivery pattern parameter, or a spaced-apart pulsed thermal sterilizing stimulus delivery pattern parameter associated with the delivery of the pulsed thermal sterilizing stimulus.

* * * * *

UNITED STATES PATENT AND TRADEMARK OFFICE
CERTIFICATE OF CORRECTION

PATENT NO. : 9,005,263 B2  
APPLICATION NO. : 12/592976  
DATED : April 14, 2015  
INVENTOR(S) : Edward S. Boyden et al.

It is certified that error appears in the above-identified patent and that said Letters Patent is hereby corrected as shown below:

In the Specification

In column 1, line 38 please replace "12/315,885, entitled SYSTEM, DEVICES, AND METHODS INCLUDING ACTIVELY-CONTROLLABLE ELECTROSTATIC AND ELECTROMAGNETIC STERILIZING EXCITATION DELIVERY SYSTEM" with --12/315,882, entitled SYSTEM, DEVICES, AND METHODS INCLUDING STERILIZING EXCITATION DELIVERY IMPLANTS WITH GENERAL CONTROLLERS AND ONBOARD POWER--

Signed and Sealed this
Eighth Day of December, 2015

Michelle K. Lee
*Director of the United States Patent and Trademark Office*